United States Patent
Zhang et al.

(10) Patent No.: US 12,264,146 B2
(45) Date of Patent: Apr. 1, 2025

(54) RHO KINASE INHIBITOR, METHOD FOR PREPARING SAME AND USES THEREOF

(71) Applicant: BEIJING INCREASE INNOVATIVE DRUG CO., LTD., Beijing (CN)

(72) Inventors: Baoxian Zhang, Beijing (CN); Hongwu Zhang, Beijing (CN); Jie Hu, Beijing (CN); Zhiyun Kang, Beijing (CN); Chunmei Xue, Beijing (CN); Wenhui Li, Beijing (CN); Yanwei Song, Beijing (CN); Zhenzhen Wu, Beijing (CN); Anping Chen, Beijing (CN); Fang Wang, Beijing (CN); Hengchun Ren, Beijing (CN); Jun Li, Beijing (CN)

(73) Assignee: Beijing Increase Innovative Drug Co., LTD, Beijing (CN)

( * ) Notice: Subject to any disclaimer, the term of this patent is extended or adjusted under 35 U.S.C. 154(b) by 987 days.

(21) Appl. No.: 17/290,045

(22) PCT Filed: May 6, 2019

(86) PCT No.: PCT/CN2019/085689
§ 371 (c)(1),
(2) Date: Apr. 29, 2021

(87) PCT Pub. No.: WO2020/087901
PCT Pub. Date: May 7, 2020

(65) Prior Publication Data
US 2022/0002265 A1  Jan. 6, 2022

(30) Foreign Application Priority Data
Oct. 30, 2018 (CN) .......................... 201811275571.0

(51) Int. Cl.
*C07D 401/12* (2006.01)
*A61P 9/10* (2006.01)

(52) U.S. Cl.
CPC .............. *C07D 401/12* (2013.01); *A61P 9/10* (2018.01)

(58) Field of Classification Search
CPC .......... C07D 401/12; A61P 9/10; A61P 25/00; Y02P 20/55; A61K 31/551
See application file for complete search history.

(56) References Cited

U.S. PATENT DOCUMENTS

| | | |
|---|---|---|
| 6,153,608 A | 11/2000 | Hidaka et al. |
| 2007/0088021 A1* | 4/2007 | Hidaka ................ A61P 27/06 514/218 |
| 2008/0064681 A1 | 3/2008 | Hidaka et al. |

FOREIGN PATENT DOCUMENTS

| | | |
|---|---|---|
| CN | 1210521 A | 3/1999 |
| CN | 105906609 A | 8/2016 |
| EP | 0187371 * | 7/1986 |
| EP | 0187371 A2 * | 7/1986 |
| EP | 0 885 888 A1 | 12/1998 |
| EP | 0 956 865 A1 | 11/1999 |
| EP | 1 074 545 A1 | 2/2001 |
| WO | WO-99/20620 A1 | 4/1999 |
| WO | WO-2004/106325 A1 | 12/2004 |

OTHER PUBLICATIONS

Extended European Search Report mailed on Jul. 8, 2022, for EP Application No. 19 880 065.8, 13 pages.
Isobe, T. et al. (2015). "Species differences in metabolism of ripasudil (K-115) are attributed to aldehyde oxidase," Xenobiotica 46:579-590.
Lograsso, P. V. et al. (2009). "Rho kinase (ROCK) inhibitors and their application to inflammatory disorders," Curr. Topics Med. Chem. 9:704-723.
Nuhant, P. et al. (2017). "Visible-Light Initiated Manganese-Based Catalysis for C—H Alkylation of Heteroarenes: Applications and Mechanistic Studies," Angewandte Chemie International Edition 56:15309-15313.
Wang, P. et al. (2016). "Selective inhibition of ROCK kinase isoforms to promote neuroregeneration after brain surgery," Med. Chem. Res. 25:40-50.
Lai, J.Y.Q. et al. (2005). "Preparation of Kinase-biased compounds in the search for lead inhibitors of Kinase targets," Med. Res. Rev. 25:310-330.
Sugawara, T. et al. (2008). "A new grading system evaluating bleeding scale in filament perforation subarachnoid hemorrhage rat model," J Neurosci. Methods 167:327-334.

* cited by examiner

*Primary Examiner* — Matthew P Coughlin
*Assistant Examiner* — Meghan C Heasley
(74) *Attorney, Agent, or Firm* — COOLEY LLP

(57) ABSTRACT

Provided are a Rho kinase inhibitor, a method for preparing same and the uses thereof. The Rho kinase inhibitor designates a compound of Formula I, a stereoisomer thereof or pharmaceutically acceptable salt thereof. The Rho kinase inhibitor promotes endothelial cells and endothelin expression, prostenin expression, and vascular factors NO synthesis and secretion, has a promoting effect on proprostin expression independently of the doses used, shows lower toxicity, while being safer.

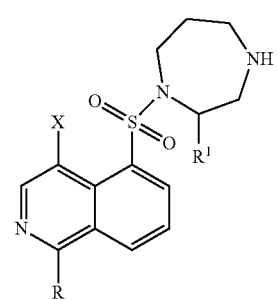

Formula I

17 Claims, 3 Drawing Sheets

RHO KINASE INHIBITOR, METHOD FOR PREPARING SAME AND USES THEREOF

CROSS-REFERENCE TO RELATED APPLICATIONS

The present application is a U.S. National Phase application, filed under 35 U.S.C. § 371 (c), of International Application No. PCT/CN2019/085689, filed May 6, 2019, which claims the benefit of, and priority to Chinese application No. 201811275571.0, filed on Oct. 30, 2018, the disclosures of each of which are incorporated herein by reference in its entirety.

TECHNICAL FIELD

The present application belongs to the field of chemical medicine, and specifically relates to a Rho kinase inhibitor, a method for preparing the same and a use thereof.

BACKGROUND ART

Rho kinase (Rho-associated protein kinase, ROCK) is one of the earliest discovered downstream targets of Rho protein. ROCK, which is a class of serine/threonine protein kinases with a relative molecular mass of 160 kDa, includes ROCKI and ROCKII subtypes. The molecular structure of ROCK comprises an amino-terminal kinase domain/catalytic domain (CD), a central coiled-coil domain comprising a Rho binding domain, a carboxy-terminal pleckstrin-homology domain (PH), and a cysteine-rich domain (CRD). Studies have found that ROCK is involved in a variety of cellular functions, such as smooth muscle contraction, stress fiber formation, cytoskeletal remodeling, cell differentiation and migration, cell apoptosis, etc., and ROCK is overexpressed in the pathological processes of a variety of cardiovascular and cerebrovascular diseases.

So far, the ROCK inhibitors discovered are all small molecular organic compounds, mainly including isoquinolines, 4-aminopyridines, indazoles, amides and ureas. These small molecule inhibitors take effects by binding to the ATP binding site of catalytic domain in the Rho kinase. Because the amino acid sequence of the ATP binding site domain in the protein kinase has high homology, the above small molecule inhibitors can block ROCK and antagonize protein kinases such as PKA, PKG and PKC simultaneously, while this inevitably causes some adverse reactions.

In view of this, the present application provides a new type of Rho kinase inhibitor to antagonize ROCK with high selectivity.

Contents of the Disclosure

In order to solve the above technical problem, the present application provides a Rho kinase inhibitor, a method for preparing the same and a use thereof.

The present application provides a Rho kinase inhibitor, in which the Rho kinase inhibitor is a compound represented by Formula I, a stereoisomer thereof or a pharmaceutically acceptable salt thereof:

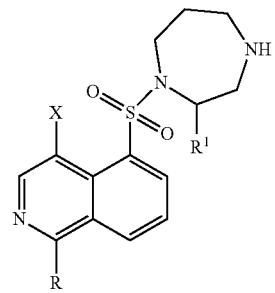

Formula I wherein X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino,

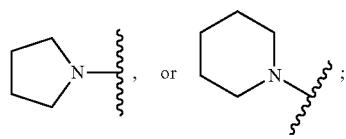 [SMILES: *N1CCCC1 ; *N1CCCCC1]

R is hydrogen, hydroxyl, $CH_3(CH_2)_mO-$, $CH_3(CH_2)_n COO-$ or $HCO-$; m and n are each independently 0, 1, 2, 3;

$R^1$ is hydrogen, $C_1$ to $C_5$ chain alkyl, or $C_3$ to $C_6$ cycloalkyl;

and the three substituents X, R and $R^1$ are not hydrogen at the same time.

In some embodiments, m is 0.
In some embodiments, m is 1.
In some embodiments, m is 2.
In some embodiments, m is 3.
In some embodiments, n is 0.
In some embodiments, n is 1.
In some embodiments, n is 2.
In some embodiments, n is 3.
In some embodiments, in Formula I, X is hydrogen, halogen, or $C_1$ to $C_5$ chain alkyl.
In some embodiments, in Formula I, X is hydrogen, fluorine, chlorine, bromine, methyl, ethyl, n-propyl, isopropyl, n-butyl, isobutyl, sec-butyl, tert-butyl, cyclopropyl, cyclobutyl, cyclopentyl or cyclohexyl.
In some embodiments, in Formula I, X is hydrogen, fluorine, chlorine, ethyl, or cyclopropyl.
In some embodiments, in Formula I, X is hydrogen.
In some embodiments, in Formula I, X is fluorine
In some embodiments, in Formula I, X is chlorine.
In some embodiments, in Formula I, X is bromo.
In some embodiments, in Formula I, X is methyl.
In some embodiments, in Formula I, X is ethyl.
In some embodiments, in Formula I, X is n-propyl.
In some embodiments, in Formula I, X is isopropyl.
In some embodiments, in Formula I, X is n-butyl.
In some embodiments, in Formula I, X is isobutyl.
In some embodiments, in Formula I, X is sec-butyl.
In some embodiments, in Formula I, X is tert-butyl.
In some embodiments, in Formula I, X is cyclopropyl.
In some embodiments, in Formula I, X is cyclobutyl.
In some embodiments, in Formula I, X is cyclopentyl.
In some embodiments, in Formula I, R is hydrogen, hydroxy, methoxy, ethoxy, propoxy, butoxy.

In some embodiments, in Formula I, R is hydrogen, hydroxy, or methoxy.

In some embodiments, in Formula I, R is hydrogen.
In some embodiments, in Formula I, R is hydroxy.
In some embodiments, in Formula I, R is methoxy.
In some embodiments, in Formula I, R is ethoxy.
In some embodiments, in Formula I, R is propoxy.
In some embodiments, in Formula I, R is butoxy.
In some embodiments, in Formula I, $R^1$ is hydrogen, or $C_1$ to $C_5$ chain alkyl.

In some embodiments, in Formula I, $R^1$ is hydrogen, methyl, ethyl, n-propyl, isopropyl, n-butyl, isobutyl, sec-butyl, tert-butyl, n-pentyl, isopentyl, sec-pentyl, tert-pentyl, neopentyl, cyclopropyl, cyclobutyl, cyclopentyl or cyclohexyl.

In some embodiments, in Formula I, $R^1$ is methyl, ethyl, isopropyl, n-butyl, isopentyl, or cyclopropyl.

In some embodiments, in Formula I, $R^1$ is hydrogen.
In some embodiments, in Formula I, $R^1$ is methyl.
In some embodiments, in Formula I, $R^1$ is ethyl.
In some embodiments, in Formula I, $R^1$ is n-propyl.
In some embodiments, in Formula I, $R^1$ is isopropyl.
In some embodiments, in Formula I, $R^1$ is n-butyl.
In some embodiments, in Formula I, $R^1$ is isobutyl.
In some embodiments, in Formula I, $R^1$ is tert-butyl.
In some embodiments, in Formula I, $R^1$ is n-pentyl.
In some embodiments, in Formula I, $R^1$ is isopentyl.
In some embodiments, in Formula I, $R^1$ is sec-pentyl.
In some embodiments, in Formula I, $R^1$ is tert-pentyl.
In some embodiments, in Formula I, $R^1$ is neopentyl.
In some embodiments, in Formula I, $R^1$ is cyclopropyl.
In some embodiments, in Formula I, $R^1$ is cyclobutyl.
In some embodiments, in Formula I, $R^1$ is cyclopentyl.
In some embodiments, in Formula I, $R^1$ is cyclohexyl.

In some embodiments, in Formula I, when $R^1$ is methyl, the substituents X and R are not hydrogen at the same time.

In some embodiments, the compound represented by Formula I is selected from the group consisting of
4-cyclopropyl-5-((2-methyl-1,4-diazacycloheptan-1-yl)sulfonyl)isoquinolin-1-ol;
4-cyclopropyl-1-methoxy-5-((2-methyl-1,4-diazacycloheptan-1-yl)sulfonyl)isoquinoline;
5-((2-cyclopropyl-1,4-diazacycloheptan-1-yl)sulfonyl)-4-fluoroisoquinolin-1-ol;
5-((2-cyclopropyl-1,4-diazacycloheptan-1-yl)sulfonyl)-4-fluoroisoquinoline;
5-((2-methyl-1,4-diazacycloheptan-1-yl)sulfonyl)isoquinolin-1-ol;
1-methoxy-5-((2-methyl-1,4-diazacycloheptan-1-yl)sulfonyl)isoquinoline;
4-fluoro-5-((2-methyl-1,4-diazacycloheptan-1-yl)sulfonyl)isoquinolin-1-ol;
4-fluoro-1-methoxy-5-((2-methyl-1,4-diazacycloheptan-1-yl)sulfonyl)isoquinoline;
4-chloro-5-((2-methyl-1,4-diazacycloheptan-1-yl)sulfonyl)isoquinolin-1-ol;
4-chloro-5-((2-methyl-1,4-diazacycloheptan-1-yl)sulfonyl)isoquinoline;
5-((2-isopropyl-1,4-diazacycloheptan-1-yl)sulfonyl)isoquinolin-1-ol;
5-((2-isopropyl-1,4-diazacycloheptan-1-yl)sulfonyl)-1-methoxyisoquinoline;
5-((2-n-butyl-1,4-diazacycloheptan-1-yl)sulfonyl)isoquinolin-1-ol; and
5-((2-n-butyl-1,4-diazacycloheptan-1-yl)sulfonyl)-1-methoxyisoquinoline.

In some embodiments, the compound represented by Formula I is an optical isomer with R configuration.

In some embodiments, the compound represented by Formula I is selected from the group consisting of:
(R)-4-cyclopropyl-5-((2-methyl-1,4-diazacycloheptan-1-yl)sulfonyl)isoquinolin-1-ol;
(R)-4-cyclopropyl-1-methoxy-5-((2-methyl-1,4-diazacycloheptan-1-yl)sulfonyl)isoquinoline;
(R)-5-((2-cyclopropyl-1,4-diazacycloheptan-1-yl)sulfonyl)-4-fluoroisoquinoline-1-ol;
(R)-5-((2-cyclopropyl-1,4-diazacycloheptan-1-yl)sulfonyl)-4-fluoroisoquinoline;
(R)-5-((2-methyl-1,4-diazacycloheptan-1-yl)sulfonyl)isoquinolin-1-ol;
(R)-1-methoxy-5-((2-methyl-1,4-diazacycloheptan-1-yl)sulfonyl)isoquinoline;
(R)-5-((2-methyl-1,4-diazacycloheptan-1-yl)sulfonyl)isoquinoline;
(R)-4-fluoro-5-((2-methyl-1,4-diazacycloheptan-1-yl)sulfonyl)isoquinolin-1-ol;
(R)-4-fluoro-1-methoxy-5-((2-methyl-1,4-diazacycloheptan-1-yl)sulfonyl)isoquinoline;
(R)-4-chloro-5-((2-methyl-1,4-diazacycloheptan-1-yl)sulfonyl)isoquinolin-1-ol;
(R)-4-chloro-5-((2-methyl-1,4-diazacycloheptan-1-yl)sulfonyl)isoquinoline;
(R)-5-((2-isopropyl-1,4-diazacycloheptan-1-yl)sulfonyl)isoquinolin-1-ol;
(R)-5-((2-isopropyl-1,4-diazacycloheptan-1-yl)sulfonyl)-1-methoxyisoquinoline;
(R)-5-((2-n-butyl-1,4-diazacycloheptan-1-yl)sulfonyl)isoquinolin-1-ol; and
(R)-5-((2-n-butyl-1,4-diazacycloheptan-1-yl)sulfonyl)-1-methoxyisoquinoline.

In some embodiments, the compound represented by Formula I is an optical isomer with S configuration.

In some embodiments, the pharmaceutically acceptable salt is a salt formed by the compound represented by Formula I and inorganic acid or organic acid; preferably, the salt formed by the compound represented by Formula I and inorganic acid is sulfate, hydrochloride, nitrate, phosphate, or hydrobromide.

In some embodiments, the salt formed by the compound represented by Formula I and organic acid is any one selected from the group consisting of acetate, formate, methanesulfonate, trifluoroacetate, maleate, tartrate, succinate, fumarate, citrate, benzenesulfonate, benzoate, lactate, malate, and amino acid salt; preferably, the amino acid salt is aspartate, glutamate, glycinate, alaninate, valinate, leucinate, isoleucinate, phenylalaninate, prolinate, tryptophanate, serinate, tyrosinate, cysteinate, methioninate, asparaginate, glutaminate, or threoninate.

The present application also provides a method for preparing the compound represented by Formula I, a stereoisomer thereof or a pharmaceutically acceptable salt thereof, comprising:

allowing a compound represented by Formula II to undergo a deprotection reaction to remove the protective group PG to prepare the compound represented by the Formula I, Formula II wherein, the definitions of X, R, R$^1$ and PG are as described in any embodiment of the present application, for example, X is hydrogen, halogen, C$_1$ to C$_5$ chain alkyl, C$_3$ to C$_6$ cycloalkyl, benzyl, phenyl, methoxy, ethoxy, propoxy, methylamino, ethylamino, propylamino, R is hydrogen, hydroxyl, CH$_3$(CH$_2$)$_m$O—, CH$_3$(CH$_2$)$_n$COO— or HCO—; m and n are each independently 0, 1, 2, 3;

R$^1$ is hydrogen, C$_1$ to C$_5$ chain alkyl, or C$_3$ to C$_6$ cycloalkyl;

and the three substituents X, R and R$^1$ are not hydrogen at the same time;

PG is tert-butoxycarbonyl (Boc-) or benzyloxycarbonyl (Cbz-).

In some embodiments, the compound represented by Formula II is prepared by a cyclization reaction of a compound represented by Formula III, Formula III wherein, the definitions of X, R, R$^1$ and PG are as described in any embodiment of the present application, for example, X is hydrogen, halogen, C$_1$ to C$_5$ chain alkyl, C$_3$ to C$_6$ cycloalkyl, benzyl, phenyl, methoxy, ethoxy, propoxy, methylamino, ethylamino, propylamino, R is hydrogen, hydroxyl, CH$_3$(CH$_2$)$_m$O—, CH$_3$(CH$_2$)$_n$COO— or HCO—; m and n are each independently 0, 1, 2, 3;

R is hydrogen, C$_1$ to C$_5$ chain alkyl, or C$_3$ to C$_6$ cycloalkyl;

and the three substituents X, R and R$^1$ are not hydrogen at the same time;

PG is tert-butoxycarbonyl (Boc-) or benzyloxycarbonyl (Cbz-).

In some embodiments, the compound represented by Formula III is prepared by a deprotection reaction of a compound represented by Formula IV, Formula IV wherein, the definitions of X, R, R$^1$, PG and PG$^1$ are as described in any embodiment of the present application, for example, X is hydrogen, halogen, C$_1$ to C$_5$ chain alkyl, C$_3$ to C$_6$ cycloalkyl, benzyl, phenyl, methoxy, ethoxy, propoxy, methylamino, ethylamino, propylamino, R is hydrogen, hydroxyl, CH$_3$(CH$_2$)$_m$O—, CH$_3$(CH$_2$)$_n$COO— or HCO—; m and n are each independently 0, 1, 2, 3;

R$^1$ is hydrogen, C$_1$ to C$_5$ chain alkyl, or C$_3$ to C$_6$ cycloalkyl;

and the three substituents X, R and R$^1$ are not hydrogen at the same time;

PG is tert-butoxycarbonyl (Boc-) or benzyloxycarbonyl (Cbz-).

PG$^1$ is tert-butyldimethylsilyl (TBS-) or trimethylsilyl (TMS-).

In some embodiments, the compound represented by Formula IV is prepared by reacting a compound represented by Formula V with a compound represented by Formula VI, Formula V

[Structure: isoquinoline with SO₂Cl at position 5, X at position 4, R at position 1]

Formula VI

[Structure: HN-CHR¹-CH₂-N(PG)-CH₂CH₂CH₂-O-PG¹]

wherein, the definitions of X, R, R¹, PG and PG¹ are as described in any embodiment of the present application, for example, X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino,

[Structures: pyrrolidin-1-yl, or piperidin-1-yl];

R is hydrogen, hydroxyl, $CH_3(CH_2)_mO-$, $CH_3(CH_2)_nCOO-$ or HCO—; m and n are each independently 0, 1, 2, 3;

R¹ is hydrogen, $C_1$ to $C_5$ chain alkyl, or $C_3$ to $C_6$ cycloalkyl;

and the three substituents X, R and R¹ are not hydrogen at the same time;

PG is tert-butoxycarbonyl (Boc-) or benzyloxycarbonyl (Cbz-).

PG¹ is tert-butyldimethylsilyl (TBS-) or trimethylsilyl (TMS-).

In some embodiments, the compound represented by Formula V is prepared by reacting a compound represented by Formula VII with chlorosulfonic acid, Formula VII

[Structure: isoquinoline with X at position 4, R at position 1]

wherein, the definitions of X, R are as described in any embodiment of the present application, for example, X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino,

[Structures: pyrrolidin-1-yl, or piperidin-1-yl];

R is hydrogen, hydroxyl, $CH_3(CH_2)_mO-$, $CH_3(CH_2)_nCOO-$ or HCO—; m and n are each independently 0, 1, 2, 3.

The present application also provides a use of the compound of Formula I, a stereoisomer thereof or a pharmaceutically acceptable salts thereof in manufacture of the medicament for the prevention and/or treatment of a subarachnoid hemorrhage, or a vasospasm or cerebral ischemia caused by subarachnoid hemorrhage, or in manufacture of the medicament for selective expansion of spasmodic blood vessel, improvement of cardiac/cerebral ischemia, improvement of cerebral perfusion, enhancement of brain anti-hypoxic ability, inhibition of brain nerve cell damage, promotion of neuronal axon growth, or alleviation of inflammatory response of affected brain cellular tissue.

In some embodiments, the subarachnoid hemorrhage is a primary subarachnoid hemorrhage or a secondary subarachnoid hemorrhage.

The present application also provides a use of the compound represented by Formula I, a stereoisomer thereof or a pharmaceutically acceptable salt thereof in manufacture of the medicament for promoting the expression and secretion of a vasoconstriction factor, or promoting the expression of a vascular endothelium-derived relaxing factor, and the like.

In some embodiments, the vasoconstriction factor comprises endothelin factor, and the vascular endothelium-derived relaxing factor comprises a prostacyclin factor, a nitric oxide synthase factor, and a nitric oxide factor.

The present application also provides a pharmaceutical composition comprising the compound represented by Formula I, a stereoisomer thereof or a pharmaceutically acceptable salt thereof as an active ingredient and at least one pharmaceutically acceptable excipient, such as carrier or excipient.

In some embodiments, the pharmaceutical composition is administered by oral, injection, transdermal, nasal, mucosal, or inhalation.

In some embodiments, the composition is an ordinary preparation, or a sustained-release, controlled-release, targeted or immediate-release preparation.

The present application also provides the compound represented by Formula I, a stereoisomer thereof or a pharmaceutically acceptable salt thereof, for use in the prevention and/or treatment of a subarachnoid hemorrhage, or a vasospasm or cerebral ischemia caused by subarachnoid hemorrhage, or for use in selectively expanding spasmodic blood vessel, improving cardiac/cerebral ischemia, improving cerebral perfusion, enhancing brain anti-hypoxic ability, inhibiting brain verve cell damage, promoting neuronal axon growth, or alleviating inflammatory response of affected brain cellular tissue; or for use in promoting the expression and secretion of a vasoconstriction factor, or promoting the expression of a vascular endothelium-derived relaxing factor.

The present application also provides a method for preventing and/or treating a subarachnoid hemorrhage, or a vasospasm or cerebral ischemia caused by subarachnoid hemorrhage, selectively expanding spasmodic blood vessel, improving cardiac/cerebral ischemia, improving cerebral perfusion, enhancing brain anti-hypoxic ability, inhibiting brain nerve cell damage, promoting neuron axon growth, or alleviating inflammatory response of affected brain cellular tissue, comprising administering a prophylactically or therapeutically effective amount of the compound represented by Formula I, a stereoisomer thereof or a pharmaceutically acceptable salt thereof to a subject in need of such treatment.

The present application also provides a method for promoting the expression and secretion of vasoconstriction factor in a cell, or promoting the expression of vascular endothelium-derived relaxing factor in a cell comprising: contacting the compound represented by Formula I, a stereoisomer thereof or a pharmaceutically acceptable salt thereof with the cell.

The pharmaceutical composition described in the present application may comprise one or more compounds of the present application. In some embodiments, the pharmaceutical composition may comprise more than one compound of the present application. For example, in some embodiments, the pharmaceutical composition may comprise two or more compounds of the present application. In addition, the pharmaceutical composition may optionally further comprise one or more additional pharmaceutically active compounds.

According to the present application, the pharmaceutical composition comprises the compound represented by Formula I of the present application and a pharmaceutically acceptable carrier or excipient. The pharmaceutical composition may be administered via, for example, oral or parenteral route. According to conventional methods in the art, the pharmaceutical composition of the present application may be prepared into various preparation forms including but not limited to tablets, capsules, solutions, suspensions, granules or injections, etc., for administration via, for example, oral or parenteral route.

The pharmaceutical composition described in the present application may be present in a unit dosage form containing a predetermined amount of active ingredient per unit dosage. Such a unit may contain 0.001 to 1000 mg, for example, 0.05 mg, 0.1 mg, 0.5 mg, 1 mg, 10 mg, 20 mg, 50 mg, 80 mg, 100 mg, 150 mg, 200 mg, 250 mg, 300 mg, 500 mg, 750 mg or 1000 mg of the compound of the present application, depending on the disease to be treated, the route of administration, and the age, weight and symptoms of subject, or the pharmaceutical composition may be present in a unit dosage form containing a predetermined amount of active ingredient per unit dosage. In another embodiment, the unit dosage compositions are those containing active ingredient in the daily dose or sub-dose or appropriate fraction thereof as described herein. In addition, this pharmaceutical composition may be prepared by any method well known to those skilled in the art.

Definition of Terms

The terms used in the description of the present application herein are only for describing specific embodiments and are not intended to limit the present application. Generally, the various terms and phrases used herein have the meaning generally understood by those skilled in the art. Even so, more detailed descriptions and explanations of these terms and phrases are still provided here, and when the terms and phrases mentioned are inconsistent with their known meanings, the meanings stated herein shall prevail.

As used herein, the term "chain alkyl" refers to a monovalent saturated hydrocarbon chain having a specified number of carbon atoms. For example, a $C_1$ to $C_5$ chain alkyl refers to an alkyl having 1 to 5 carbon atoms. The chain alkyl may be linear or branched. In some embodiments, the branched alkyl may have one, two or three branches. Exemplary chain alkyl includes, but is not limited to, methyl, methylethyl, ethyl, propyl (including n-propyl and isopropyl), methylpropyl, butyl (including n-butyl, isobutyl and tert-butyl), pentyl (including n-pentyl, isopentyl and neopentyl).

As used herein, the term "cycloalkyl" refers to a saturated cyclic hydrocarbonyl having 3 to 6 carbon atoms and having a monocyclic or bicyclic or fused polycyclic structure (including fused and bridged ring systems). For example, $C_3$ to $C_6$ cycloalkyl refers to a cycloalkyl group having 3 to 6 carbon atoms. Typical examples of "cycloalkyl" include, but are not limited to, monocyclic structures such as cyclopropyl, cyclobutyl, cyclopentyl, and cyclohexyl.

As used herein, the unit "M" represents mol/L, "µM" represents µmol/L, and "nM" represents nmol/L.

As used herein, the unit "eq" represents equivalent, that is, a molar ratio to the starting reaction material.

As used herein, the term "subject" refers to a mammalian subject (e.g., dog, cat, horse, cow, sheep, goat, monkey, etc.) and a human subject, including male or female subject, including newborn, infant, juvenile, adolescent, adult, and elderly subject, and also including various races and ethnicities, including, but not limited to, whites, blacks, Asians, American Indians, and Hispanics.

As used herein, the term "pharmaceutically acceptable salt" refers to a salt that retains the desired biological activity of the target compound and exhibits minimal undesirable toxicological effect. These pharmaceutically acceptable salts can be prepared in situ during the final isolation and purification process of the compound or by reacting the purified compound in its free acid or free base form with a suitable base or acid, respectively.

As used herein, the "therapeutically effective amount" of the compound of the present application or other pharmaceutically active agent refers to an amount within the scope of reasonable medical judgment, which is sufficient to treat or prevent a disease of patient but is low enough to avoid a serious side effect (at a reasonable benefit/risk ratio). The therapeutically effective amount of the compound may vary upon the specific compound selected (for example, considering the potency, effectiveness and half-life of the compound), the chosen route of administration, the disease to be treated; the severity of the disease to be treated, the age, size, weight and physical disease of the patient being treated, the medical history of the patient being treated, duration of treatment; nature of concurrent therapy; desired therapeutic effect and similar factors, but can still be routinely determined by those skilled in the art.

In addition, it should be pointed out that the dosage and usage method of the compound of the present application depend on many factors, including the age, weight, gender, natural health status, nutritional status of patient, the active strength of compound, the time of administration, metabolic rate, severity of disease, and the subjective judgment of the physician in charge of diagnosis and treatment. The preferred dosage is between 0.001 to 1000 mg/kg body weight/day. The dosage is administered in a single dose per day or in several sub-doses per day, for example 2, 3, 4, 5 or 6 doses per day. Alternatively, the administration may be performed intermittently, for example, once every other day, once a week, or once a month. The therapeutically effective amount of the salt or solvate can be determined as the ratio of the therapeutically effective amount of the compound represented by Formula (I) itself.

As used herein, the term "compound" refers to the compound represented by Formula I as defined above, which may be in any form, including various stereoisomers, any salt or non-salt form (for example, as a free acid or free base form, or as a salt, especially its pharmaceutically acceptable salt) and any physical form thereof (e.g., including non-solid form (e.g., liquid or semi-solid form) and solid form (e.g., amorphous or crystalline form, specific polymorphic forms, solvate forms, including hydrate forms (e.g., mono-, di-, and hemi-hydrates), and mixtures of various forms.

If the chemical name of the compound herein is inconsistent with its chemical structural formula, the chemical structural formula shall prevail.

Compared with the prior art, the present application has the following technical effects:

1. The present application provides a new type of Rho kinase inhibitor, which promotes the expression of endothelin in endothelial cells, the expression of prostacyclin, the synthesis and secretion of vasorelaxation factor NO, and the Rho kinase inhibitor of the present application can promote the expression of prostacyclin regardless of the high, medium and low doses.

2. The $IC_{50}$ values of the Rho kinase inhibitors of the present application are all higher than 80 μM, showing lower toxicity and better safety.

3. The method for preparing the Rho kinase inhibitor of the present application uses cheap and easily available chemical products as starting materials, and each step of the synthesis has a high yield, therefore, its production cost is lower and it is more suitable for industrial production.

BRIEF DESCRIPTION OF THE DRAWINGS

The drawings described herein are used to provide a further understanding of the present application and constitute a part of the present application. The exemplary examples and descriptions thereof in the present application are used to explain the present application and do not constitute an improper limitation to the present application. In the drawings.

DETAILED DESCRIPTION OF EMBODIMENTS

Figure 1:
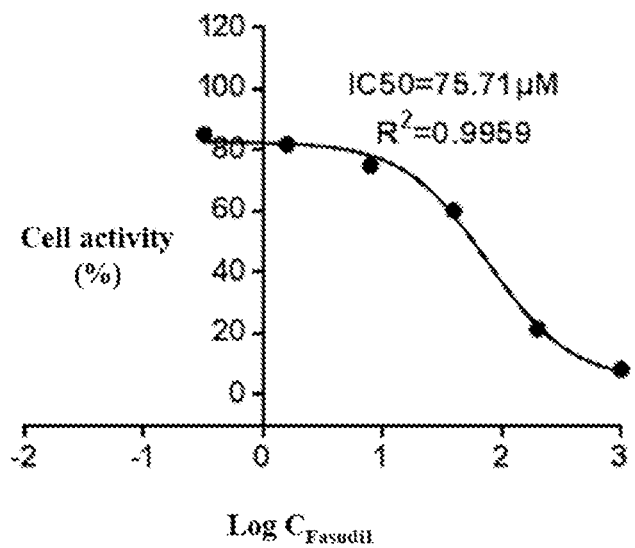
FIG. 1 shows the inhibitor concentration-viability curve of Fasudil hydrochloride.

The Rho kinase inhibitor of the present application and its preparation method and application will be described below with reference to the combination of drawings and examples. It should be understood that these examples are only used to explain the present application and not to limit the scope of the present application. It should also be understood that after reading the contents of the present application, those skilled in the art may make various changes or modifications to the present application, and these equivalent forms also fall within the scope defined by the appended claims of the present application.

The present application provides a Rho kinase inhibitor, which is a compound represented by Formula I, a stereoisomer thereof or a pharmaceutically acceptable salt thereof:

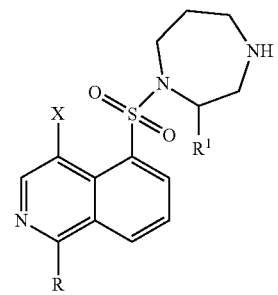

Formula I wherein, X is hydrogen, halogen (for example, halogen is fluorine, chlorine, bromine, or iodine), $C_1$ to $C_5$ chain alkyl ($C_1$ to $C_5$ chain alkyl includes linear or branched alkyl, and exemplarily is methyl, ethyl, n-propyl, isopropyl, n-butyl, isobutyl, tert-butyl, or n-pentyl, etc.), $C_3$ to $C_6$ cycloalkyl ($C_3$ to $C_6$ cycloalkyl includes substituted cycloalkyl or non-substituted cycloalkyl, and exemplarily is cyclopropyl, cyclobutyl,

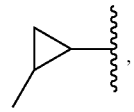 [SMILES: *C1CC1C]

cyclopentyl, or cyclohexyl, etc.), benzyl, phenyl, methoxy, ethoxy, propoxy, methylamino, ethylamino, propylamino,

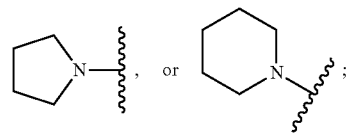

R is hydrogen, hydroxyl, $CH_3(CH_2)_mO-$, $CH_3(CH_2)_nCOO-$ or $HCO-$; m and n are each independently 0, 1, 2, 3; exemplarily, $CH_3(CH_2)_mO-$ is $CH_3O-$, $CH_3CH_2O-$, $CH_3(CH_2)_2O-$, $CH_3(CH_2)_3O-$, or $CH_3(CH_2)_4O-$; exemplarily, $CH_3(CH_2)_nCOO-$ is $CH_3COO-$, $CH_3CH_2COO-$, $CH_3(CH_2)_2COO-$, or $CH_3(CH_2)_3COO-$;

$R^1$ is hydrogen, $C_1$ to $C_5$ chain alkyl (for example, $C_1$ to $C_5$ chain alkyl includes straight chain alkyl or branched chain alkyl, and exemplarily is methyl, ethyl, n-propyl, isopropyl, n-butyl, isobutyl, tert-butyl, or n-pentyl, etc.), or $C_3$ to $C_6$ cycloalkyl ($C_3$ to $C_6$ cycloalkyl includes substituted cycloalkyl or non-substituted cycloalkyl, and exemplarily is cyclopropyl, cyclobutyl,

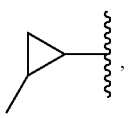

cyclopentyl, or cyclohexyl, etc.);

and the three substituents X, R and $R^1$ are not hydrogen at the same time.

Preferably, when $R^1$ is methyl, the substituents X and R are not hydrogen at the same time.

Exemplarily, the Rho kinase inhibitor is 4-cyclopropyl-5-((2-methyl-1,4-diazacycloheptan-1-yl)sulfonyl)isoquinolin-1-ol; 4-cyclopropyl-1-methoxy-5-((2-methyl-1,4-diazacycloheptan-1-yl)sulfonyl)isoquinoline; 5-((2-cyclopropyl-1,4-diazacycloheptan-1-yl)sulfonyl)-4-fluoroisoquinolin-1-ol; 5-((2-cyclopropyl-1,4-diazacycloheptan-1-yl)sulfonyl)-4-fluoroisoquinoline; 5-((2-methyl-1,4-diazacycloheptan-1-yl)sulfonyl)isoquinoline-1-ol; 1-methoxy-5-((2-methyl-1,4-diazacycloheptan-1-yl)sulfonyl)isoquinoline; 4-fluoro-5-((2-methyl-1,4-diazacycloheptan-1-yl)sulfonyl)isoquinolin-1-ol; 4-fluoro-1-methoxy-5-((2-methyl-1,4-diazacycloheptan-1-yl)sulfonyl)isoquinoline; 4-chloro-5-((2-methyl-1,4-diazacycloheptan-1-yl)sulfonyl)isoquinolin-1-ol; 4-chloro-5-((2-methyl-1,4-diazacycloheptan-1-yl)sulfonyl)isoquinoline; 5-((2-isopropyl-1,4-diazacycloheptan-1-yl)sulfonyl)isoquinolin-1-ol; 5-((2-isopropyl-1,4-diazacycloheptan-1-yl)sulfonyl)-1-methoxyisoquinoline; 5-((2-n-butyl-1,4-diazacycloheptan-1-yl)sulfonyl)isoquinolin-1-ol; or 5-((2-n-butyl-1,4-diazacycloheptan-1-yl)sulfonyl)-1-methoxyisoquinoline.

Further, the configuration of the compound represented by Formula I is R configuration.

Exemplarily, the Rho kinase inhibitor is (R)-4-cyclopropyl-5-((2-methyl-1,4-diazacycloheptan-1-yl)sulfonyl)isoquinoline-1-ol; (R)-4-cyclopropyl-1-methoxy-5-((2-methyl-1,4-diazacycloheptan-1-yl)sulfonyl)isoquinoline; (R)-5-((2-cyclopropyl-1,4-diazacycloheptan-1-yl)sulfonyl)-4-fluoroisoquinolin-1-ol; (R)-5-((2-cyclopropyl-1,4-diazacycloheptan-1-yl)sulfonyl)-4-fluoroisoquinoline; (R)-5-((2-methyl-1,4-diazacycloheptan-1-yl)sulfonyl)isoquinolin-1-ol; (R)-1-methoxy-5-((2-methyl-1,4-diazacycloheptan-1-yl)sulfonyl)isoquinoline; (R)-5-((2-methyl-1,4-diazacycloheptan-1-yl)sulfonyl)isoquinoline; (R)-4-fluoro-5-((2-methyl-1,4-diazacycloheptan-1-yl)sulfonyl)isoquinolin-1-ol; (R)-4-fluoro-1-methoxy-5-((2-methyl-1,4-diazacycloheptan-1-yl)sulfonyl)isoquinoline; (R)-4-chloro-5-((2-methyl-1,4-diazacycloheptan-1-yl)sulfonyl)isoquinolin-1-ol; (R)-4-chloro-5-((2-methyl-1,4-diazacycloheptan-1-yl)sulfonyl)isoquinoline; (R)-5-((2-isopropyl-1,4-diazacycloheptan-1-yl)sulfonyl)isoquinolin-1-ol; (R)-5-((2-isopropyl-1,4-diazacycloheptan-1-yl)sulfonyl)-1-methoxyisoquine; (R)-5-((2-n-butyl-1,4-diazacycloheptan-1-yl)sulfonyl)isoquinolin-1-ol; or (R)-5-((2-n-butyl-1,4-diazacycloheptan-1-yl)sulfonyl)-1-methoxyisoquinoline.

Further, the pharmaceutically acceptable salt of the compound represented by Formula I is any one salt selected from the group consisting of sulfate, hydrochloride, nitrate, phosphate, hydrobromide, acetate, formate, methanesulfonate, trifluoroacetate, maleate, tartrate, succinate, fumarate, citrate, benzenesulfonate, benzoate, lactate, malate, and amino acid salt; in which, the amino acid salt is preferably aspartate, glutamate, glycinate, alaninate, valinate, leucinate, isoleucinate, phenylalaninate, prolinate, tryptophanate, serinate, tyrosinate, cysteinate, methioninate, asparaginate, glutaminate, or threoninate. It should be understood that the pharmaceutically acceptable salt of the compound represented by Formula I also includes the pharmaceutically acceptable salt of the optical isomer of the compound represented by Formula I, and exemplarily is a pharmaceutically acceptable salt of the R configuration optical isomer of the compound represented by Formula I.

Exemplarily, the Rho kinase inhibitor is 4-cyclopropyl-5-((2-methyl-1,4-diazacycloheptan-1-yl)sulfonyl)isoquinolin-1-ol formate; 4-cyclopropyl-1-methoxy-5-((2-methyl-1,4-diazacycloheptan-1-yl)sulfonyl)isoquinoline hydrochloride; 5-((2-cyclopropyl-1,4-diazacycloheptan-1-yl)sulfonyl)-4-fluoroisoquinolin-1-ol sulfate; 5-((2-cyclopropyl-1,4-diazacycloheptan-1-yl)sulfonyl)-4-fluoroisoquinoline hydrochloride; 5-((2-methyl-1,4-diazacycloheptan-1-yl)sulfonyl)isoquinolin-1-ol hydrochloride; 1-methoxy-5-((2-methyl-1,4-diazacycloheptan-1-yl)sulfonyl)isoquinoline hydrochloride; 5-((2-methyl-1,4-diazacycloheptan-1-yl)sulfonyl)isoquinoline hydrochloride; 4-fluoro-5-((2-methyl-1,4-diazacycloheptan-1-yl)sulfonyl)isoquinolin-1-ol trifluoroacetate; 4-fluoro-1-methoxy-5-((2-methyl-1,4-diazacycloheptan-1-yl)sulfonyl)isoquinoline formate; 4-chloro-5-((2-methyl-1,4-diazacycloheptan-1-yl)sulfonyl)isoquinolin-1-ol sulfate; 4-chloro-5-((2-methyl-1,4-diazacycloheptan-1-yl)sulfonyl)isoquinoline methanesulfonate; 5-((2-isopropyl-1,4-diazacycloheptan-1-yl)sulfonyl)isoquinolin-1-ol hydrochloride; 5-((2-isopropyl-1,4-diazacycloheptan-1-yl)sulfonyl)-1-methoxyisoquinoline hydrochloride; 5-((2-n-butyl-1,4-diazacycloheptan-1-yl)sulfonyl)isoquinolin-1-ol hydrochloride; 5-((2-n-butyl-1,4-diazacycloheptan-1-yl)sulfonyl)-1-methoxyisoquinoline hydrochloride; (R)-4-cyclopropyl-5-((2-methyl-1,4-diazacycloheptan-1-yl)sulfonyl)isoquinolin-1-ol formate; (R)-4-cyclopropyl-1-methoxy-5-((2-methyl-1,4-diazacycloheptan-1-yl)sulfonyl)isoquinoline hydrochloride; (R)-5-((2-cyclopropyl-1,4-diazacycloheptan-1-yl)sulfonyl)-4-fluoroisoquinolin-1-ol sulfate; (R)-5-((2-cyclopropyl-1,4-diazacycloheptan-1-yl)sulfonyl)-4-fluoroisoquinoline hydrochloride; (R)-5-((2-methyl-1,4-diazacycloheptan-1-yl)sulfonyl)isoquinolin-1-ol hydrochloride; (R)-1-methoxy-5-((2-methyl-1,4-diazacycloheptan-1-yl)sulfonyl)isoquinoline hydrochloride; (R)-5-((2-methyl-1,4-diazacycloheptan-1-yl)sulfonyl)isoquinoline hydrochloride; (R)-4-fluoro-5-((2-methyl-1,4-diazacycloheptan-1-yl)sulfonyl)isoquinoline-1-ol trifluoroacetate; (R)-4-fluoro-1-methoxy-5-((2-methyl-1,4-diazacycloheptan-1-yl)sulfonyl)isoquinoline formate; (R)-4-chloro-5-((2-methyl-1,4-diazacycloheptan-1-yl)sulfonyl)isoquinolin-1-ol sulfate; (R)-4-chloro-5-((2-methyl-1,4-diazacycloheptan-1-yl)sulfonyl)isoquinoline methanesulfonate; (R)-5-((2-isopropyl-1,4-diazacycloheptan-1-yl)sulfonyl)isoquinolin-1-ol hydrochloride; (R)-5-((2-isopropyl-1,4-diazacycloheptan-1-yl)sulfonyl)-1-methoxyisoquinoline hydrochloride; (R)-5-((2-n-butyl-1,4-diazacycloheptan-1-yl)sulfonyl)isoquinolin-1-ol hydrochloride; or (R)-5-((2-n-butyl-1,4-diazacycloheptan-1-yl)sulfonyl)-1-methoxyisoquinoline hydrochloride.

The method for preparing the Rho kinase inhibitor of the present application is as follows, the compound represented by the Formula I is prepared from a compound represented by Formula II through a deprotection reaction;

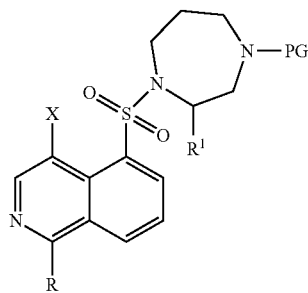

Formula II wherein, X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino,

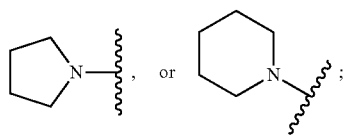 [SMILES: *N1CCCC1 ; *N1CCCCC1]

R is hydrogen, hydroxyl, $CH_3(CH_2)_mO$—, $CH_3(CH_2)_nCOO$— or HCO—; m and n are each independently 0, 1, 2, 3;

$R^1$ is hydrogen, $C_1$ to $C_5$ chain alkyl, or $C_3$ to $C_6$ cycloalkyl;

and the three substituents X, R and $R^1$ are not hydrogen at the same time;

PG is tert-butoxycarbonyl (Boc-) or benzyloxycarbonyl (Cbz-);

Exemplarily, when PG is tert-butoxycarbonyl (Boc-), the deprotection reaction is performed under the condition of hydrogen chloride/ethyl acetate solution (HCl(g)/EtOAc), hydrogen chloride/methanol solution (HCl(g)/CH$_3$OH), hydrogen chloride/ethanol solution (HCl(g)/EtOH), hydrogen chloride/dioxane solution (HCl(g)/Dioxane) or trifluoroacetic acid, etc.; when PG is benzyloxycarbonyl (Cbz-), the deprotection reaction is performed under the condition of $H_2$/Pd—C, $H_2$/Pt—C, $H_2$/Pd(OH)$_2$—C, or trifluoroacetic acid, etc.

Further, the compound represented by Formula II is prepared by a cyclization reaction of a compound represented by Formula III;

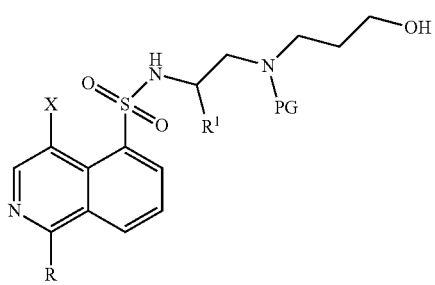

Formula III wherein, X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino,

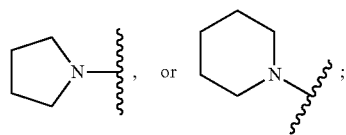 [SMILES: *N1CCCC1 ; *N1CCCCC1]

R is hydrogen, hydroxyl, $CH_3(CH_2)_mO$—, $CH_3(CH_2)_nCOO$— or HCO—; m and n are each independently 0, 1, 2, 3;

$R^1$ is hydrogen, $C_1$ to $C_5$ chain alkyl, or $C_3$ to $C_6$ cycloalkyl;

and the three substituents X, R and $R^1$ are not hydrogen at the same time;

PG is tert-butoxycarbonyl (Boc-) or benzyloxycarbonyl (Cbz-);

exemplarily, the cyclization reaction is Mitsunobu reaction, and the reaction conditions are triphenylphosphine (PPh3), diisopropyl azodicarboxylate (DIAD), or triphenylphosphine (PPh3), diethyl azodicarboxylate (DEAD).

Further, the compound represented by Formula III is prepared by a deprotection reaction of a compound represented by Formula IV;

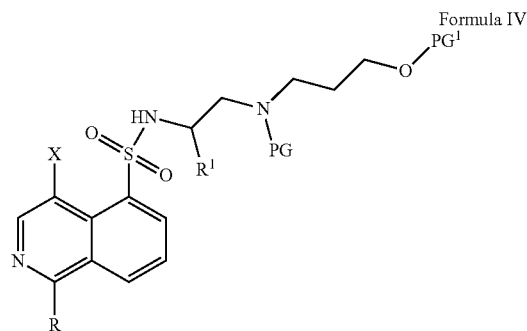

Formula IV wherein, X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino,

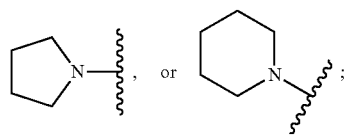 [SMILES: *N1CCCC1 ; *N1CCCCC1]

R is hydrogen, hydroxyl, $CH_3(CH_2)_mO$—, $CH_3(CH_2)_nCOO$— or HCO—; m and n are each independently 0, 1, 2, 3;

$R^1$ is hydrogen, $C_1$ to $C_5$ chain alkyl, or $C_3$ to $C_6$ cycloalkyl;

and the three substituents X, R and $R^1$ are not hydrogen at the same time;

PG is tert-butoxycarbonyl (Boc-) or benzyloxycarbonyl (Cbz-);

$PG^1$ is tert-butyldimethylsilyl (TBS-), or trimethylsilyl (TMS-), etc.;

exemplarily, the reagent of the deprotection reaction is TBAF.

Further, the compound represented by Formula IV is prepared by reacting a compound represented by Formula V with a compound represented by Formula VI;

Formula V

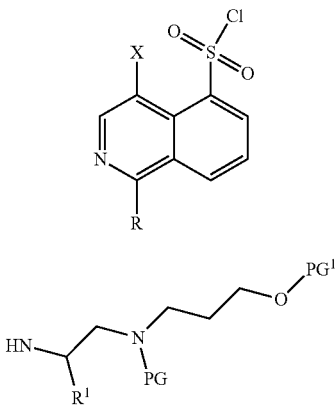

Formula VI wherein, X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino,

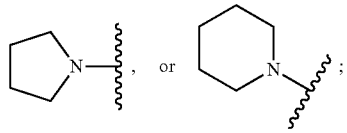 [SMILES: *N1CCCC1 ; *N1CCCCC1]

R is hydrogen, hydroxyl, $CH_3(CH_2)_mO—$, $CH_3(CH_2)_nCOO—$ or $HCO—$; m and n are each independently 0, 1, 2, 3;
$R^1$ is hydrogen, $C_1$ to $C_5$ chain alkyl, or $C_3$ to $C_6$ cycloalkyl;
and the three substituents X, R and $R^1$ are not hydrogen at the same time;
PG is tert-butoxycarbonyl (Boc-) or benzyloxycarbonyl (Cbz-);
$PG^1$ is tert-butyldimethylsilyl (TBS-), trimethylsilyl (TMS-), etc.

Further, the compound represented by Formula V is prepared by reacting a compound represented by Formula VII with chlorosulfonic acid;

Formula VII

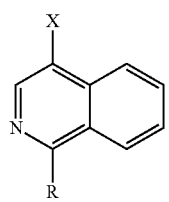

wherein, X is hydrogen, halogen, $C_1$ to $C_5$ chain alkyl, $C_3$ to $C_6$ cycloalkyl, benzyl, phenyl, methoxy, ethoxy, propoxy, methylamino, ethylamino, propylamino, R is hydrogen, hydroxyl, $CH_3(CH_2)_mO—$, $CH_3(CH_2)_nCOO—$ or $HCO—$; m and n are each independently 0, 1, 2, 3;
and the three substituents X, R and $R^1$ are not hydrogen at the same time.

If specific conditions are not indicated in the following examples, they shall be carried out in accordance with conventional conditions. The reagents or instruments used without giving manufacturers are all conventional products that are commercially available.

Example 1: Preparation of 4-cyclopropyl-5-((2-methyl-1,4-diazacycloheptan-1-yl)sulfonyl) isoquinolin-1-ol, named as YK1600-1, with the structural formula of

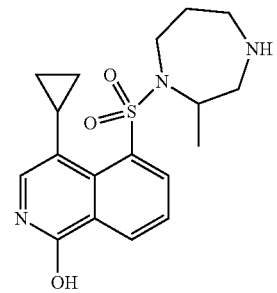 [SMILES: CC1CNCCCN1S(=O)(=O)c1cccc2c(O)ncc(C3CC3)c12]

(1) Preparation of Intermediate with synthetic scheme as follows:

50 g of 2-aminopropan-1-ol was weighed, and dissolved in 250 mL of dichloromethane solution, then benzyl chloroformate (1.0 eq) and triethylamine (3.0eq) were added at 5° C., and then the reaction was carried out under stirring at 15° C. for 5 hours. The resulting reaction solution was extracted with dichloromethane three times, the resulting organic phases were combined and distilled under reduced pressure to obtain a concentrate. The concentrate was separated by column chromatography to obtain a yellow solid benzyl (1-hydroxypropylpropan-2)carbamate (Compound 2).

50 g of benzyl (1-hydroxypropylpropan-2)carbamate and 300 mL of dichloromethane were weighed, then methanesulfonyl chloride (1.05eq) and triethylamine (3.0eq) were added at 15° C., and then the reaction was carried out under stirring at 15° C. for 3 hours. The resulting reaction solution was extracted three times with dichloromethane-saturated brine (the volume ratio of dichloromethane to saturated brine was 1:2), the resulting organic phases were combined and distilled under reduced pressure to obtain a concentrate. The concentrate was purified by a normal phase silica gel column, the purified liquid was collected and distilled under reduced pressure to obtain propyl 2-((benzyloxy)carbonyl) amino)methanesulfonate (Compound 3).

63 g of propyl 2-((benzyloxy)carbonyl)amino)methanesulfonate was weighed, and dissolved in 770 mL of tetrahydrofuran, then 3-aminopropan-1-ol (7.0eq) was added at 15° C., and then the reaction was carried out under stirring at 15° C. for 15 hours. The resulting reaction solution was concentrated under reduced pressure and then extracted three times with hydrochloric acid-ethyl acetate (the volume ratio of hydrochloric acid to ethyl acetate was 5:2). The resulting organic phases were combined, filtered, and concentrated under reduced pressure to obtain a yellow solid benzyl (1-((3-hydroxypropyl)amino)propan-2) carbamate (Compound 4).

50 g of benzyl (1-((3-hydroxypropyl)amino)propan-2) carbamate was weighed and dissolved in 400 mL of dichloromethane, then di-tert-butyl dicarbonate (1.1eq) and triethylamine (3.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 3:8), and the resulting organic phases were combined and distilled under reduced pressure to obtain a concentrate. The concentrate was purified by a normal phase silica gel column. The purified liquid was collected and distilled under reduced pressure to obtain tert-butyl (2-((benzyloxy)carbonyl)amino)propyl(3-hydroxypropyl)carbamate (Compound 5).

65 g of tert-butyl (2-((benzyloxy)carbonyl)amino)propyl (3-hydroxypropyl)carbamate was weighed and dissolved in 300 mL of dichloromethane, then tert-butyldimethylchlorosilane (1.1eq) and imidazole (2.0eq) were added at 15° C., and then the reaction was carried out under stirring at 15° C. for 15 hours. The resulting reaction liquid was extracted three times with dichloromethane. The resulting organic phases were combined and distilled under reduced pressure to obtain a yellow oily substance tert-butyl (2-((benzyloxy) carbonyl)amino)propyl)(3-((tert-butyldimethylsiloxy)propyl)carbamate (Compound 6).

77 g of tert-butyl (2-((benzyloxy)carbonyl)amino)propyl) (3-((tert-butyldimethylsiloxy) propyl)carbamate was weighed and dissolved in 400 mL of methanol, and was subjected to catalytic hydrogenation by using palladium on carbon as catalyst under stirring at 15° C. for 15 hours. The resulting reaction liquid was concentrated under reduced pressure to obtain a yellow oily substance tert-butyl (2-aminopropyl)(3-((tert-butyldimethyl)siloxy)propyl)carbamate (Compound 7).

(2) Preparation of Intermediate

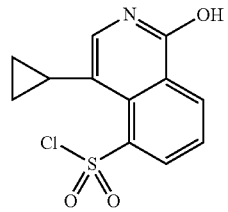 [SMILES: O=S(=O)(Cl)c1cccc2c(O)ncc(C3CC3)c12]

(1-hydroxy-4-cyclopropylisoquinoline-5-sulfonyl chloride)

1 g of 1-hydroxy-4-cyclopropylisoquinoline (obtained by the method comprising: reacting 1-methoxy-4-bromoisoquinoline with cyclopropyl Grignard reagent (2eq) under catalysis of Pd(dppf)Cl$_2$ (0.1eq) in anhydrous tetrahydrofuran at 60° C. under nitrogen conditions, and using column chromatography as post-treatment to obtain 1-methoxy-4-cyclopropylisoquinoline; reacting 1-methoxy-4-cyclopropylisoquinoline in boron tribromide in dichloromethane solution at room temperature, and using column chromatography as post-treatment to obtain 1-hydroxy-4-cyclopropylisoquinoline) was weighed and added to 10 mL of chlorosulfonic acid at 10° C.; after the addition was completed, the resulting mixture was heated to 130° C. and reacted for 12 hours, then the resulting reaction liquid was poured into ice water to form a precipitate, which was filtered, and the filter cake was dried to obtain 1.1 g of crude product 1-hydroxy-4-cyclopropylisoquinoline-5-sulfonyl chloride.

(3) Preparation of Intermediate

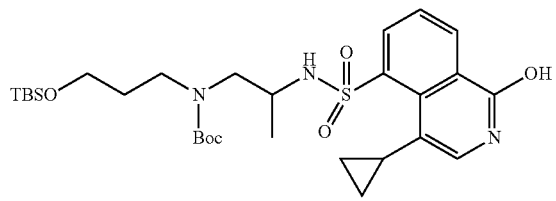 [SMILES: CC(CN(CCCO[Si](C)(C)C(C)(C)C)C(=O)OC(C)(C)C)NS(=O)(=O)c1cccc2c(O)ncc(C3CC3)c12]

1.8 g of the intermediate

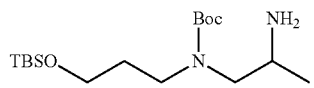 [SMILES: CC(N)CN(CCCO[Si](C)(C)C(C)(C)C)C(=O)OC(C)(C)C]

prepared in step (1) was weighed and dissolved in 20 mL of dichloromethane, then 1-hydroxy-4-cyclopropylisoquinoline-5-sulfonyl chloride prepared in step (2) and 0.8 ml of triethylamine were added and stirred at room temperature for 5 hours. The resulting reaction solution was extracted with dichloromethane-saturated brine (the volume ratio of dichloromethane to saturated brine was 6:10) three times, and the resulting organic phases were combined and distilled under reduced pressure to obtain a concentrate. The concentrate was purified by a normal phase silica gel column, the purified liquid was collected and distilled under reduced pressure to obtain 1.9 g of intermediate

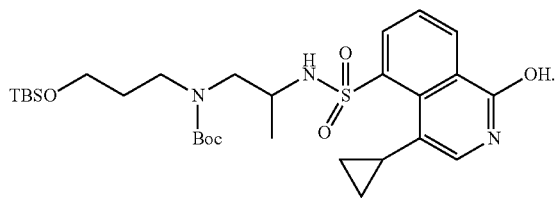 [SMILES: CC(CN(CCCO[Si](C)(C)C(C)(C)C)C(=O)OC(C)(C)C)NS(=O)(=O)c1cccc2c(O)ncc(C3CC3)c12]

The total yield of step (2) and step (3) was 65.5%; MS: [M+1]⁺=594.8.

(4) Preparation of Intermediate

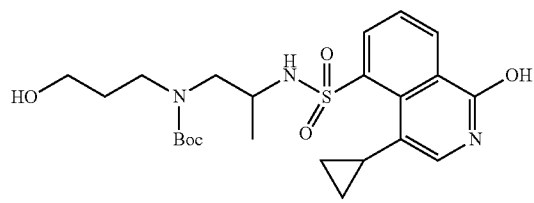 [SMILES: CC(CN(CCCO)C(=O)OC(C)(C)C)NS(=O)(=O)c1cccc2c(O)ncc(C3CC3)c12]

1.9 g of

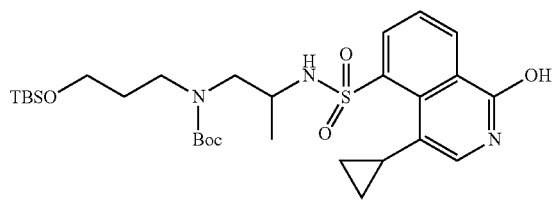 [SMILES: CC(CN(CCCO[Si](C)(C)C(C)(C)C)C(=O)OC(C)(C)C)NS(=O)(=O)c1cccc2c(O)ncc(C3CC3)c12]

prepared in step (3) was dissolved in 20 mL of tetrahydrofuran, then 1 g of TBAF (tetrabutylammonium fluoride) was added and stirred at room temperature for 12 hours, and the resulting reaction solution was extracted with dichloromethane-saturated brine (the volume ratio of dichloromethane to saturated brine was 6:10) three times. The resulting organic phases were collected and distilled under reduced pressure to obtain a concentrate. The concentrate was purified through a reverse phase column, and the purified liquid was collected and concentrated under reduced pressure to obtain 1.3 g of intermediate

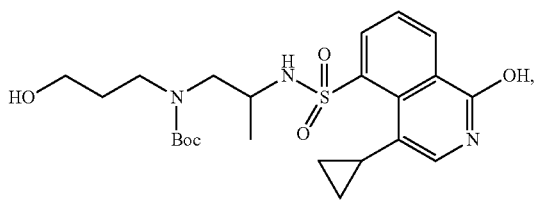 [SMILES: CC(CN(CCCO)C(=O)OC(C)(C)C)NS(=O)(=O)c1cccc2c(O)ncc(C3CC3)c12]

with a yield of 85%; MS: [M+1]⁺=480.5.

(5) Preparation of Intermediate 4-cyclopropyl-5-((N-tert-butoxycarbonyl-2-methyl-1,4-diazacycloheptan-1-yl)sulfonyl)isoquinolin-1-ol

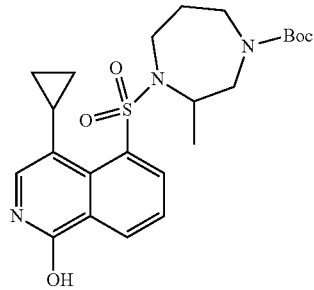 [SMILES: CC1CN(C(=O)OC(C)(C)C)CCCN1S(=O)(=O)c1cccc2c(O)ncc(C3CC3)c12]

1.3 g of

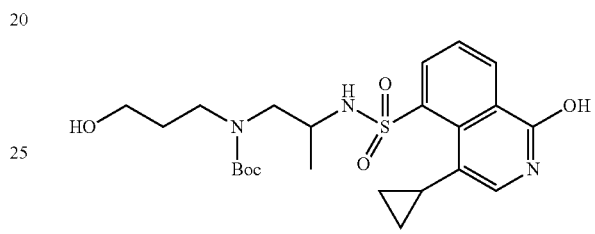

prepared in step (4) was dissolved in 20 mL of tetrahydrofuran, then 0.8 g of triphenylphosphine was added at 0° C., and 0.6 g of diisopropyl azodicarboxylate (DIAD) was added dropwise. After the addition was completed, the resulting mixture was warmed to room temperature and stirred for 12 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified through a reverse phase column, the purified liquid was collected and distilled under reduced pressure to obtain 1.09 g of intermediate 4-cyclopropyl-5-((N-tert-butoxycarbonyl-2-methyl-1,4-diazacycloheptan-1-yl)sulfonyl)isoquinolin-1-ol, with a yield of 91%; MS: [M+1]⁺=462.5.

(6) Preparation of 4-cyclopropyl-5-((2-methyl-1,4-diazacycloheptan-1-yl)sulfonyl) isoquinolin-1-ol 1.09 g of 4-cyclopropyl-5-((N-tert-butoxycarbonyl-2-methyl-1,4-diazacycloheptan-1-yl) sulfonyl)isoquinolin-1-ol prepared in step (5) was dissolved in 25 mL of 4M HCl(g) in dioxane solution, and stirred at room temperature for 2 hours, and distilled under reduced pressure to remove the solvent and obtain a concentrate. The concentrate was purified through a reverse phase column with an ammonium bicarbonate aqueous solution-methanol as mobile phase (the volume ratio of ammonium bicarbonate aqueous solution to methanol was 4:6, in which the concentration of ammonium bicarbonate aqueous solution was 10 mmol/L), the purified liquid was collected and distilled under reduced pressure to obtain 0.81 g of the target compound 4-cyclopropyl-5-((2-methyl-1,4-diazacycloheptan-1-yl)sulfonyl)isoquinolin-1-ol, with a yield of 95%; MS: [M+1]⁺=362.1; $^1$H NMR (400 MHz DMSO), 8.48 (d, 1H), 8.37 (d, 1H), 7.59 (t, 1H), 7.33 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 1.49-1.51 (m, 1H), 0.97-0.99 (m, 4H), 0.93 (d, 3H).

Example 2: Preparation of 4-cyclopropyl-1-methoxy-5-((2-methyl-1,4-diazacycloheptan-1-yl)sulfonyl)isoquinoline, named as YK1600-2, with structural formula of

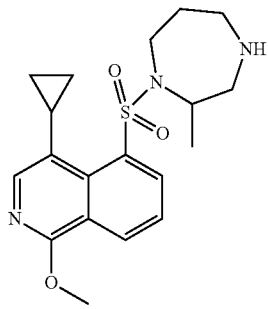 [SMILES: COc1ncc(C2CC2)c2c(S(=O)(=O)N3CCCNCC3C)cccc12]

(1) Preparation of Intermediate 1-methoxy-4-cyclopropylisoquinoline-5-sulfonyl chloride

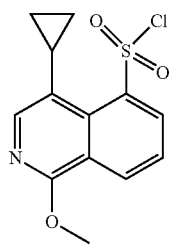 [SMILES: COc1ncc(C2CC2)c2c(S(=O)(=O)Cl)cccc12]

1 g of 1-methoxy-4-cyclopropylisoquinoline (obtained by reacting 1-methoxy-4-bromoisoquinoline with cyclopropyl Grignard reagent (2eq) under the catalysis of Pd(dppf)Cl$_2$ (0.1eq)) in anhydrous tetrahydrofuran under nitrogen conditions at 60° C., and using column chromatography separation method as post-treatment) was weighed and added to 10 mL of chlorosulfonic acid. After the addition was completed, the resulting mixture was heated to 120° C. and reacted for 12 hours, then the resulting reaction solution was poured into ice water to form a precipitate, which was filtered, and the filter cake was dried to obtain 1.05 g of crude product 1-methoxy-4-cyclopropylisoquinoline-5-sulfonyl chloride.

(2) Preparation of Intermediate

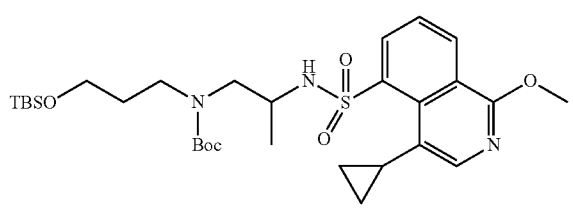 [SMILES: COc1ncc(C2CC2)c2c(S(=O)(=O)NC(C)CN(CCCO[Si](C)(C)C(C)(C)C)C(=O)OC(C)(C)C)cccc12]

1.6 g of the intermediate

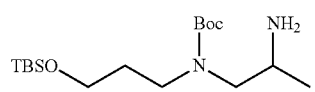 [SMILES: CC(N)CN(CCCO[Si](C)(C)C(C)(C)C)C(=O)OC(C)(C)C]

prepared in step (1) of Example 1 was weighed and dissolved in 20 mL of dichloromethane, then 1.05 g of 1-methoxy-4-cyclopropylisoquinoline-5-sulfonyl chloride prepared in step (1) of this example and 1 ml of diisopropylethylamine were added and stirred at room temperature for 5 hours. The resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified by a normal phase silica gel column, the purified liquid was collected and distilled under reduced pressure to obtain 2.1 g of intermediate

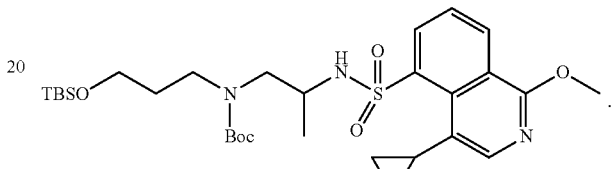

The total yield of steps (1) and (2) was 70%; MS: [M+1]$^+$ =608.8.

(3) Preparation of Intermediate

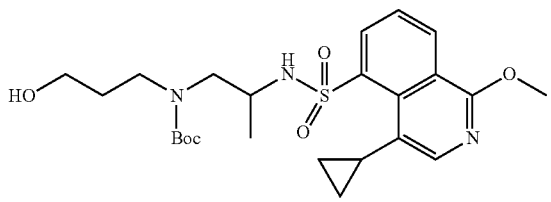 [SMILES: COc1ncc(C2CC2)c2c(S(=O)(=O)NC(C)CN(CCCO)C(=O)OC(C)(C)C)cccc12]

2.1 g of

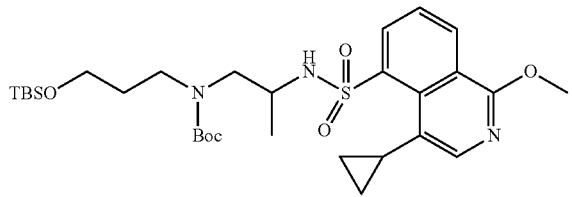 [SMILES: COc1ncc(C2CC2)c2c(S(=O)(=O)NC(C)CN(CCCO[Si](C)(C)C(C)(C)C)C(=O)OC(C)(C)C)cccc12]

prepared in step (2) was dissolved in 30 mL of tetrahydrofuran, then 1.2 g of TBAF (tetrabutylammonium fluoride) was added and stirred at room temperature for 10 hours. The resulting reaction solution was extracted with dichloromethane-saturated brine for three times, the resulting organic phases were collected and distilled under reduced pressure to obtain a concentrate. The concentrate was purified through a reverse phase column, the purified liquid was collected and concentrated under reduced pressure to obtain 1.46 g of intermediate

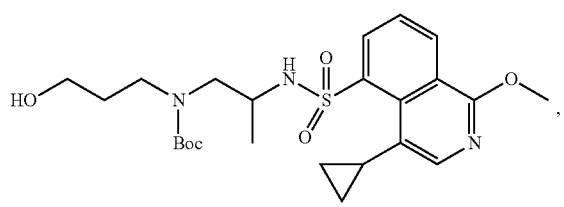 [SMILES: COc1ncc(C2CC2)c2c(S(=O)(=O)NC(C)CN(CCCO)C(=O)OC(C)(C)C)cccc12]

with a yield of 86%; MS: [M+1]$^+$=494.6.

(4) Preparation of Intermediate

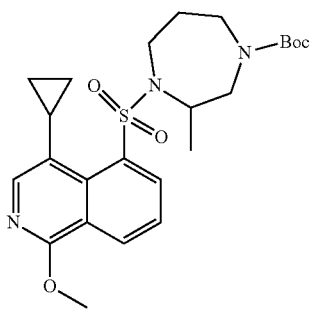 [SMILES: COc1ncc(C2CC2)c2c(S(=O)(=O)N3CCCN(C(=O)OC(C)(C)C)CC3C)cccc12]

(4-cyclopropyl-1-methoxy-5-((N-tert-butoxycarbonyl-2-methyl-1,4-diazacycloheptan-1-yl)sulfonyl)isoquinoline)

1.46 g of

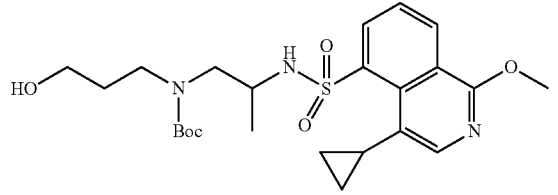 [SMILES: COc1ncc(C2CC2)c2c(S(=O)(=O)NC(C)CN(CCCO)C(=O)OC(C)(C)C)cccc12]

prepared in step (3) was dissolved in 20 mL of tetrahydrofuran, then 0.8 g of triphenylphosphine was added at 0° C., and 0.65 g of DIAD was added dropwise. After the addition was completed, the resulting mixture was warmed to room temperature and stirred for 10 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified through a reverse phase column, and the purified liquid was collected and distilled under reduced pressure to obtain 1.25 g of intermediate 4-cyclopropyl-1-methoxy-5-((N-tert-butoxycarbonyl-2-methyl-1,4-diazacycloheptan-1-yl)sulfonyl)isoquinoline, with a yield of 89%; MS: [M+1]$^+$=476.6.

(5) Preparation of the Target Compound 4-cyclopropyl-1-methoxy-5-((2-methyl-1,4-diazacycloheptan-1-yl)sulfonyl)isoquinoline 1.25 g of 4-cyclopropyl-1-methoxy-5-((N-tert-butoxycarbonyl-2-methyl-1,4-diazacycloheptan-1-yl)sulfonyl)isoquinoline prepared in step (4) was dissolved in 25 mL of 4M HCl(g) in dioxane solution, and stirred at room temperature for 1 hour, and distilled under reduced pressure to remove the solvent and obtain a concentrate. The concentrate was purified through a reverse phase column with ammonium bicarbonate aqueous solution-methanol as mobile phase (the volume ratio of ammonium bicarbonate aqueous solution to methanol was 4:6, in which the concentration of ammonium bicarbonate aqueous solution was 10 mmol/L), the purified liquid was collected and distilled under reduced pressure to obtain 0.94 g of 4-cyclopropyl-1-methoxy-5-((2-methyl-1,4-diazacycloheptan-1-yl)sulfonyl)isoquinoline, with a yield of 95%; MS: [M+1]$^+$=376.1; $^1$H NMR (400 MHz DMSO), 8.48 (d, 1H), 8.37 (d, 1H), 7.59 (t, 1H), 7.33 (d, 1H), 4.05 (s, 3H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 1.49-1.51 (m, 1H), 0.97-0.99 (m, 4H), 0.93 (d, 3H).

Example 3: Preparation of 5-((2-methyl-1,4-diazacycloheptan-1-yl)sulfonyl) isoquinolin-1-ol, named as YK1601, with structural formula of

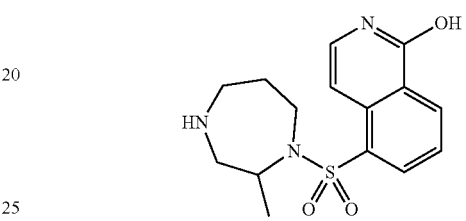

(1) Preparation of Intermediate

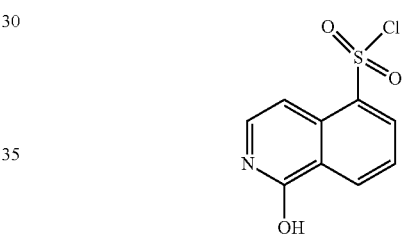

(1-hydroxyisoquinoline-5-sulfonyl chloride)

1 g of 1-hydroxy-isoquinoline was weighed and added into 10 mL of chlorosulfonic acid at 10° C. After the addition was completed, the resulting mixture was heated to 120° C. and reacted for 12 hours, then the reaction solution was poured into ice water to form a precipitate, which was filtered, and the filter cake was dried to obtain 1.58 g of crude product 1-hydroxyisoquinoline-5-sulfonyl chloride.

(2) Preparation of Intermediate

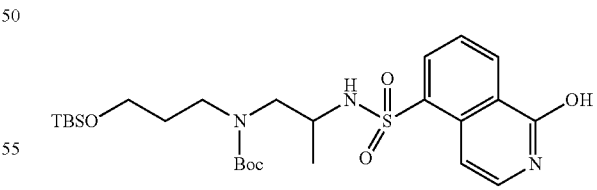

2.3 g of the intermediate

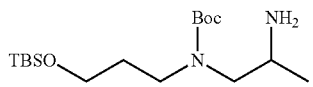 [SMILES: CC(N)CN(CCCO[Si](C)(C)C(C)(C)C)C(=O)OC(C)(C)C]

prepared in step (1) of Example 1 was weighed and dissolved in 25 mL of dichloromethane, then 1-hydroxyisoquinoline-5-sulfonyl chloride prepared in step (1) and 1 ml of triethylamine were added and stirred at room temperature for 4 hours. The resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified with a normal phase silica gel column, the purified liquid was collected and distilled under reduced pressure to obtain 2.5 g of intermediate

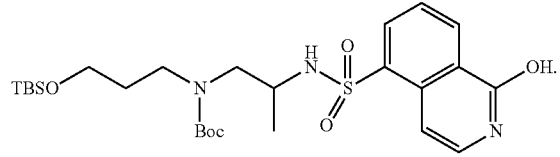 [SMILES: CC(CN(CCCO[Si](C)(C)C(C)(C)C)C(=O)OC(C)(C)C)NS(=O)(=O)c1cccc2c(O)nccc12]

The total yield of step (1) and step (2) was 66%; MS: [M+1]$^+$=554.8.

(3) Preparation of Intermediate

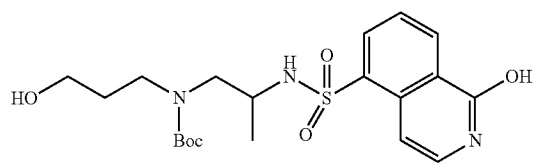 [SMILES: CC(CN(CCCO)C(=O)OC(C)(C)C)NS(=O)(=O)c1cccc2c(O)nccc12]

2.5 g of

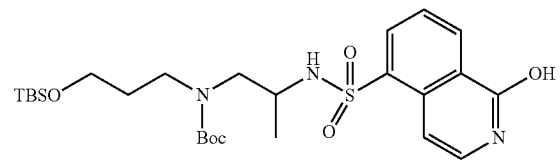 [SMILES: CC(CN(CCCO[Si](C)(C)C(C)(C)C)C(=O)OC(C)(C)C)NS(=O)(=O)c1cccc2c(O)nccc12]

prepared in step (2) was dissolved in 40 mL of tetrahydrofuran, then 1.5 g of TBAF (tetrabutylammonium fluoride) was added and stirred at room temperature for 10 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate. The concentrate was purified through a reverse phase column, the purified liquid was collected and concentrated under reduced pressure to obtain 1.6 g of intermediate

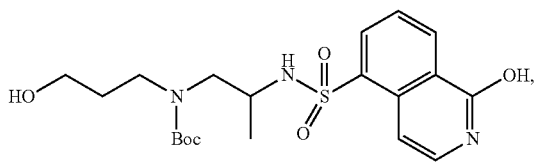 [SMILES: CC(CN(CCCO)C(=O)OC(C)(C)C)NS(=O)(=O)c1cccc2c(O)nccc12]

with a yield of 81%; MS: [M+1]$^+$=440.5.

(4) Preparation of Intermediate 5-((N-tert-butoxycarbonyl-2-methyl-1,4-diazacycloheptan-1-yl)sulfonyl)isoquinolin-1-ol

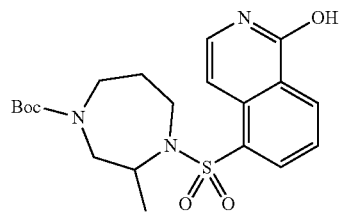 [SMILES: CC1CN(C(=O)OC(C)(C)C)CCCN1S(=O)(=O)c1cccc2c(O)nccc12]

1.6 g of

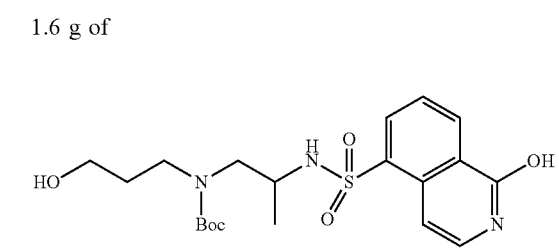

prepared in step (3) was dissolved in 30 mL of tetrahydrofuran, then 1.1 g of triphenylphosphine was added at 0° C., and 0.9 g of DIAD was added dropwise. After the addition was completed, the resulting mixture was heated to room temperature and stirred for 12 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified through a reverse phase column, the purified liquid was collected and distilled under reduced pressure to obtain 1.35 g of intermediate 5-((N-tert-butoxycarbonyl-2-methyl-1,4-diazacycloheptan-1-yl)sulfonyl)isoquinolin-1-ol, with a yield of 88%; MS: [M+1]$^+$=422.5.

(5) Preparation of Target Compound 5-((2-methyl-1,4-diazacycloheptan-1-yl) sulfonyl)isoquinolin-1-ol 1.35 g of 5-((N-tert-butoxycarbonyl-2-methyl-1,4-diazacycloheptan-1-yl)sulfonyl) isoquinolin-1-ol prepared in step (4) was dissolved in 30 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of the ammonium bicarbonate aqueous solution was 10 mmol/L) as mobile phase, the purified liquid was collected and distilled under reduced pressure to obtain 0.97 g of 5-((2-methyl-1,4-diazacycloheptan-1-yl)sulfonyl) isoquinolin-1-ol, with a yield of 94%; MS: [M+1]$^+$=322.1; $^1$H NMR (400 MHz DMSO), 8.48 (d, 1H), 8.37 (d, 1H), 7.59 (t, 1H), 7.33 (d, 1H), 7.11 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.93 (d, 3H).

Example 4: Preparation of 1-methoxy-5-((2-methyl-1,4-diazacycloheptan-1-yl)sulfonyl) isoquinoline, named as YK1602, with structural formula of

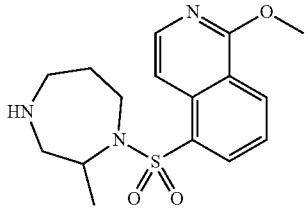 [SMILES: COc1nccc2c(S(=O)(=O)N3CCCNCC3C)cccc12]

(1) Preparation of Intermediate 1-methoxyisoquinoline-5-sulfonyl chloride

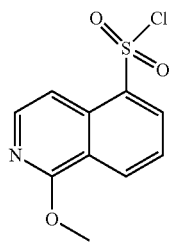

1 g of 1-methoxyisoquinoline was weighed and added into 10 mL of chlorosulfonic acid at 10° C. After the addition was completed, the resulting mixture was heated to 130° C. and reacted for 12 hours, then the resulting reaction solution was poured into ice water to form a precipitate, which was filtered, and the filter cake was dried to obtain 1.47 g of crude product 1-methoxyisoquinoline-5-sulfonyl chloride.

(2) Preparation of Intermediate Boc N

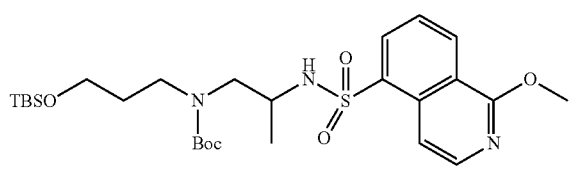 [SMILES: COc1nccc2c(S(=O)(=O)NC(C)CN(CCCO[Si](C)(C)C(C)(C)C)C(=O)OC(C)(C)C)cccc12]

2.0 g of intermediate

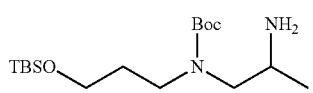 [SMILES: CC(N)CN(CCCO[Si](C)(C)C(C)(C)C)C(=O)OC(C)(C)C]

prepared in step (1) of Example 1 was dissolved in 25 mL of dichloromethane, then 1-methoxyisoquinoline-5-sulfonyl chloride prepared in step (1) and 1 mL of triethylamine were added and stirred at room temperature for 4 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified by a normal phase silica gel column, the purified liquid was collected and distilled under reduced pressure to obtain 2.39 g of intermediate

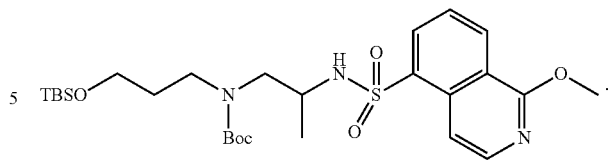

The total yield of step (1) and step (2) was 67%; MS: $[M+1]^+=568.8$.

(3) Preparation of Intermediate

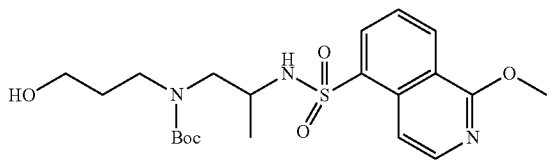 [SMILES: COc1nccc2c(S(=O)(=O)NC(C)CN(CCCO)C(=O)OC(C)(C)C)cccc12]

2.39 g of

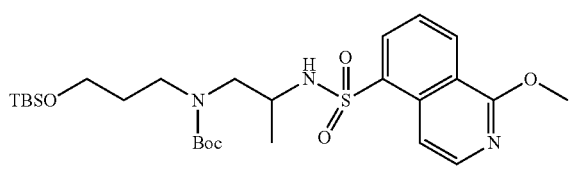 [SMILES: COc1nccc2c(S(=O)(=O)NC(C)CN(CCCO[Si](C)(C)C(C)(C)C)C(=O)OC(C)(C)C)cccc12]

prepared in step (2) was dissolved in 30 mL of tetrahydrofuran, then 1.3 g of TBAF (tetrabutylammonium fluoride) was added and stirred at room temperature for 12 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate. The concentrate was purified through a reverse phase column, the purified liquid was collected and concentrated under reduced pressure to obtain 1.6 g of intermediate

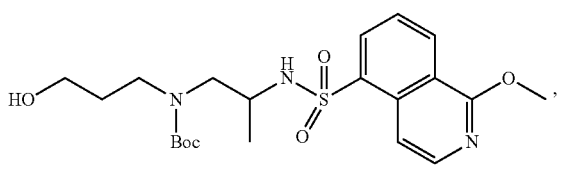 [SMILES: COc1nccc2c(S(=O)(=O)NC(C)CN(CCCO)C(=O)OC(C)(C)C)cccc12]

with a yield of 86%; MS: $[M+1]^+=454.5$.

(4) Preparation of Intermediate 1-methoxy-5-((N-tert-butoxycarbonyl-2-methyl-1,4-diazacycloheptan-1-yl)sulfonyl) isoquinoline

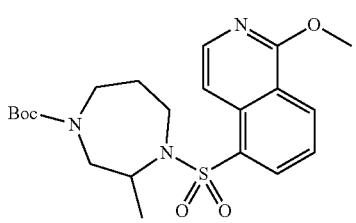 [SMILES: COc1nccc2c(S(=O)(=O)N3CCCN(C(=O)OC(C)(C)C)CC3C)cccc12]

1.6 g of

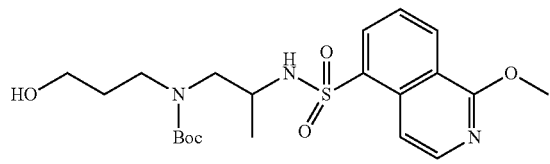 [SMILES: COc1nccc2c(S(=O)(=O)NC(C)CN(CCCO)C(=O)OC(C)(C)C)cccc12]

prepared in step (3) was dissolved in 25 mL of tetrahydrofuran, then 1.1 g of triphenylphosphine was added at 0° C., and 0.7 g of DIAD was added dropwise. After the addition was completed, the resulting mixture was warmed to room temperature and stirred for 12 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified through a reverse phase column, and the purified liquid was collected and distilled under reduced pressure to obtain 1.4 g of intermediate 1-methoxy-5-((N-tert-butoxycarbonyl-2-methyl-1,4-diazacycloheptan-1-yl)sulfonyl)isoquinoline, with a yield of 92%; MS: [M+1]$^+$=436.5.

(5) Preparation of Target Compound 1-methoxy-5-((2-methyl-1,4-diazacycloheptan-1-yl)sulfonyl)isoquinoline 1.4 g of 1-methoxy-5-((N-tert-butoxycarbyl-2-methyl-1,4-diazacycloheptan-1-yl)sulfonyl) isoquinoline prepared in step (4) was dissolved in 25 mL of 4M HCl(g) in dioxane solution, stirred at room temperature for 1 hour, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 1.03 g of 1-methoxy-5-((2-methyl-1,4-diazacycloheptan-1-yl)sulfonyl)isoquinoline, with a yield of 96%; MS: [M+1]$^+$=336.1; $^1$H NMR (400 MHz DMSO), 8.46-8.54 (m, 2H), 8.19 (d, 1H), 7.88 (d, 1H), 7.74 (t, 1H), 4.08 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 0.84 (t, 3H).

Example 5: Preparation of 5-((2-methyl-1,4-diazacycloheptan-1-yl)sulfonyl)isoquinoline, named as YK1603, with structural formula of

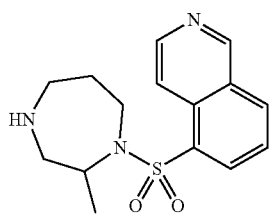 [SMILES: CC1CNCCCN1S(=O)(=O)c1cccc2cnccc12]

(1) Preparation of Intermediate

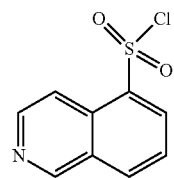 [SMILES: O=S(=O)(Cl)c1cccc2cnccc12]

(isoquinoline-5-sulfonyl chloride)

1 g of isoquinoline was weighed and added to 10 mL of chlorosulfonic acid at 10° C. After the addition was completed, the resulting mixture was heated to 130° C. and reacted for 12 hours, then the resulting reaction solution was poured into ice water to form a precipitate, which was filtered, and the filter cake was dried to obtain 1.6 g of crude product isoquinoline-5-sulfonyl chloride.

(2) Preparation of Intermediate

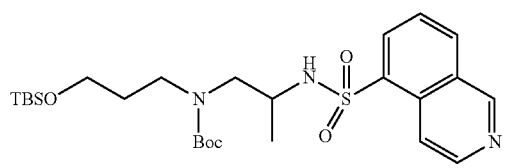 [SMILES: CC(CN(CCCO[Si](C)(C)C(C)(C)C)C(=O)OC(C)(C)C)NS(=O)(=O)c1cccc2cnccc12]

2.6 g of the intermediate

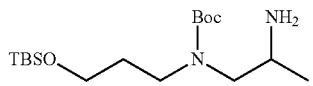 [SMILES: CC(N)CN(CCCO[Si](C)(C)C(C)(C)C)C(=O)OC(C)(C)C]

prepared in step (1) of Example 1 was weighed and dissolved in 40 mL of dichloromethane, then isoquinoline-5-sulfonyl chloride prepared in step (1) and 1 ml of triethylamine were added and stirred at room temperature for 5 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified with a normal phase silica gel column, the purified liquid was collected and distilled under reduced pressure to obtain 2.9 g of intermediate

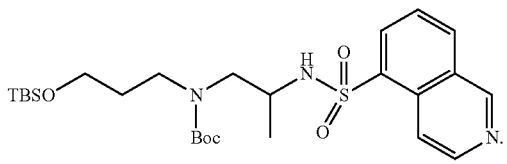 [SMILES: CC(CN(CCCO[Si](C)(C)C(C)(C)C)C(=O)OC(C)(C)C)NS(=O)(=O)c1cccc2cnccc12]

The total yield of step (1) and step (2) was 70%; MS: [M+1]$^+$=538.7.

(3) Preparation of Intermediate

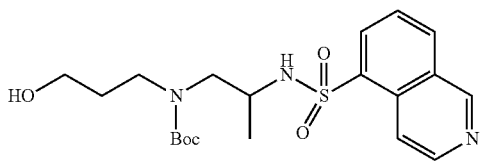 [SMILES: CC(CN(CCCO)C(=O)OC(C)(C)C)NS(=O)(=O)c1cccc2cnccc12]

2.9 g of

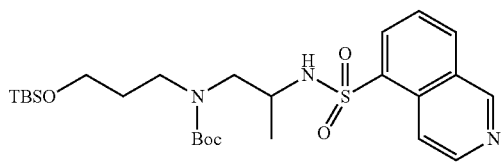 [SMILES: CC(CN(CCCO[Si](C)(C)C(C)(C)C)C(=O)OC(C)(C)C)NS(=O)(=O)c1cccc2cnccc12]

prepared in step (2) was dissolved in 50 mL of tetrahydrofuran, then 1.6 g of TBAF (tetrabutylammonium fluoride) was added and stirred at room temperature for 12 hours, the resulting reaction solution was extracted with dichloromethane-saturated brine (the volume ratio of dichloromethane to saturated brine was 6:10) three times, the resulting organic phase were collected and distilled under reduced pressure to obtain a concentrate. The concentrate was purified through a reverse phase column, the purified liquid was collected and concentrated under reduced pressure to obtain 1.96 g of intermediate

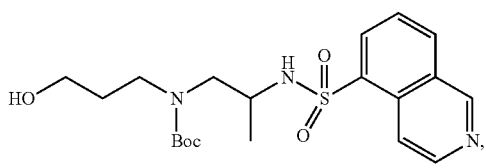 [SMILES: CC(CN(CCCO)C(=O)OC(C)(C)C)NS(=O)(=O)c1cccc2cnccc12]

with a yield of 86%; MS: [M+1]$^+$=424.5.

(4) Preparation of Intermediate 5-((N-tert-butoxycarbonyl-2-methyl-1,4-diazacycloheptan-1-yl)sulfonyl)isoquinoline

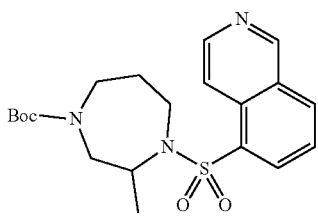 [SMILES: CC1CN(C(=O)OC(C)(C)C)CCCN1S(=O)(=O)c1cccc2cnccc12]

1.96 g of

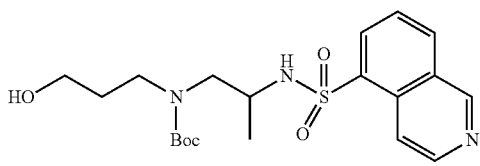 [SMILES: CC(CN(CCCO)C(=O)OC(C)(C)C)NS(=O)(=O)c1cccc2cnccc12]

prepared in step (3) was dissolved in 50 mL of tetrahydrofuran, then 1.45 g of triphenylphosphine was added at 0° C., and 1.2 g of DIAD was added dropwise. After the addition was completed, the resulting mixture was warmed to room temperature and stirred for 12 hours, the resulting reaction solution was extracted with dichloromethane-saturated brine three times, the resulting organic phases were combined and distilled under reduced pressure to obtain a concentrate. The concentrate was purified through a reverse phase column, the purified liquid was collected and distilled under reduced pressure to obtain 1.7 g of intermediate 5-((N-tert-butoxycarbonyl-2-methyl-1,4-diazacycloheptan-1-yl)sulfonyl)isoquinoline, with a yield of 91%; MS: [M+1]$^+$=406.5.

(5) Preparation of the Target Compound 5-((2-methyl-1,4-diazacycloheptan-1-yl)sulfonyl)isoquinoline 1.7 g of 5-((N-tert-butoxycarbonyl-2-methyl-1,4-diazacycloheptan-1-yl)sulfonyl) isoquinoline prepared in step (4) was dissolved in 25 mL of 4M HCl(g)/dioxane solution, stirred for 2 hours at room temperature, and then distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 1.22 g of 5-((2-methyl-1,4-diazacycloheptan-1-yl)sulfonyl)isoquinoline, with a yield of 96%; MS: [M+1]$^+$=306.1; $^1$H NMR (400 MHz DMSO), 8.89 (s, 1H), 8.48 (d, 1H), 8.37 (d, 1H), 7.59 (t, 1H), 7.33 (d, 1H), 7.11 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.93 (d, 3H).

Example 6: Preparation of 4-fluoro-5-((2-methyl-1,4-diazacycloheptan-1-yl)sulfonyl) isoquinolin-1-ol, named as YK1604, with structural formula of

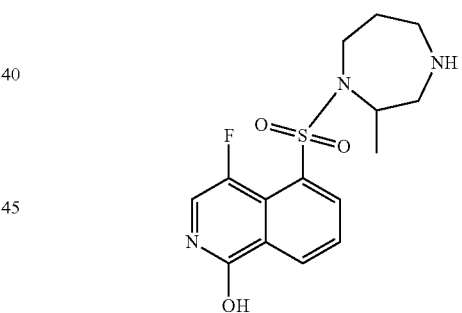

(1) Preparation of Intermediate

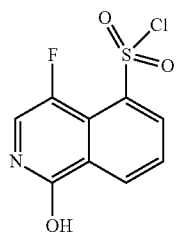

(4-fluoro-1-hydroxyisoquinoline-5-sulfonyl chloride)

1 g of 1-hydroxy-4-fluoroisoquinoline was weighed and added to 10 mL of chlorosulfonic acid at 10° C. After the addition was completed, the resulting mixture was heated to 130° C. and reacted for 12 hours, then the resulting reaction solution was poured into ice water to form a precipitate, which was filtered, and the filter cake was dried to obtain 1.1 g of crude product 4-fluoro-1-hydroxyisoquinoline-5-sulfonyl chloride.

(2) Preparation of Intermediate

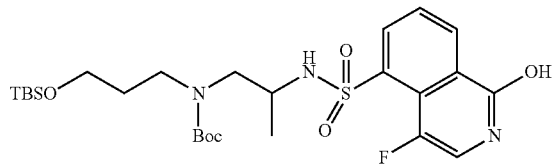

2.1 g of the intermediate

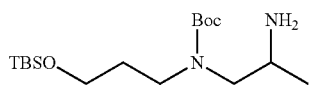 [SMILES: CC(N)CN(CCCO[Si](C)(C)C(C)(C)C)C(=O)OC(C)(C)C]

prepared in step (1) of Example 1 was weighed and dissolved in 40 mL of dichloromethane, then 4-fluoro-1-hydroxyisoquinoline-5-sulfonyl chloride prepared in step (1) and an appropriate amount of triethylamine were added and stirred at room temperature for 5 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified with a normal phase silica gel column, the purified liquid was collected and distilled under reduced pressure to obtain 2.5 g of intermediate

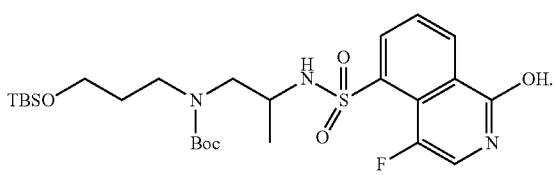 [SMILES: CC(CN(CCCO[Si](C)(C)C(C)(C)C)C(=O)OC(C)(C)C)NS(=O)(=O)c1cccc2c(O)ncc(F)c12]

The total yield of steps (1) and (2) was 71%; MS: [M+1]$^+$= 572.7.

(3) Preparation of Intermediate

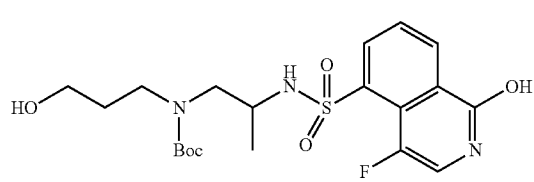

2.5 g of

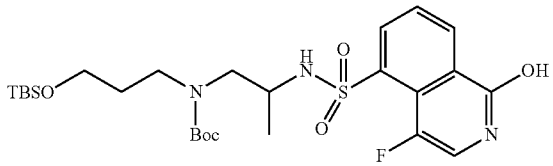

prepared in step (2) was dissolved in 30 mL of tetrahydrofuran, then 1.4 g of TBAF (tetrabutylammonium fluoride) was added and stirred at room temperature for 12 hours, the resulting reaction solution was extracted with dichloromethane-saturated brine (volume ratio was 6:10) three times, the resulting organic phases were collected and distilled under reduced pressure to obtain a concentrate. The concentrate was purified through a reverse phase column, the purified liquid was collected and concentrated under reduced pressure to obtain 1.7 g of intermediate

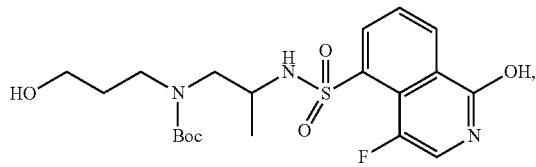 [SMILES: CC(CN(CCCO)C(=O)OC(C)(C)C)NS(=O)(=O)c1cccc2c(O)ncc(F)c12]

with a yield of 86%; MS: [M+1]$^+$=458.5.

(4) Preparation of Intermediate 4-fluoro-5-((N-tert-butoxycarbonyl-2-methyl-1,4-diazacycloheptan-1-yl)sulfonyl)isoquinolin-1-ol

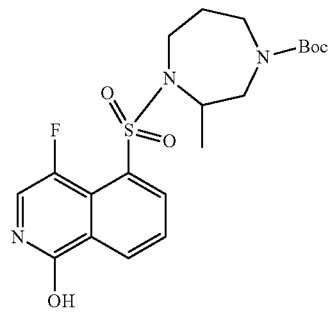 [SMILES: CC1CN(C(=O)OC(C)(C)C)CCCN1S(=O)(=O)c1cccc2c(O)ncc(F)c12]

1.7 g of

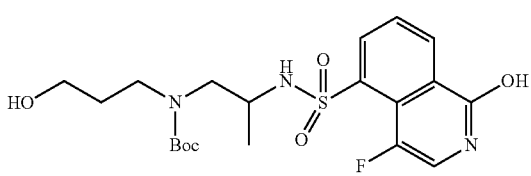

prepared in step (3) was dissolved in 30 mL of tetrahydrofuran, then 1.2 g of triphenylphosphine was added at 0° C., and 0.9 g of DIAD was added dropwise. After the addition was completed, the resulting mixture was heated to room temperature and stirred for 12 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified through a reverse phase column, the purified liquid was collected and distilled under reduced pressure to obtain 1.4 g of intermediate 4-fluoro-5-((N-tert-butoxycarbonyl-2-methyl-1,4-diazacycloheptan-1-yl)sulfonyl)isoquinolin-1-ol, with a yield of 87%; MS: [M+1]$^+$=440.5.

(5) Preparation of the Target Compound 4-fluoro-5-((2-methyl-1,4-diazacycloheptan-1-yl)sulfonyl)isoquinolin-1-ol 1.4 g of 4-fluoro-5-((N-tert-butoxycarbonyl-2-methyl-1,4-diazacycloheptan-1-yl)sulfonyl) isoquinolin-1-ol prepared in step (4) was dissolved in 25 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 1.0 g of the target compound 4-fluoro-5-((2-methyl-1,4-diazacycloheptan-1-yl)sulfonyl)isoquinolin-1-ol, with a yield of 93%; MS: [M+1]$^+$=340.1; $^1$H NMR (400 MHz DMSO), 8.48 (d, 1H), 8.37 (d, 1H), 7.59 (t, 1H), 7.33 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.93 (d, 3H).

Example 7: Preparation of 4-fluoro-1-methoxy-5-((2-methyl-1,4-diazacycloheptan-1-yl) sulfonyl)isoquinoline, named as YK1605, with structural formula of

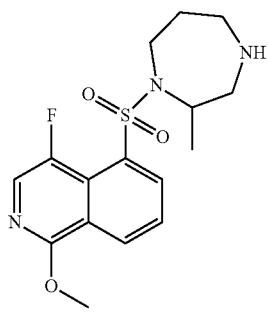 [SMILES: COc1ncc(F)c2c(S(=O)(=O)N3CCCNCC3C)cccc12]

(1) Preparation of Intermediate 1-methoxy-4-fluoroisoquinoline-5-sulfonyl chloride

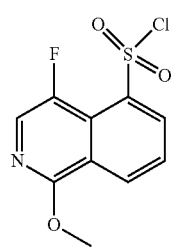

1 g of 1-methoxy-4-fluoroisoquinoline was weighed and added to 10 mL of chlorosulfonic acid at 10° C. After the addition was completed, the resulting mixture was heated to 135° C. and reacted for 12 hours, then the resulting reaction solution was poured into ice water to form a precipitate, which was filtered, and the filter cake was dried to obtain 1.6 g of crude product 1-methoxy-4-fluoroisoquinoline-5-sulfonyl chloride.

(2) Preparation of Intermediate

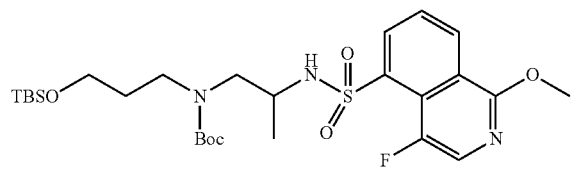 [SMILES: COc1ncc(F)c2c(S(=O)(=O)NC(C)CN(CCCO[Si](C)(C)C(C)(C)C)C(=O)OC(C)(C)C)cccc12]

2.1 g of the intermediate

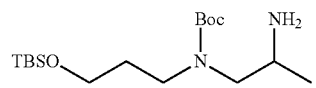 [SMILES: CC(N)CN(CCCO[Si](C)(C)C(C)(C)C)C(=O)OC(C)(C)C]

prepared in step (1) of Example 1 was weighed and dissolved in 40 mL of dichloromethane, then 1.6 g of 1-methoxy-4-fluoroisoquinoline-5-sulfonyl chloride prepared in step (1) and 1 ml of triethylamine were added and stirred at room temperature for 5 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified with a normal phase silica gel column, the purified liquid was collected and distilled under reduced pressure to obtain 2.33 g of intermediate

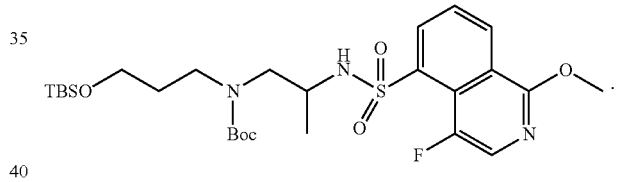

The total yield of step (1) and step (2) was 63%; MS: [M+1]$^+$=586.8.

(3) Preparation of Intermediate

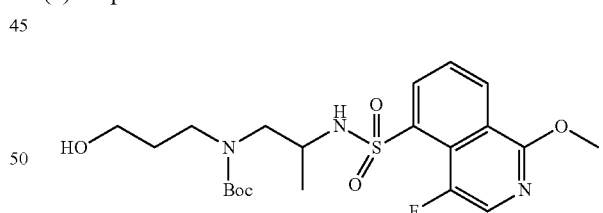

2.33 g of

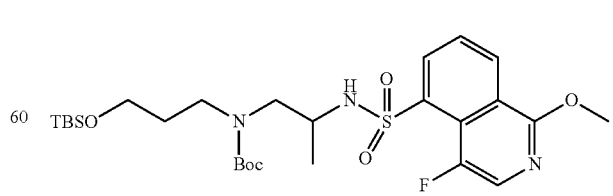

prepared in step (2) was dissolved in 30 mL of tetrahydrofuran, then 1.3 g of TBAF (tetrabutylammonium fluoride) was added and stirred at room temperature for 12 hours, the resulting reaction solution was extracted three times with dichloromethane-saturated brine (the volume ratio of dichloromethane to saturated brine was 6:10), the resulting organic phases were collected and distilled under reduced pressure to obtain a concentrate. The concentrate was purified through a reverse phase column, the purified liquid was collected and concentrated under reduced pressure to obtain 1.5 g of intermediate

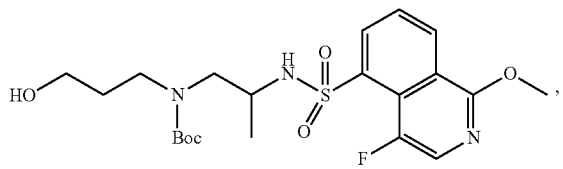 [SMILES: COc1ncc(F)c2c(S(=O)(=O)NC(C)CN(CCCO)C(=O)OC(C)(C)C)cccc12]

with a yield of 82%; MS: [M+1]⁺=472.5.

(4) Preparation of Intermediate 4-fluoro-1-methoxy-5-((N-tert-butoxycarbonyl-2-methyl-1,4-diazacycloheptan-1-yl)sulfonyl)isoquinoline

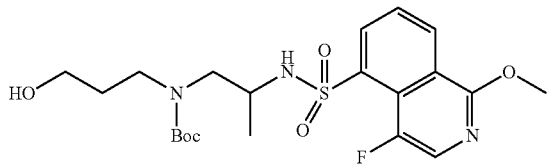 [SMILES: COc1ncc(F)c2c(S(=O)(=O)NC(C)CN(CCCO)C(=O)OC(C)(C)C)cccc12]

1.5 g of

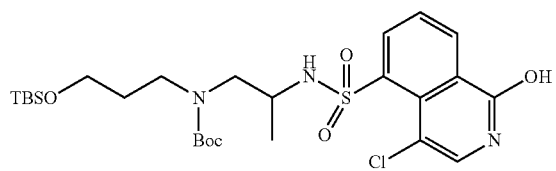

prepared in step (3) was dissolved in 30 mL of tetrahydrofuran, then 1.0 g of triphenylphosphine was added at 0° C., and 0.64 g of DIAD was added dropwise. After the addition was completed, the resulting mixture was warmed to room temperature and stirred for 12 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified through a reverse phase column, and the purified liquid was collected and distilled under reduced pressure to obtain 1.2 g of intermediate 4-fluoro-1-methoxy-5-((N-tert-butoxycarbonyl-2-methyl-1,4-diazacycloheptan-1-yl)sulfonyl)isoquinoline, with a yield of 89%; MS: [M+1]⁺=454.5.

(5) Preparation of the Target Compound 4-fluoro-1-methoxy-5-((2-methyl-1,4-diazacycloheptan-1-yl)sulfonyl) isoquinoline 1.2 g of 4-fluoro-1-methoxy-5-((N-tert-butoxycarbonyl-2-methyl-1,4-diazacycloheptan-1-yl) sulfonyl)isoquinoline prepared in step (4) was dissolved in 25 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 0.87 g of 4-fluoro-1-methoxy-5-((2-methyl-1,4-diazacycloheptan-1-yl)sulfonyl)isoquinoline, with a yield of 93%; MS: [M+1]⁺=354.1; ¹H NMR (400 MHz DMSO), 8.52 (d, 1H), 8.19 (d, 1H), 7.88 (d, 1H), 7.74 (t, 1H), 4.07 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 0.84 (t, 3H).

Example 8: Preparation of 4-chloro-5-((2-methyl-1,4-diazacycloheptan-1-yl)sulfonyl) isoquinolin-1-ol, named as YK1606, with structural formula of

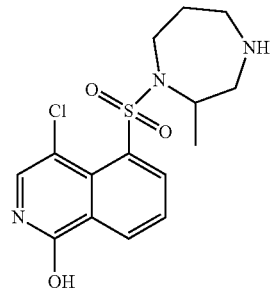 [SMILES: CC1CNCCCN1S(=O)(=O)c1cccc2c(O)ncc(Cl)c12]

(1) Preparation of Intermediate

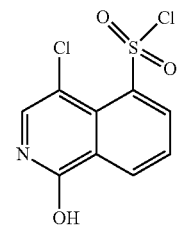 [SMILES: O=S(=O)(Cl)c1cccc2c(O)ncc(Cl)c12]

(1-hydroxy-4-chloroisoquinoline-5-sulfonyl chloride)

1 g of 1-hydroxy-4-chloroisoquinoline was weighed and added to 10 mL of chlorosulfonic acid at 10° C. After the addition was completed, the resulting mixture was heated to 130° C. and reacted for 12 hours, then the resulting reaction solution was poured into ice water to form a precipitate, which was filtered, and the filter cake was dried to obtain 1.4 g of crude product 1-hydroxy-4-chloroisoquinoline-5-sulfonyl chloride.

(2) Preparation of Intermediate 1.8 g of the intermediate

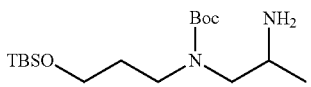 [SMILES: CC(N)CN(CCCO[Si](C)(C)C(C)(C)C)C(=O)OC(C)(C)C]

prepared in step (1) of Example 1 was weighed and dissolved in 20 mL of dichloromethane, then 1-hydroxy-4-chloroisoquinoline-5-sulfonyl chloride prepared in step (1) and 0.9 ml of triethylamine were added and stirred at room temperature for 5 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified with a normal phase silica gel column, and the purified liquid was collected and distilled under reduced pressure to obtain 1.97 g of intermediate

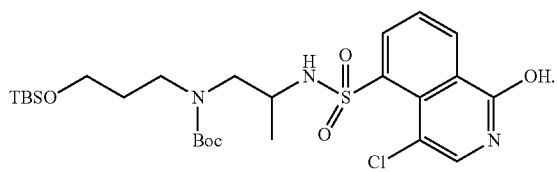 [SMILES: CC(CN(CCCO[Si](C)(C)C(C)(C)C)C(=O)OC(C)(C)C)NS(=O)(=O)c1cccc2c(O)ncc(Cl)c12]

The total yield of steps (1) and (2) was 60%; MS: [M+1]$^+$=589.2.

(3) Preparation of Intermediate

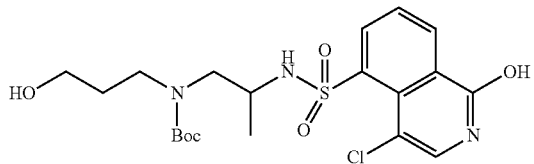 [SMILES: CC(CN(CCCO)C(=O)OC(C)(C)C)NS(=O)(=O)c1cccc2c(O)ncc(Cl)c12]

1.97 g of

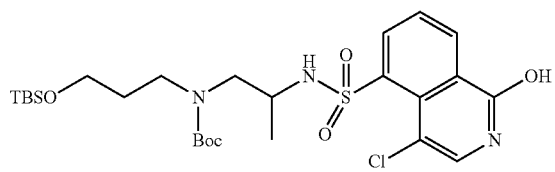 [SMILES: CC(CN(CCCO[Si](C)(C)C(C)(C)C)C(=O)OC(C)(C)C)NS(=O)(=O)c1cccc2c(O)ncc(Cl)c12]

prepared in step (2) was dissolved in 30 mL of tetrahydrofuran, then 1.1 g of TBAF (tetrabutylammonium fluoride) was added and stirred at room temperature for 12 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate. The concentrate was purified through a reverse phase column, the purified liquid was collected and concentrated under reduced pressure to obtain 1.36 g of intermediate

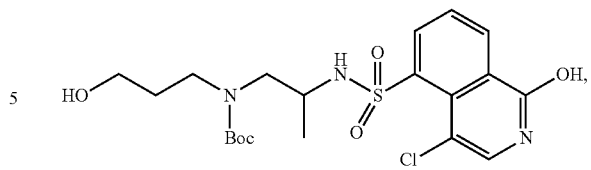

with a yield of 86%; MS: [M+1]$^+$=474.9.

(4) Preparation of Intermediate 4-chloro-5-((N-tert-butoxycarbonyl-2-methyl-1,4-diazacycloheptan-1-yl)sulfonyl)isoquinolin-1-ol

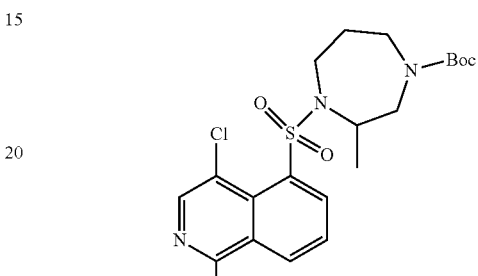

1.36 g of

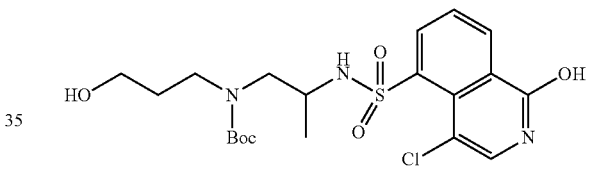

prepared in step (3) was dissolved in 25 mL of tetrahydrofuran, then 0.83 g of triphenylphosphine was added at 0° C., and 0.64 g of DIAD was added dropwise. After the addition was completed, the resulting mixture was warmed to room temperature and stirred for 12 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified through a reverse phase column, and the purified liquid was collected and distilled under reduced pressure to obtain 1.16 g of intermediate 4-chloro-5-((N-tert-butoxycarbonyl-2-methyl-1,4-diazacycloheptan-1-yl)sulfonyl)isoquinolin-1-ol, with a yield of 89%; MS: [M+1]$^+$=456.9.

(5) Preparation of the Target Compound 4-chloro-5-((2-methyl-1,4-diazacycloheptan-1-yl)sulfonyl)isoquinolin-1-ol 1.16 g of 4-chloro-5-((N-tert-butoxycarbonyl-2-methyl-1,4-diazacycloheptan-1-yl)sulfonyl) isoquinolin-1-ol prepared in step (4) was dissolved in 25 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 0.86 g of 4-chloro-5-((2-methyl-1,4-diazacycloheptan-1-yl)sulfonyl)isoquinolin-1-ol, with a yield of 96%; MS: [M+1]$^+$=356.1; $^1$H NMR (400 MHz DMSO), 8.48 (d, 1H), 8.37 (d, 1H), 7.59 (t, 1H), 7.33 (d, 1H), 3.97-4.00 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.56 (t, 2H), 0.92 (d, 3H).

Example 9: Preparation of 4-ethyl-5-((2-methyl-1,4-diazacycloheptan-1-yl)sulfonyl) isoquinolin-1-ol, named as YK1607, with structural formula of

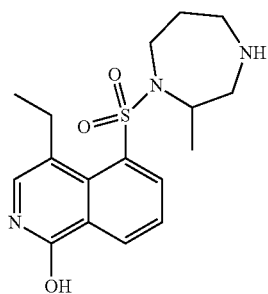 [SMILES: CCc1cnc(O)c2cccc(S(=O)(=O)N3CCCNCC3C)c12]

(1) Preparation of Intermediate

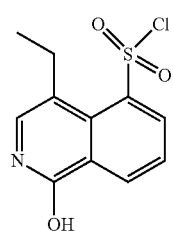 [SMILES: CCc1cnc(O)c2cccc(S(=O)(=O)Cl)c12]

(1-hydroxy-4-ethylisoquinoline-5-sulfonyl chloride)

1 g of 1-hydroxy-4-ethylisoquinoline was weighed and added to 10 mL of chlorosulfonic acid at 10° C. After the addition was completed, the resulting mixture was heated to 140° C. and reacted for 10 hours, then the resulting reaction solution was poured into ice water to form a precipitate, which was filtered, and the filter cake was dried to obtain 1.5 g of crude product 1-hydroxy-4-ethylisoquinoline-5-sulfonyl chloride.

(2) Preparation of Intermediate

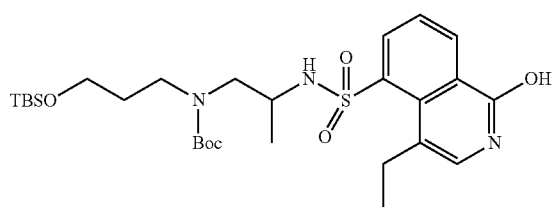 [SMILES: CCc1cnc(O)c2cccc(S(=O)(=O)NC(C)CN(CCCO[Si](C)(C)C(C)(C)C)C(=O)OC(C)(C)C)c12]

2.0 g of the intermediate

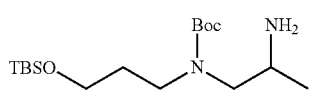 [SMILES: CC(N)CN(CCCO[Si](C)(C)C(C)(C)C)C(=O)OC(C)(C)C]

prepared in step (1) of Example 1 was weighed and dissolved in 30 mL of dichloromethane, then 1-hydroxy-4-ethylisoquinoline-5-sulfonyl chloride prepared in step (1) and an appropriate amount of triethylamine were added and stirred at room temperature for 4 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified with a normal phase silica gel column, the purified liquid was collected and distilled under reduced pressure to obtain 2.18 g of intermediate

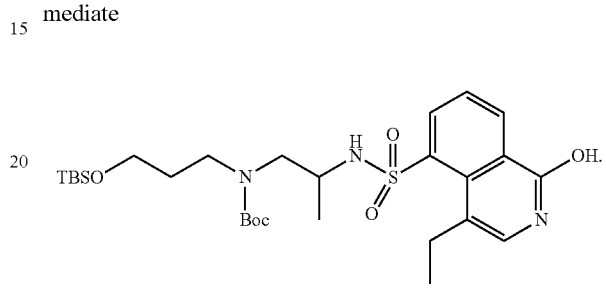

The total yield of step (1) and step (2) was 65%; MS: [M+1]$^+$=582.8.

(3) Preparation of Intermediate

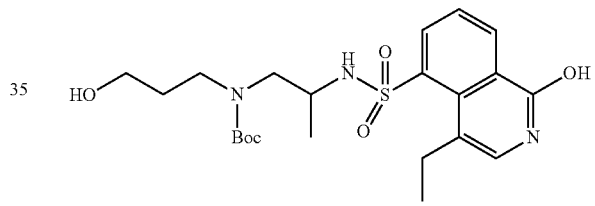

2.18 g of

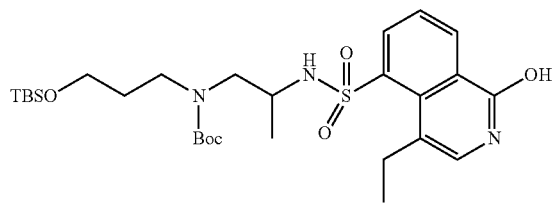 [SMILES: CCc1cnc(O)c2cccc(S(=O)(=O)NC(C)CN(CCCO[Si](C)(C)C(C)(C)C)C(=O)OC(C)(C)C)c12]

prepared in step (2) was dissolved in 30 mL of tetrahydrofuran, then 1.3 g of TBAF (tetrabutylammonium fluoride) was added and stirred at room temperature for 10 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate. The concentrate was purified through a reverse phase column, the purified liquid was collected and concentrated under reduced pressure to obtain 1.52 g of intermediate

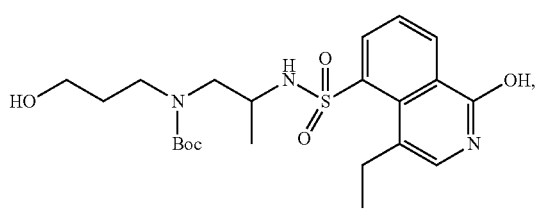 [SMILES: CCc1cnc(O)c2cccc(S(=O)(=O)NC(C)CN(CCCO)C(=O)OC(C)(C)C)c12]

with a yield of 87%; MS: [M+1]⁺=468.5.

(4) Preparation of Intermediate 4-ethyl-5-((N-tert-butoxycarbonyl-2-methyl-1,4-diazacycloheptan-1-yl)sulfonyl)isoquinolin-1-ol

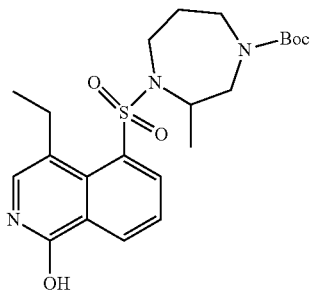 [SMILES: CCc1cnc(O)c2cccc(S(=O)(=O)N3CCCN(C(=O)OC(C)(C)C)CC3C)c12]

1.52 g of

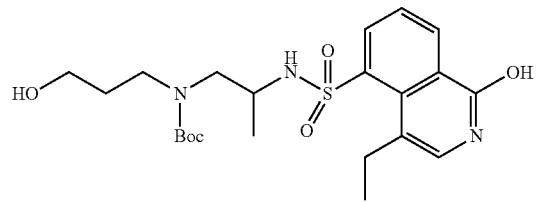 [SMILES: CCc1cnc(O)c2cccc(S(=O)(=O)NC(C)CN(CCCO)C(=O)OC(C)(C)C)c12]

prepared in step (3) was dissolved in 30 mL of tetrahydrofuran, then 1.0 g of triphenylphosphine was added at 0° C., and 0.79 g of DIAD was added dropwise. After the addition was completed, the resulting mixture was warmed to room temperature and stirred for 12 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified through a reverse phase column, the purified liquid was collected and distilled under reduced pressure to obtain 1.3 g of intermediate 4-ethyl-5-((N-tert-butoxycarbonyl-2-methyl-1,4-diazacycloheptan-1-yl)sulfonyl)isoquinolin-1-ol, with a yield of 89%; MS: [M+1]⁺=450.5.

(5) Preparation of Target Compound 4-ethyl-5-((2-methyl-1,4-diazacycloheptan-1-yl)sulfonyl)isoquinolin-1-ol 1.3 g of 4-ethyl-5-((N-tert-butoxycarbonyl-2-methyl-1,4-diazacycloheptan-1-yl)sulfonyl) isoquinolin-1-ol prepared in step (4) was dissolved in 25 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 0.9 g of 4-ethyl-5-((2-methyl-1,4-diazacycloheptan-1-yl) sulfonyl)isoquinolin-1-ol, with a yield of 96%; MS: [M+1]⁺= 350.1; ¹H NMR (400 MHz DMSO), 8.38 (s, 1H), 8.27 (d, 1H), 7.51 (t, 1H), 7.23 (d, 1H), 3.99-4.02 (m, 1H), 3.61-3.65 (m, 1H), 3.22-3.25 (m, 1H), 2.99-3.04 (m, 1H), 2.79-2.82 (m, 1H), 2.53-2.64 (m, 1H), 2.51-2.53 (m, 1H), 2.43 (q, 2H), 1.52 (t, 2H), 1.18 (t, 3H), 0.90 (d, 3H).

Example 10: Preparation of 5-((2-cyclopropyl-1,4-diazacycloheptan-1-yl) sulfonyl)isoquinoline, named as YK1608, with structural formula of

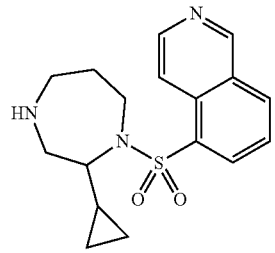 [SMILES: O=S(=O)(c1cccc2cnccc12)N1CCCNCC1C1CC1]

(1) Preparation of Intermediate

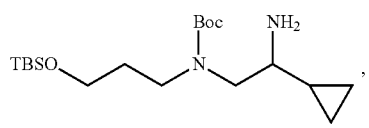

with synthetic scheme as follows:

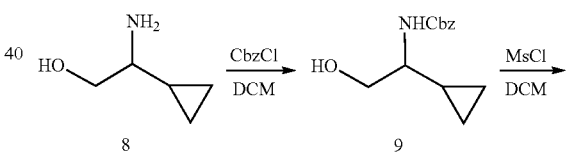

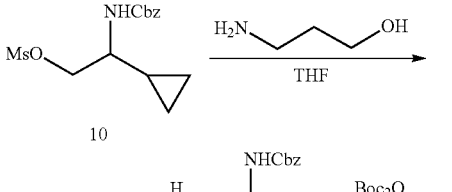

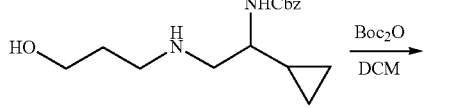

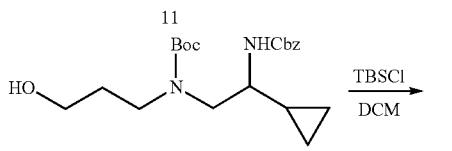

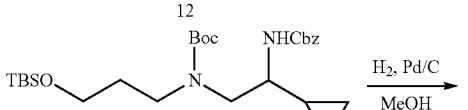

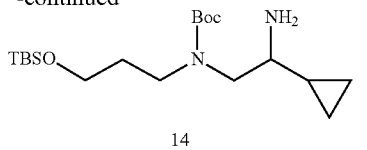
14

50 g of 2-amino-2-cyclopropylethanol was weighed and dissolved in 250 mL of dichloromethane solution, then benzyl chloroformate (1.0 eq) and triethylamine (5.0eq) were added at 5° C., and then the reaction was carried out under stirring at 15° C. for 15 hours, the resulting reaction solution was extracted three times with dichloromethane, the resulting organic phases were combined and distilled under reduced pressure to obtain a concentrate. The concentrate was separated by column chromatography to obtain a yellow solid benzyl (1-cyclopropyl-2-hydroxyethyl)carbamate (Compound 9);

50 g of benzyl (1-cyclopropyl-2-hydroxyethyl)carbamate and 300 mL of dichloromethane were weighed, then methanesulfonyl chloride (1.05eq) and triethylamine (3.0eq) were added at 15° C., and then the reaction was carried out under stirring at 15° C. for 15 hours, the resulting reaction solution was extracted three times with dichloromethane-saturated brine (the volume ratio of dichloromethane to saturated brine was 2:3), the resulting organic phases were combined and distilled under reduced pressure to obtain a concentrate. The concentrate was purified with a normal phase silica gel column, the purified liquid was collected and distilled under reduced pressure to obtain 2-((benzyloxy)carbonyl)amino)-2-cyclopropylethyl methanesulfonate (Compound 10);

63 g of 2-((benzyloxy)carbonyl)amino)-2-cyclopropylethyl methanesulfonate was weighed and dissolved in 770 mL of tetrahydrofuran, then 3-aminopropan-1-ol (7.0eq) was added at 15° C., and then the reaction was carried out under stirring at 15° C. for 6 hours. The resulting reaction solution was concentrated under reduced pressure and then extracted three times with hydrochloric acid-ethyl acetate (the volume ratio of hydrochloric acid to ethyl acetate was 5:2). The resulting organic phases were combined, filtered, and concentrated under reduced pressure to obtain a yellow solid benzyl (1-cyclopropyl-2-((3-hydroxypropyl)amino)ethyl)carbamate (Compound 11);

50 g of benzyl (1-cyclopropyl-2-((3-hydroxypropyl)amino)ethyl)carbamate was weighed and dissolved in 400 mL of dichloromethane, then di-tert-butyl dicarbonate (1.1eq) and triethylamine (5.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 3:8), the resulting organic phases were combined and distilled under reduced pressure to obtain a concentrate, the concentrate was purified with a normal phase silica gel column, the purified liquid was collected and distilled under reduced pressure to obtain tert-butyl (2-((benzyloxy)carbonyl)amino)-2-cyclopropylethyl(3-hydroxypropyl)carbamate (Compound 12);

65 g of tert-butyl (2-((benzyloxy)carbonyl)amino)-2-cyclopropylethyl(3-hydroxypropyl)carbamate were weighed and dissolved in 300 mL of dichloromethane, then tert-butyldimethylchlorosilane (1.1eq) and imidazole (2.0eq) were added at 15° C., and then the reaction was carried out under stirring at 15° C. for 15 hours. The resulting reaction solution was extracted three times with dichloromethane, the resulting organic phases were combined and distilled under reduced pressure to obtain a yellow oily substance tert-butyl (2-((benzyloxy)carbonyl)amino)-2-cyclopropylethyl) (3-((tert-butyldimethylsiloxy)propyl)carbamate (Compound 13);

77 g of tert-butyl (2-((benzyloxy)carbonyl)amino)-2-cyclopropylethyl)(3-((tert-butyldimethylsiloxy)propyl) carbamate was dissolved in 400 mL of methanol, subjected to catalytic hydrogenation by using palladium on carbon as catalyst under stirring at 15° C. for 15 hours. The resulting reaction solution was concentrated under reduced pressure to obtain a yellow oily substance tert-butyl (2-amino-2-cyclopropylethyl)(3-((tert-butyldimethylsiloxy)propyl)carbamate (Compound 14).

(2) Preparation of Intermediate isoquinoline-5-sulfonyl chloride 1 g of isoquinoline was weighed and added to 10 mL of chlorosulfonic acid at 10° C. After the addition was completed, the resulting mixture was heated to 130° C. and reacted for 12 hours, then the resulting reaction solution was poured into ice water to form a precipitate, which was filtered, and the filter cake was dried to obtain 1.62 g of crude product isoquinoline-5-sulfonyl chloride.

(3) Preparation of Intermediate

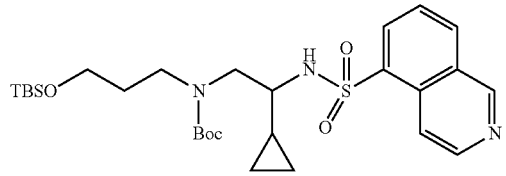 [SMILES: CC(C)(C)OC(=O)N(CCCO[Si](C)(C)C(C)(C)C)CC(NS(=O)(=O)c1cccc2cnccc12)C1CC1]

2.8 g of the intermediate

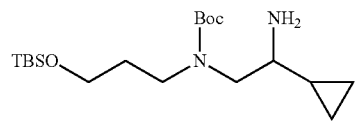 [SMILES: CC(C)(C)OC(=O)N(CCCO[Si](C)(C)C(C)(C)C)CC(N)C1CC1]

prepared in step (1) was weighed and dissolved in 40 mL of dichloromethane, then the isoquinoline-5-sulfonyl chloride prepared in step (2) and 0.7 ml of triethylamine were added and stirred at room temperature for 5 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified with a normal phase silica gel column, the purified liquid was collected and distilled under reduced pressure to obtain 2.96 g of intermediate

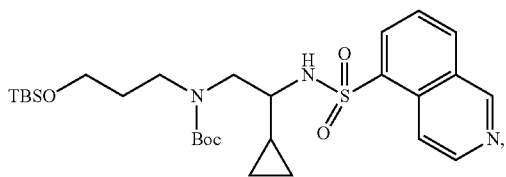 [SMILES: CC(C)(C)OC(=O)N(CCCO[Si](C)(C)C(C)(C)C)CC(NS(=O)(=O)c1cccc2cnccc12)C1CC1]

the total yield of step (2) and step (3) was 68%; MS: [M+1]$^+$=564.8.

(4) Preparation of Intermediate

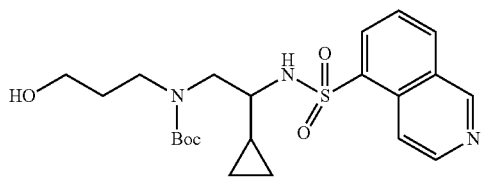 [SMILES: CC(C)(C)OC(=O)N(CCCO)CC(NS(=O)(=O)c1cccc2cnccc12)C1CC1]

2.96 g of

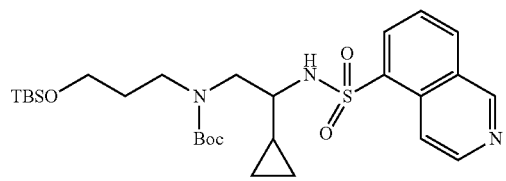 [SMILES: CC(C)(C)OC(=O)N(CCCO[Si](C)(C)C(C)(C)C)CC(NS(=O)(=O)c1cccc2cnccc12)C1CC1]

prepared in step (3) was dissolved in 50 mL of tetrahydrofuran, then 1.5 g of TBAF (tetrabutylammonium fluoride) was added and stirred at room temperature for 12 hours, the resulting reaction solution was extracted three times with dichloromethane-saturated brine (the volume ratio of dichloromethane to saturated brine was 6:10), the resulting organic phases were collected and distilled under reduced pressure to obtain a concentrate. The concentrate was purified through a reverse phase column, the purified liquid was collected and concentrated under reduced pressure to obtain 2.0 g of intermediate

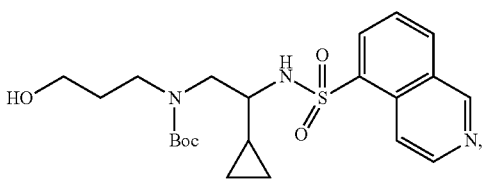 [SMILES: CC(C)(C)OC(=O)N(CCCO)CC(NS(=O)(=O)c1cccc2cnccc12)C1CC1]

with a yield of 85%; MS: [M+1]$^+$=450.5.

(5) Preparation of Intermediate 5-((N-tert-butoxycarbonyl-2-cyclopropyl-1,4-diazacycloheptan-1-yl)sulfonyl)isoquinoline

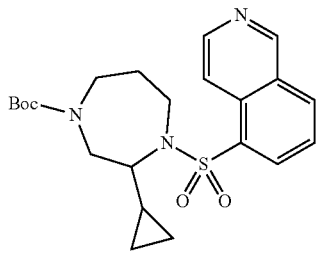 [SMILES: CC(C)(C)OC(=O)N1CCCN(S(=O)(=O)c2cccc3cnccc23)C(C2CC2)C1]

2.0 g of

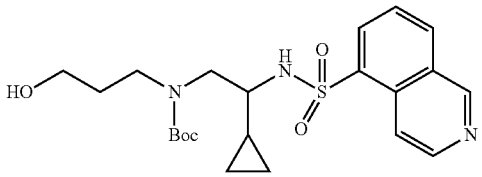 [SMILES: CC(C)(C)OC(=O)N(CCCO)CC(NS(=O)(=O)c1cccc2cnccc12)C1CC1]

prepared in step (4) was dissolved in 30 mL of tetrahydrofuran, then 1.4 g of triphenylphosphine was added at 0° C., and 1.0 g of diethyl azodicarboxylate (DEAD) was added dropwise. After the addition was completed, the resulting mixture was warmed to room temperature, and stirred for 12 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified through a reverse phase column, the purified liquid was collected and distilled under reduced pressure to obtain 1.7 g of intermediate 5-((N-tert-butoxycarbonyl-2-cyclopropyl-1,4-diazacycloheptan-1-yl)sulfonyl)isoquinoline, with a yield of 89%; MS: [M+1]$^+$=432.5.

(6) Preparation of Target Compound 5-((2-cyclopropyl-1,4-diazacycloheptan-1-yl)sulfonyl)isoquinoline 1.7 g of 5-((N-tert-butoxycarbonyl-2-cyclopropyl-1,4-diazacycloheptan-1-yl)sulfonyl)-isoquinoline prepared in step (5) was dissolved in 30 mL of 4M HCl(g) in dioxane solution, stirred at room temperature for 2 hours, and distilled under reduced pressure to remove the solvent and obtain a concentrate, the concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 1.2 g of the target compound 5-((2-cyclopropyl-1,4-diazacycloheptan-1-yl)sulfonyl)isoquinoline, with a yield of 94%; MS: [M+1]$^+$=332.1; $^1$H NMR (400 MHz DMSO), 8.78 (s, 1H), 8.47 (d, 1H), 8.32 (d, 1H), 7.58 (t, 1H), 7.32 (d, 1H), 7.13 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.61-0.63 (m, 1H), 0.47-0.50 (m, 4H).

Example 11: Preparation of 5-((2-isopropyl-1,4-diazacycloheptan-1-yl)sulfonyl)isoquinolin-1-ol, named as YK1609, with structural formula of

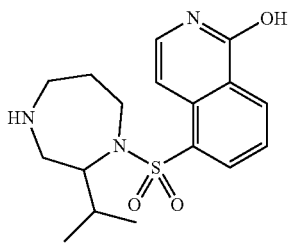 [SMILES: CC(C)C1CNCCCN1S(=O)(=O)c1cccc2c(O)nccc12]

(1) Preparation of Intermediate

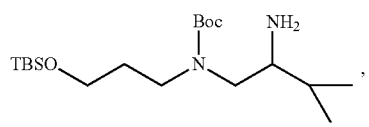 [SMILES: CC(C)C(N)CN(CCCO[Si](C)(C)C(C)(C)C)C(=O)OC(C)(C)C]

with synthetic scheme as follows:

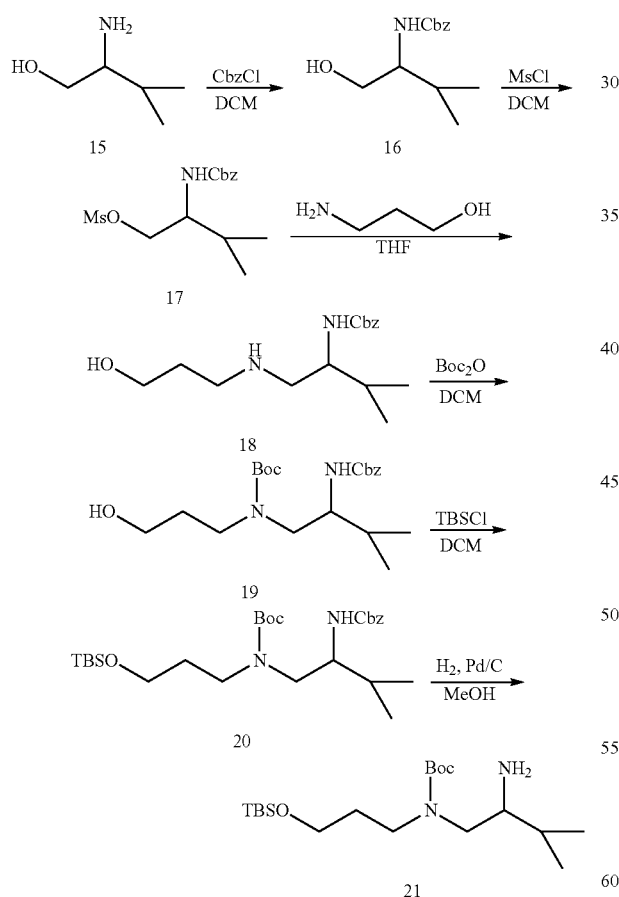

50 g of 2-amino-3-methylbutanol was weighed and dissolved in 250 mL of dichloromethane solution, then benzyl chloroformate (1.0 eq) and triethylamine (4.0eq) were added at 5° C., and then the reaction was carried out under stirring at 15° C. for 10 hours, the resulting reaction solution was extracted with dichloromethane three times, the resulting organic phases were combined and distilled under reduced pressure to obtain a concentrate, the concentrate was separated by column chromatography to obtain a yellow solid benzyl (1-hydroxy-3-methylbutan-2-yl)carbamate (Compound 16);

50 g of benzyl (1-hydroxy-3-methylbutan-2-yl)carbamate and 300 mL of dichloromethane were weighed, then methanesulfonyl chloride (1.05eq) and triethylamine (3.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 1:2), the resulting organic phases were combined and distilled under reduced pressure to obtain a concentrate, the concentrate was purified by a normal phase silica gel column, the purified liquid was collected and distilled under reduced pressure to obtain 2-((benzyloxy)carbonyl)amino)-3-methylbutyl methanesulfonate (Compound 17);

63 g of 2-((benzyloxy)carbonyl)amino)-3-methylbutyl methanesulfonate was weighed and dissolved in 770 mL of tetrahydrofuran, then 3-aminopropan-1-ol (7.0eq) was added at 15° C., and then the reaction was carried out under stirring at 15° C. for 15 hours, the resulting reaction solution was concentrated under reduced pressure and then extracted three times with hydrochloric acid-ethyl acetate (the volume ratio of hydrochloric acid to ethyl acetate was 5:2), the resulting organic phases were combined, filtered, and concentrated under reduced pressure to obtain a yellow solid benzyl (1-((3-hydroxypropyl)amino)-3-methylbutan-2-yl)carbamate (Compound 18);

50 g of benzyl (1-((3-hydroxypropyl)amino)-3-methylbutan-2-yl)carbamate was weighed and dissolved in 400 mL of dichloromethane, then di-tert-butyl dicarbonate (1.1eq) and triethylamine (3.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 3:5), the resulting organic phases were combined and distilled under reduced pressure to obtain a concentrate, the concentrate was purified with a normal phase silica gel column, the purified liquid was collected and distilled under reduced pressure to obtain tert-butyl (2-((benzyloxy)carbonyl)amino)-3-methylbutyl(3-hydroxypropyl)carbamate (Compound 19);

65 g of tert-butyl (2-((benzyloxy)carbonyl)amino)-3-methylbutyl(3-hydroxypropyl)carbamate was weighed and dissolved in 300 mL of dichloromethane, then tert-butyldimethylchlorosilane (1.1eq) and imidazole (2.0eq) were added at 15° C., and then the reaction was carried out under stirring at 15° C. for 15 hours. The resulting reaction solution was extracted three times with dichloromethane, and the resulting organic phases were combined and distilled under reduced pressure to obtain a yellow oily substance tert-butyl (2-((benzyloxy)carbonyl)amino)-3-methylbutyl(3-((tert-butyldimethylsiloxy)propyl)carbamate (Compound 20);

77 g of tert-butyl (2-((benzyloxy)carbonyl)amino)-3-methylbutyl(3-((tert-butyldimethylsiloxy)propyl)carbamate was weighed and dissolved in 400 mL of methanol, subjected to catalytic hydrogenation by using palladium on carbon as catalyst under stirring at 15° C. for 10 hours. The resulting reaction solution was concentrated under reduced pressure to obtain a yellow oily substance tert-butyl (2-amino-3-methylbutyl)(3-((tert-butyldimethylsiloxy)propyl)carbamate (Compound 21).

(2) Preparation of Intermediate

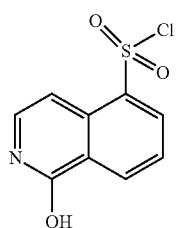 [SMILES: O=S(=O)(Cl)c1cccc2c(O)nccc12]

(1-hydroxyisoquinoline-5-sulfonyl chloride)

1 g of 1-hydroxyisoquinoline was weighed and added to 10 mL of chlorosulfonic acid at 10° C. After the addition was completed, the resulting mixture was heated to 120° C. and reacted for 12 hours, then the resulting reaction solution was poured into ice water to form a precipitate, which was filtered, and the filter cake was dried to obtain 1.6 g of crude product 1-hydroxyisoquinoline-5-sulfonyl chloride.

(3) Preparation of Intermediate

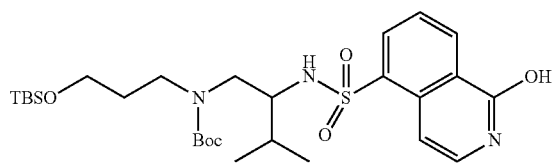 [SMILES: CC(C)C(CN(CCCO[Si](C)(C)C(C)(C)C)C(=O)OC(C)(C)C)NS(=O)(=O)c1cccc2c(O)nccc12]

2.5 g of the intermediate

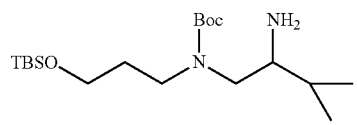 [SMILES: CC(C)C(N)CN(CCCO[Si](C)(C)C(C)(C)C)C(=O)OC(C)(C)C]

prepared in step (1) was weighed and dissolved in 25 mL of dichloromethane, then 1-hydroxyisoquinoline-5-sulfonyl chloride prepared in step (2) and 1 ml of triethylamine were added, and stirred at room temperature for 4 hours, the resulting reaction solution was extracted three times with dichloromethane-saturated brine (the volume ratio of dichloromethane to saturated brine was 6:10), the resulting organic phases were combined and distilled under reduced pressure to obtain a concentrate, the concentrate was purified with a normal phase silica gel column, the purified liquid was collected and distilled under reduced pressure to obtain 2.6 g of intermediate

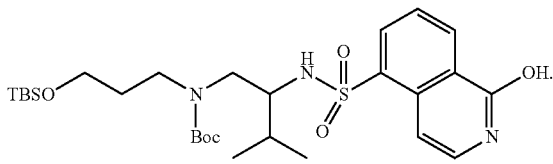 [SMILES: CC(C)C(CN(CCCO[Si](C)(C)C(C)(C)C)C(=O)OC(C)(C)C)NS(=O)(=O)c1cccc2c(O)nccc12]

The total yield of step (2) and step (3) was 67%; MS: [M+1]$^+$=582.8.

(4) Preparation of Intermediate

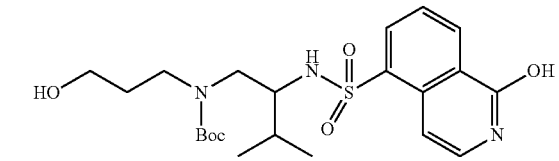 [SMILES: CC(C)C(CN(CCCO)C(=O)OC(C)(C)C)NS(=O)(=O)c1cccc2c(O)nccc12]

2.6 g of

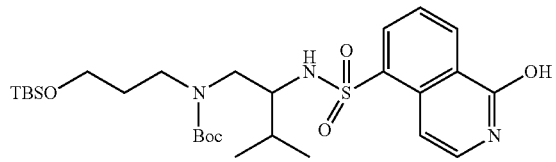 [SMILES: CC(C)C(CN(CCCO[Si](C)(C)C(C)(C)C)C(=O)OC(C)(C)C)NS(=O)(=O)c1cccc2c(O)nccc12]

prepared in step (3) was dissolved in 40 mL of tetrahydrofuran, then 1.3 g of TBAF (tetrabutylammonium fluoride) was added, stirred at room temperature for 10 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate, the concentrate was purified through a reverse phase column, the purified liquid was collected and concentrated under reduced pressure to obtain 1.7 g of intermediate

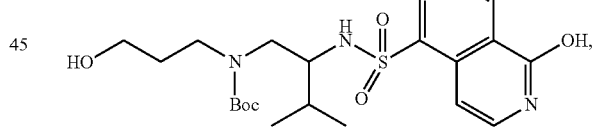

with a yield of 82%; MS: [M+1]$^+$=468.5.

(5) Preparation of Intermediate 5-((N-tert-butoxycarbonyl-2-isopropyl-1,4-diazacycloheptan-1-yl)sulfonyl)isoquinolin-1-ol

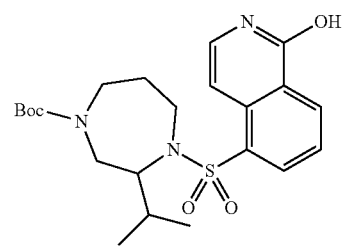 [SMILES: CC(C)C1CN(C(=O)OC(C)(C)C)CCCN1S(=O)(=O)c1cccc2c(O)nccc12]

1.7 g of

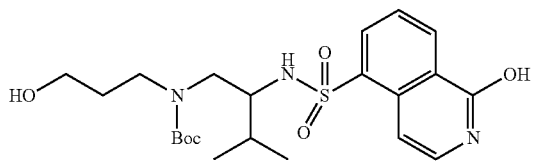 [SMILES: CC(C)C(CN(CCCO)C(=O)OC(C)(C)C)NS(=O)(=O)c1cccc2c(O)nccc12]

prepared in step (4) was dissolved in 30 mL of tetrahydrofuran, then 1.0 g of triphenylphosphine was added at 0° C., and 0.8 g of DEAD was added dropwise. After the addition was completed, the resulting mixture was warmed to room temperature and stirred for 12 hours, the resulting reaction solution was extracted three times with dichloromethane-saturated brine (the volume ratio of dichloromethane to saturated brine was 6:10), the resulting organic phases were combined and distilled under reduced pressure to obtain a concentrate, the concentrate was purified through a reverse phase column, the purified liquid was collected and distilled under reduced pressure to obtain 1.48 g of intermediate 5-((N-tert-butoxycarbonyl-2-isopropyl-1,4-diazacycloheptan-1-yl)sulfonyl)isoquinolin-1-ol, with a yield of 91%; MS: [M+1]$^+$=450.5.

(6) Preparation of Target Compound 5-((2-isopropyl-1,4-diazacycloheptan-1-yl)sulfonyl)isoquinolin-1-ol 1.48 g of 5-((N-tert-butoxycarbonyl-2-isopropyl-1,4-diazacycloheptan-1-yl)sulfonyl) isoquinolin-1-ol prepared in step (5) was dissolved in 25 mL of 4M HCl(g) in dioxane solution, stirred at room temperature for 2 hours, and distilled under reduced pressure to remove the solvent and obtain the concentrate, the concentrate was purified through a reverse phase column with aqueous ammonium bicarbonate-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 1.09 g of the target compound 5-((2-isopropyl-1,4-diazacycloheptan-1-yl)sulfonyl)isoquinolin-1-ol, the yield was 95%; MS: [M+1]$^+$=350.1; $^1$H NMR (400 MHz DMSO), 8.45 (d, 1H), 8.32 (d, 1H), 7.54 (t, 1H), 7.29 (d, 1H), 7.09 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.52 (t, 2H), 0.90-0.91 (m, 1H), 0.85 (d, 9H).

Example 12: Preparation of 5-((2-ethyl-1,4-diazacycloheptan-1-yl)sulfonyl)-1-methoxyisoquinoline, named as YK1610, with structural formula of

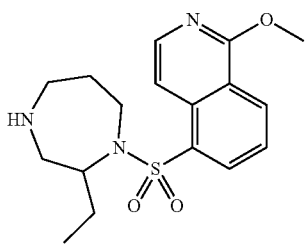 [SMILES: CCC1CNCCCN1S(=O)(=O)c1cccc2c(OC)nccc12]

(1) Preparation of Intermediate

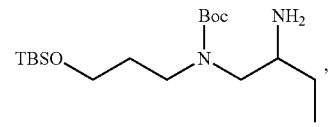 [SMILES: CCC(N)CN(CCCO[Si](C)(C)C(C)(C)C)C(=O)OC(C)(C)C]

with synthetic scheme as follows:

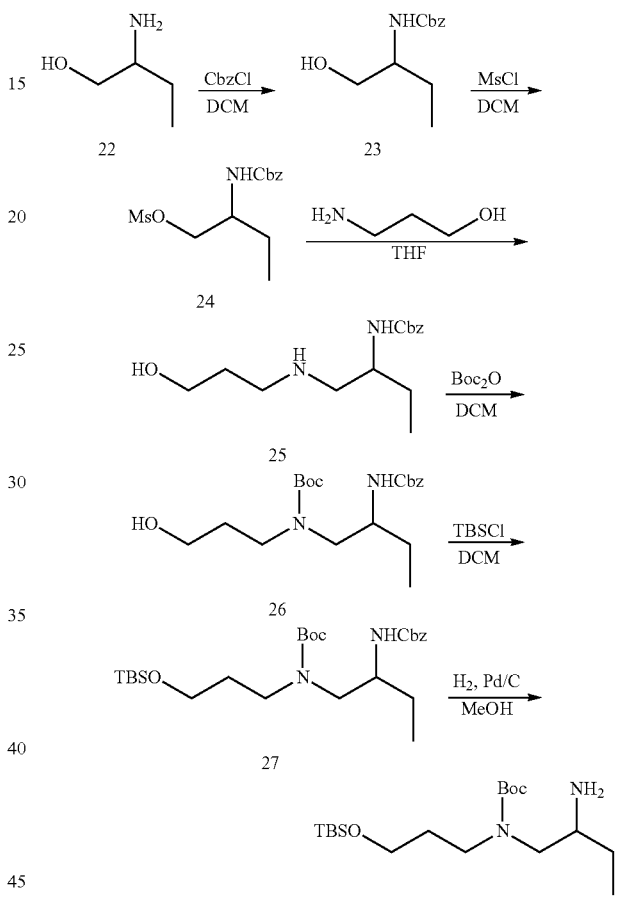

50 g of 2-aminobutan-1-ol was weighed and dissolved in 250 mL of dichloromethane solution, then benzyl chloroformate (2.0eq) and triethylamine (3.0eq) were added at 5° C., and then the reaction was carried out under stirring at 15° C. for 5 hours, the resulting reaction solution was extracted with dichloromethane three times, the resulting organic phases were combined and distilled under reduced pressure to obtain a concentrate, the concentrate was separated by column chromatography to obtain a yellow solid benzyl (1-hydroxybutyl-2-yl)carbamate (Compound 23);

50 g of benzyl (1-hydroxybutyl-2-yl)carbamate and 300 mL of dichloromethane were weighed, then methanesulfonyl chloride (1.10 eq) and triethylamine (3.0eq) were added at 15° C., and then the reaction was carried out under stirring at 15° C. for 10 hours. The resulting reaction solution was extracted three times with dichloromethane-saturated brine (the volume ratio of dichloromethane to saturated brine was 1:2), the resulting organic phases were combined and distilled under reduced pressure to obtain a concentrate. The concentrate was purified by a normal phase silica gel column, the purified liquid was collected and distilled under reduced pressure to obtain butyl 2-((benzyloxy)carbonyl)amino)methanesulfonate (Compound 24);

63 g of butyl 2-((benzyloxy)carbonyl)amino)methanesulfonate was weighed and dissolved in 770 mL of tetrahydrofuran, then 3-aminopropan-1-ol (7.0eq) was added at 15° C., and then the reaction was carried out under stirring at 15° C. for 15 hours. The resulting reaction solution was concentrated under reduced pressure and then extracted three times with hydrochloric acid-ethyl acetate (the volume ratio of hydrochloric acid to ethyl acetate was 5:2). The resulting organic phases were combined, filtered, and concentrated under reduced pressure to obtain a yellow solid benzyl (1-((3-hydroxypropyl)amino)butyl)carbamate (Compound 25);

50 g of benzyl (1-((3-hydroxypropyl)amino)butyl)carbamate was weighed and dissolved in 400 mL of dichloromethane, then di-tert-butyl dicarbonate (1.1eq) and triethylamine (3.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 3:8), the resulting organic phases were combined and distilled under reduced pressure to obtain a concentrate. The concentrate was purified with a normal phase silica gel column, the purified liquid was collected and distilled under reduced pressure to obtain tert-butyl (2-((benzyloxy)carbonyl)amino)butyl(3-hydroxypropyl)carbamate (Compound 26);

65 g of tert-butyl (2-((benzyloxy)carbonyl)amino)butyl (3-hydroxypropyl)carbamate was weighed and dissolved in 300 mL of dichloromethane, then tert-butyldimethylchlorosilane (1.1eq) and imidazole (3.0eq) were added at 15° C., and then the reaction was carried out under stirring at 15° C. for 15 hours. The resulting reaction solution was extracted with dichloromethane three times, the resulting organic phases were combined and distilled under reduced pressure to obtain a yellow oily substance tert-butyl (2-(((benzyloxy)carbonyl)amino)butyl)(3-((tert-butyldimethylsiloxy)propyl) carbamate (Compound 27);

77 g of tert-butyl (2-(((benzyloxy)carbonyl)amino)butyl) (3-((tert-butyldimethylsiloxy)propyl)carbamate was weighed and dissolved in 400 mL of methanol, subjected to catalytic hydrogenation by using palladium on carbon as catalyst under stirring at 15° C. for 15 hours. The resulting reaction solution was concentrated under reduced pressure to obtain a yellow oily substance tert-butyl (2-aminobutyl)(3-((tert-butyldimethylsiloxy) propyl)carbamate (Compound 28).

(2) Preparation of Intermediate 1-methoxyisoquinoline-5-sulfonyl chloride

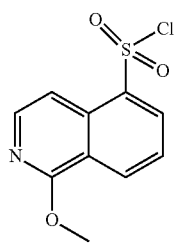 [SMILES: COc1nccc2c(S(=O)(=O)Cl)cccc12]

1 g of 1-methoxyisoquinoline was weighed and added to 10 mL of chlorosulfonic acid at 10° C. After the addition was completed, the resulting mixture was heated to 130° C. and reacted for 12 hours, then the resulting reaction solution was poured into ice water to form a precipitate, which was filtered, and the filter cake was dried to obtain 1.5 g of crude product 1-methoxyisoquinoline-5-sulfonyl chloride.

(3) Preparation of Intermediate

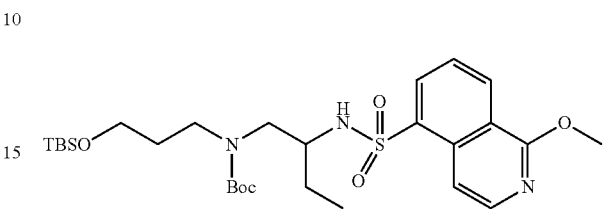

2.2 g of the intermediate

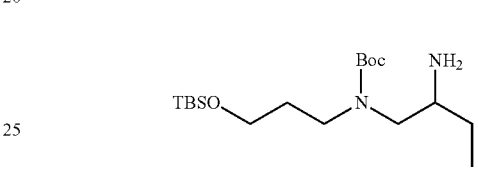

prepared in step (1) was weighed and dissolved in 25 mL of dichloromethane, then 1-methoxyisoquinoline-5-sulfonyl chloride prepared in step (2) and 1 ml of triethylamine were added and stirred at room temperature for 4 hours, the resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified with a normal phase silica gel column, the purified liquid was collected and distilled under reduced pressure to obtain 2.37 g of intermediate

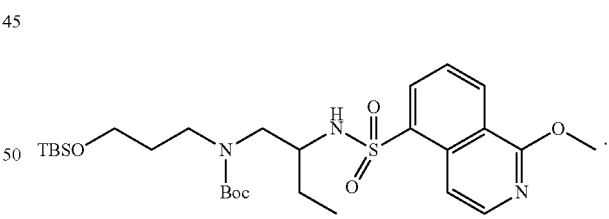

The total yield of step (2) and step (3) was 65%; MS: [M+1]$^+$=582.8.

(4) Preparation of Intermediate

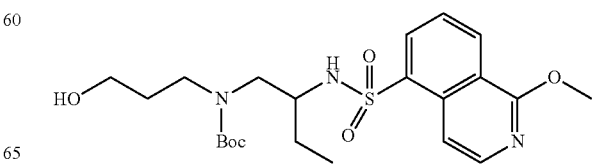

2.37 g of

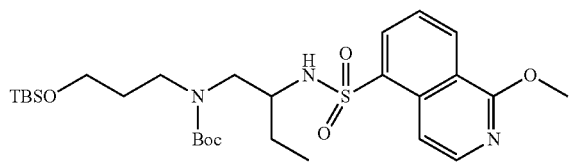 [SMILES: CCC(CN(CCCO[Si](C)(C)C(C)(C)C)C(=O)OC(C)(C)C)NS(=O)(=O)c1cccc2c(OC)nccc12]

prepared in step (3) was dissolved in 30 mL of tetrahydrofuran, then 1.27 g of TBAF (tetrabutylammonium fluoride) was added and stirred at room temperature for 12 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate. The concentrate was purified through a reverse phase column, the purified liquid was collected and concentrated under reduced pressure to obtain 1.6 g of intermediate

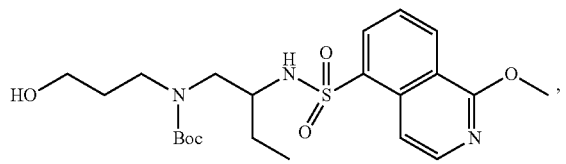 [SMILES: CCC(CN(CCCO)C(=O)OC(C)(C)C)NS(=O)(=O)c1cccc2c(OC)nccc12]

with a yield of 85%; MS: [M+1]$^+$=468.5.

(5) Preparation of Intermediate 5-((N-tert-butoxycarbonyl-2-ethyl-1,4-diazacycloheptan-1-yl)sulfonyl)-1-methoxyisoquinoline

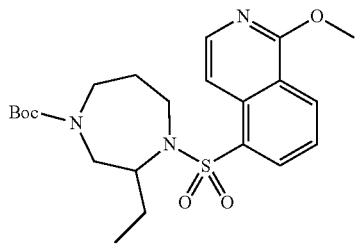 [SMILES: CCC1CN(C(=O)OC(C)(C)C)CCCN1S(=O)(=O)c1cccc2c(OC)nccc12]

1.6 g of

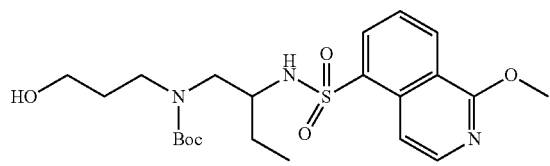 [SMILES: CCC(CN(CCCO)C(=O)OC(C)(C)C)NS(=O)(=O)c1cccc2c(OC)nccc12]

prepared in step (4) was dissolved in 30 mL of tetrahydrofuran, then 0.98 g of triphenylphosphine was added at 0° C., and 0.83 g of DEAD was added dropwise. After the addition was completed, the resulting mixture was warmed to room temperature and stirred for 12 hours. The resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified through a reverse phase column, the purified liquid was collected and distilled under reduced pressure to obtain 1.36 g of intermediate 5-((N-tert-butoxycarbonyl-2-ethyl-1,4-diazacycloheptan-1-yl)sulfonyl)-1-methoxyisoquinoline, with a yield of 89%; MS: [M+1]$^+$=450.5.

(6) Preparation of Target Compound 5-((2-ethyl-1,4-diazacycloheptan-1-yl)sulfonyl)-1-methoxyisoquinoline 1.36 g of 5-((N-tert-butoxycarbonyl-2-ethyl-1,4-diazacycloheptan-1-yl)sulfonyl)-1-methoxyisoquinoline was dissolved in 20 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 0.97 g of the target compound 5-((2-ethyl-1,4-diazacycloheptan-1-yl)sulfonyl)-1-methoxyisoquinoline, with a yield of 93%; MS: [M+1]$^+$=350.1; $^1$H NMR (400 MHz DMSO), 8.43-8.52 (m, 2H), 8.17 (d, 1H), 7.87 (d, 1H), 7.72 (t, 1H), 4.06 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 0.80-0.83 (m, 2H), 0.68 (t, 3H).

Example 13: Preparation of 5-((2-butyl-1,4-diazacycloheptan-1-yl)sulfonyl)isoquinolin-1-ol, named as YK1611, with the structural formula of

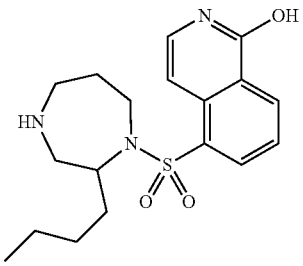 [SMILES: CCCCC1CNCCCN1S(=O)(=O)c1cccc2c(O)nccc12]

(1) Preparation of Intermediate

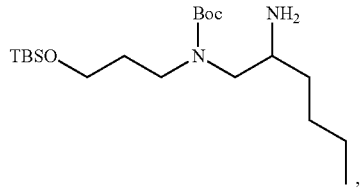 [SMILES: CCCCC(N)CN(CCCO[Si](C)(C)C(C)(C)C)C(=O)OC(C)(C)C]

with synthetic scheme as follows:

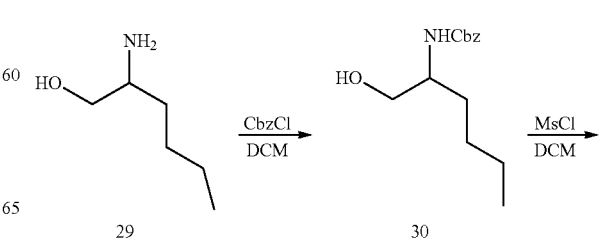

-continued

[Structures shown:
Compound 31: MsO-CH(NHCbz)-butyl chain
+ H₂N-CH₂CH₂CH₂-OH, THF →

Compound 32: HO-propyl-NH-CH(NHCbz)-butyl chain
Boc₂O / DCM →

Compound 33: HO-propyl-N(Boc)-CH(NHCbz)-butyl chain
TBSCl / DCM →

Compound 34: TBSO-propyl-N(Boc)-CH(NHCbz)-butyl chain
H₂, Pd/C / MeOH →

Compound 35: TBSO-propyl-N(Boc)-CH₂-CH(NH₂)-butyl chain]

50 g of 2-aminohexane-1-propanol was weighed and dissolved in 250 mL of dichloromethane solution, then benzyl chloroformate (2.0eq) and triethylamine (3.0eq) were added at 5° C., and then the reaction was carried out under stirring at 15° C. for 8 hours, the resulting reaction solution was extracted with dichloromethane three times, the resulting organic phases were combined and distilled under reduced pressure to obtain a concentrate. The concentrate was separated by column chromatography to obtain a yellow solid benzyl (1-hydroxyhexan-2-yl)carbamate (Compound 30);

50 g of benzyl (1-hydroxyhexan-2-yl)carbamate and 300 mL of dichloromethane were weighed, then methanesulfonyl chloride (1.05eq) and triethylamine (5.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 1:2), the resulting organic phases were combined and distilled under reduced pressure to obtain a concentrate. The concentrate was purified with a normal phase silica gel column, the purified liquid was collected and distilled under reduced pressure to obtain 2-((benzyloxy)carbonyl(amino)hexyl methanesulfonate (Compound 31);

63 g of 2-((benzyloxy)carbonyl(amino)hexyl methanesulfonate was weighed and dissolved in 770 mL of tetrahydrofuran, then 3-aminopropan-1-ol (7.0eq) was added at 15° C., and then the reaction was carried out under stirring at 15° C. for 15 hours. The resulting reaction solution was concentrated under reduced pressure and extracted with hydrochloric acid-ethyl acetate (the volume ratio of hydrochloric acid to ethyl acetate was 5:2) three times. The resulting organic phases were combined, filtered, and concentrated under reduced pressure to obtain a yellow solid benzyl (1-((3-hydroxypropyl)amino)hex-2-yl)carbamate (Compound 32);

50 g of benzyl (1-((3-hydroxypropyl)amino)hex-2-yl)carbamate was weighed and dissolved in 400 mL of dichloromethane, then di-tert-butyl dicarbonate (1.1eq) and triethylamine (3.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 3:8), the resulting organic phases were combined and distilled under reduced pressure to obtain a concentrate. The concentrate was purified with a normal phase silica gel column, the purified liquid was collected and distilled under reduced pressure to obtain tert-butyl (2-((benzyloxy)carbonyl)amino)hexyl(3-hydroxypropyl)carbamate (Compound 33);

65 g of tert-butyl (2-((benzyloxy)carbonyl)amino)hexyl (3-hydroxypropyl)carbamate was weighed and dissolved in 300 mL of dichloromethane, then tert-butyldimethylchlorosilane (1.1eq) and imidazole (3.0eq) were added at 15° C., and then the reaction was carried out under stirring at 15° C. for 15 hours. The resulting reaction solution was extracted with dichloromethane three times, the resulting organic phases were combined and distilled under reduced pressure to obtain a yellow oily substance tert-butyl (2-((benzyloxy)carbonyl)amino)propyl)(3-((tert-butyldimethylsiloxy)propyl)carbamate (Compound 34);

77 g of tert-butyl (2-((benzyloxy)carbonyl)amino)propyl) (3-((tert-butyldimethylsiloxy) propyl)carbamate was weighed and dissolved in 400 mL of methanol, subjected to catalytic hydrogenation by using palladium on carbon as catalyst under stirring at 15° C. for 15 hours. The resulting reaction liquid was concentrated under reduced pressure to obtain a yellow oily substance tert-butyl (2-aminohexyl)(3-((tert-butyldimethylsiloxy)propyl)carbamate (Compound 35).

(2) Preparation of Intermediate

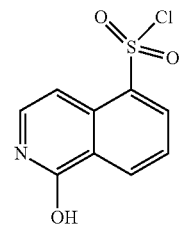

(1-hydroxyisoquinoline-5-sulfonyl chloride)

1 g of 1-hydroxyisoquinoline was weighed and added to 10 mL of chlorosulfonic acid at 10° C. After the addition was completed, the resulting mixture was heated to 120° C. and reacted for 12 hours, then the resulting reaction solution was poured into ice water to form a precipitate, which was filtered, and the filter cake was dried to obtain 1.59 g of crude product 1-hydroxyisoquinoline-5-sulfonyl chloride.

(3) Preparation of Intermediate

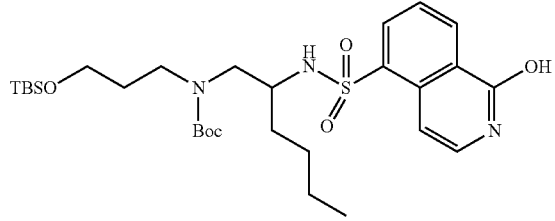 [SMILES: CCCCC(CN(CCCO[Si](C)(C)C(C)(C)C)C(=O)OC(C)(C)C)NS(=O)(=O)c1cccc2c(O)nccc12]

2.6 g of the intermediate

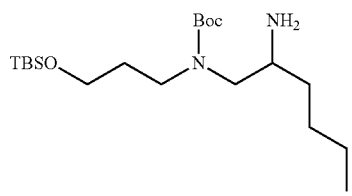 [SMILES: CCCCC(N)CN(CCCO[Si](C)(C)C(C)(C)C)C(=O)OC(C)(C)C]

prepared in step (1) was weighed and dissolved in 25 mL of dichloromethane, then 1-hydroxyisoquinoline-5-sulfonyl chloride prepared in step (2) and 1 ml of triethylamine were added and stirred at room temperature for 4 hours, the resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified with a normal phase silica gel column, the purified liquid was collected and distilled under reduced pressure to obtain 2.6 g of intermediate

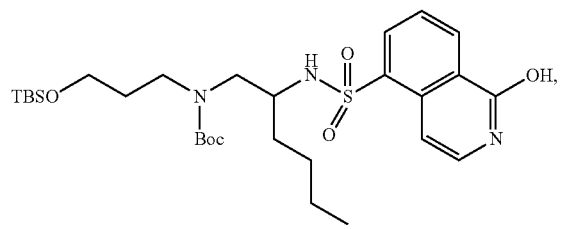 [SMILES: CCCCC(CN(CCCO[Si](C)(C)C(C)(C)C)C(=O)OC(C)(C)C)NS(=O)(=O)c1cccc2c(O)nccc12]

the total yield of step (2) and step (3) was 64%; MS: $[M+1]^+=596.8$.

(4) Preparation of Intermediate

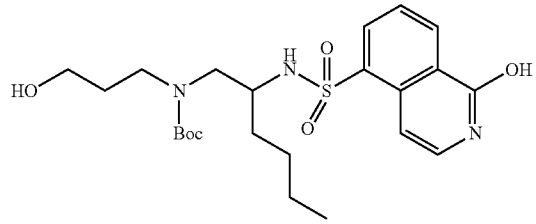 [SMILES: CCCCC(CN(CCCO)C(=O)OC(C)(C)C)NS(=O)(=O)c1cccc2c(O)nccc12]

2.6 g of

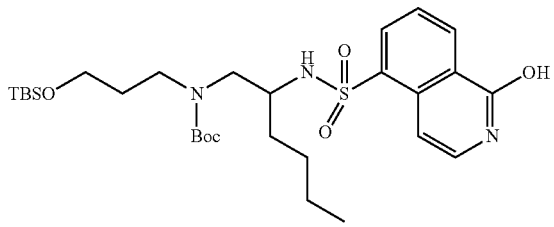 [SMILES: CCCCC(CN(CCCO[Si](C)(C)C(C)(C)C)C(=O)OC(C)(C)C)NS(=O)(=O)c1cccc2c(O)nccc12]

prepared in step (3) was dissolved in 40 mL of tetrahydrofuran, then 1.25 g of TBAF (tetrabutylammonium fluoride) was added and stirred at room temperature for 10 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate. The concentrate was purified through a reverse phase column, the purified liquid was collected and concentrated under reduced pressure to obtain 1.68 g of intermediate

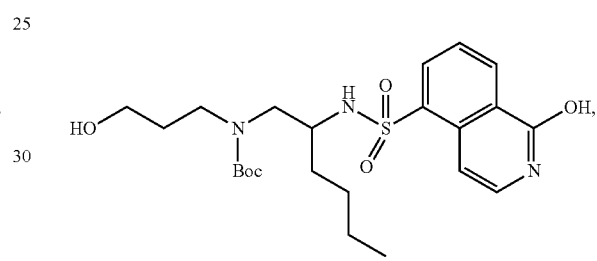

with a yield of 80%; MS: $[M+1]^+=482.6$.

(5) Preparation of Intermediate 5-((N-tert-butoxycarbonyl-2-butyl-1,4-diazacycloheptan-1-yl)sulfonyl)isoquinolin-1-ol

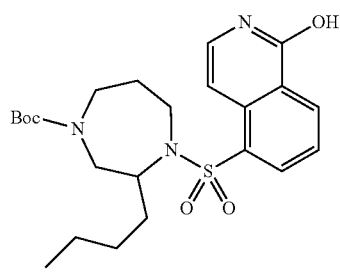 [SMILES: CCCCC1CN(C(=O)OC(C)(C)C)CCCN1S(=O)(=O)c1cccc2c(O)nccc12]

1.68 g of

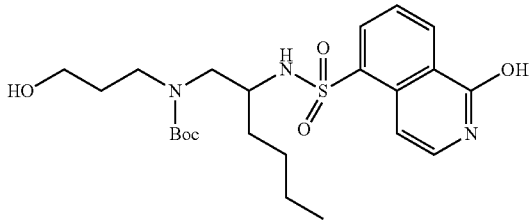 [SMILES: CCCCC(CN(CCCO)C(=O)OC(C)(C)C)NS(=O)(=O)c1cccc2c(O)nccc12]

prepared in step (4) was dissolved in 30 mL of tetrahydrofuran, then 1.09 g of triphenylphosphine was added at 0° C., and 0.84 g of DEAD was added dropwise. After the addition was completed, the resulting mixture was warmed to room temperature and stirred for 12 hours. The resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified through a reverse phase column, and the purified liquid was collected and distilled under reduced pressure to obtain 1.45 g of intermediate 5-((N-tert-butoxycarbonyl-2-butyl-1,4-diazacycloheptan-1-yl)sulfonyl)isoquinolin-1-ol, with a yield of 90%; MS: [M+1]$^+$=464.5.

(6) Preparation of the Target Compound 5-((2-butyl-1,4-diazacycloheptan-1-yl)sulfonyl)isoquinolin-1-ol 1.45 g of 5-((N-tert-butoxycarbonyl-2-butyl-1,4-diazacycloheptan-1-yl)sulfonyl) isoquinolin-1-ol was dissolved in 25 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 1.1 g of the target compound 5-((2-butyl-1,4-diazacycloheptan-1-yl)sulfonyl)isoquinolin-1-ol, with a yield of 96%; MS: [M+1]$^+$=364.1; $^1$H NMR (400 MHz DMSO), 8.49 (d, 1H), 8.38 (d, 1H), 7.58 (t, 1H), 7.31 (d, 1H), 7.12 (d, 1H), 3.97-4.00 (m, 1H), 3.62-3.66 (m, 1H), 3.23-3.26 (m, 1H), 2.99-3.04 (m, 1H), 2.79-2.82 (m, 1H), 2.54-2.66 (m, 1H), 2.51-2.53 (m, 1H), 1.57 (t, 2H)), 1.07-1.09 (m, 2H), 1.03-1.05 (m, 2H), 1.01-1.03 (m, 2H), 0.87 (t, 3H).

Example 14: Preparation of 5-((2-isopentyl-1,4-diazacycloheptan-1-yl)sulfonyl)-1-methoxyisoquinoline, named as YK1612, with structural formula of

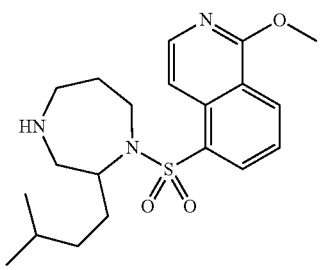 [SMILES: COc1nccc2c(S(=O)(=O)N3CCCNCC3CCC(C)C)cccc12]

(1) Preparation of Intermediate

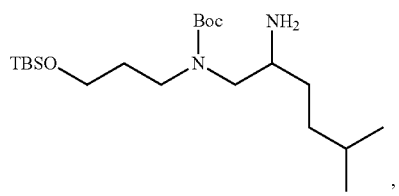 [SMILES: CC(C)CCC(N)CN(CCCO[Si](C)(C)C(C)(C)C)C(=O)OC(C)(C)C]

with synthetic scheme as follows:

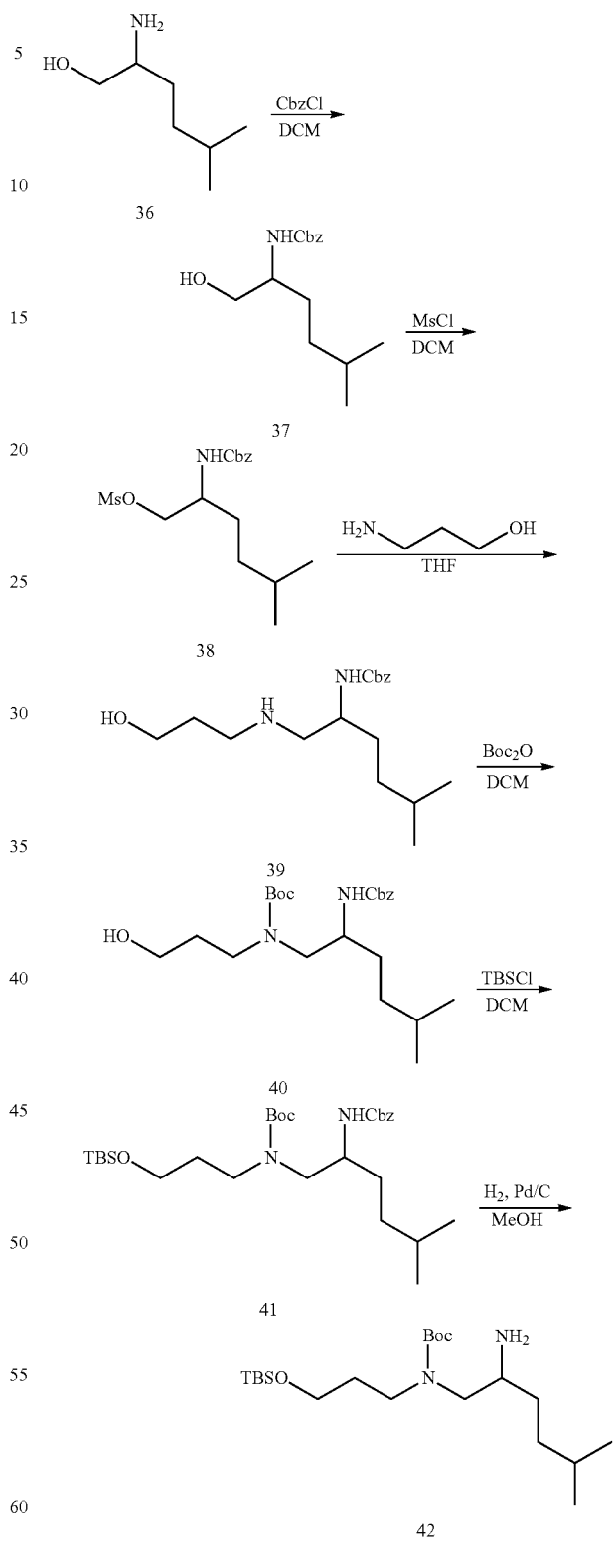

50 g of 2-amino-5-methylhexan-1-ol was weighed and dissolved in 250 mL of dichloromethane solution, benzyl chloroformate (1.0 eq) and triethylamine (3.0eq) were added at 5° C., and then the reaction was carried out under stirring at 15° C. for 8 hours, the resulting reaction solution was extracted with dichloromethane three times, the resulting organic phases were combined and distilled under reduced pressure to obtain a concentrate. The concentrate was separated by column chromatography to obtain a yellow solid benzyl (1-hydroxy-5-methylhexan-2-yl)carbamate (Compound 37);

50 g of benzyl (1-hydroxy-5-methylhexan-2-yl)carbamate and 300 mL of dichloromethane were weighed, then methanesulfonyl chloride (1.05eq) and triethylamine (3.0eq) were added at 15° C., and then the reaction was carried out under stirring at 15° C. for 15 hours. The resulting reaction solution was extracted three times with dichloromethane-saturated brine (the volume ratio of dichloromethane to saturated brine was 1:2), the resulting organic phases were combined and distilled under reduced pressure to obtain a concentrate. The concentrate was purified with a normal phase silica gel column, the purified liquid was collected and distilled under reduced pressure to obtain 2-((benzyloxy)carbonyl)amino)-5-methylhexyl methanesulfonate (Compound 38);

63 g of 2-((benzyloxy)carbonyl)amino)-5-methylhexyl methanesulfonate was weighed and dissolved in 770 mL of tetrahydrofuran, then 3-aminopropan-1-ol (7.0eq) was added at 15° C., and then the reaction was carried out under stirring at 15° C. for 15 hours. The resulting reaction solution was concentrated under reduced pressure and then extracted three times with hydrochloric acid-ethyl acetate (the volume ratio of hydrochloric acid to ethyl acetate was 5:2). The resulting organic phases were combined, filtered, and concentrated under reduced pressure to obtain a yellow solid benzyl (1-((3-hydroxypropyl)amino)-5-methylhexan-2-yl)carbamate (Compound 39);

50 g of benzyl (1-((3-hydroxypropyl)amino)-5-methylhexan-2-yl)carbamate was weighed and dissolved in 400 mL of dichloromethane, then di-tert-butyl dicarbonate (1.5eq) and triethylamine (3.0eq) were added at 15° C., and then the reaction was carried out under stirring at 15° C. for 15 hours. The resulting reaction solution was extracted with dichloromethane-saturated brine (the volume ratio of dichloromethane to saturated brine was 3:8) three times, the resulting organic phases were combined and distilled under reduced pressure to obtain a concentrate. The concentrate was purified with a normal phase silica gel column, the purified liquid was collected and distilled under reduced pressure to obtain tert-butyl (2-((benzyloxy)carbonyl)amino)-5-methylhexyl(3-hydroxypropyl)carbamate (Compound 40);

65 g of tert-butyl (2-((benzyloxy)carbonyl)amino)-5-methylhexyl(3-hydroxypropyl)carbamate was weighed and dissolved in 300 mL of dichloromethane, then tert-butyl dimethylchlorosilane (1.1eq) and imidazole (2.0eq) were added at 15° C., and then the reaction was carried out under stirring at 15° C. for 15 hours. The resulting reaction liquid was extracted three times with dichloromethane, the resulting organic phases were combined and distilled under reduced pressure to obtain a yellow oily substance tert-butyl(2-((benzyloxy)carbonyl)amino)-5-methylhexyl)(3-((tert-butyldimethylsiloxy)propyl)carbamate (Compound 41);

77 g of tert-butyl(2-((benzyloxy)carbonyl)amino)-5-methylhexyl)(3-((tert-butyldimethylsiloxy)propyl)carbamate was weighed and dissolved in 400 mL of methanol, subjected to catalytic hydrogenation by using palladium on carbon as catalyst under stirring at 15° C. 15 hours. The resulting reaction liquid was concentrated under reduced pressure to obtain a yellow oily substance tert-butyl (2-amino-5-methylhexyl)(3-((tert-butyldimethylsiloxy)propyl)carbamate (Compound 42).

(2) Preparation of Intermediate 1-methoxyisoquinoline-5-sulfonyl chloride

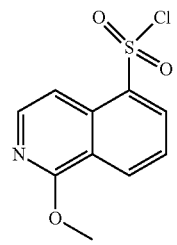 [SMILES: COc1nccc2c(S(=O)(=O)Cl)cccc12]

1 g of 1-methoxyisoquinoline was weighed and added to 10 mL of chlorosulfonic acid at 10° C. After the addition was completed, the resulting mixture was heated to 130° C. and reacted for 12 hours, then the resulting reaction solution was poured into ice water to form a precipitate, which was filtered, and the filter cake was dried to obtain 1.48 g of crude product 1-methoxyisoquinoline-5-sulfonyl chloride.

(3) Preparation of Intermediate

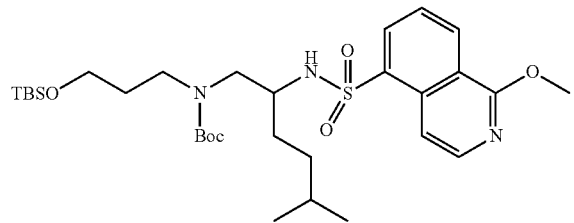 [SMILES: COc1nccc2c(S(=O)(=O)NC(CCC(C)C)CN(CCCO[Si](C)(C)C(C)(C)C)C(=O)OC(C)(C)C)cccc12]

2.5 g of the intermediate

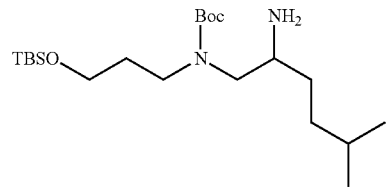 [SMILES: CC(C)CCC(N)CN(CCCO[Si](C)(C)C(C)(C)C)C(=O)OC(C)(C)C]

prepared in step (1) was weighed and dissolved in 25 mL of dichloromethane, then 1-methoxyisoquinoline-5-sulfonyl chloride prepared in step (2) and 1 ml of triethylamine were added and stirred at room temperature for 4 hours. The resulting reaction solution was extracted three times with dichloromethane-saturated brine (the volume ratio of dichloromethane to saturated brine was 6:10), the resulting organic phases were combined and distilled under reduced pressure to obtain a concentrate. The concentrate was purified with a normal phase silica gel column, the purified liquid was collected and distilled under reduced pressure to obtain 2.67 g of intermediate

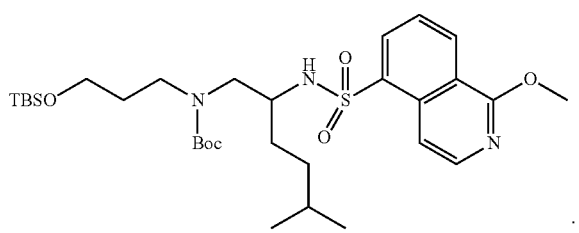 [SMILES: COc1nccc2c(S(=O)(=O)NC(CCC(C)C)CN(CCCO[Si](C)(C)C(C)(C)C)C(=O)OC(C)(C)C)cccc12]

The total yield of step (2) and step (3) was 67%; MS: [M+1]$^+$=624.9.

(4) Preparation of Intermediate

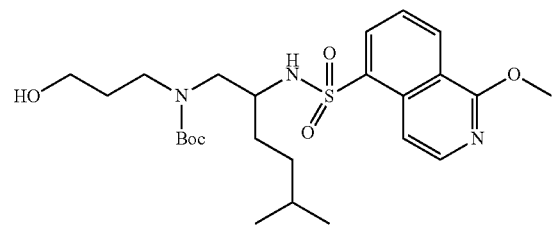 [SMILES: COc1nccc2c(S(=O)(=O)NC(CCC(C)C)CN(CCCO)C(=O)OC(C)(C)C)cccc12]

2.67 g of

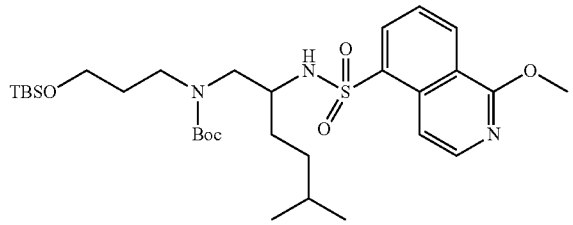 [SMILES: COc1nccc2c(S(=O)(=O)NC(CCC(C)C)CN(CCCO[Si](C)(C)C(C)(C)C)C(=O)OC(C)(C)C)cccc12]

prepared in step (3) was dissolved in 35 mL of tetrahydrofuran, then 1.34 g of TBAF (tetrabutylammonium fluoride) was added and stirred at room temperature for 12 hours, the resulting reaction solution was extracted with dichloromethane-saturated brine (the volume ratio of dichloromethane to saturated brine was 6:10) three times, the resulting organic phases were collected and distilled under reduced pressure to obtain a concentrate. The concentrate was purified through a reverse phase column, the purified liquid was collected and concentrated under reduced pressure to obtain 1.87 g of intermediate

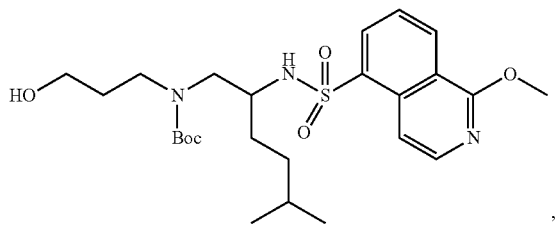 [SMILES: COc1nccc2c(S(=O)(=O)NC(CCC(C)C)CN(CCCO)C(=O)OC(C)(C)C)cccc12]

with a yield of 86%; MS: [M+1]$^+$=510.6.

(5) Preparation of Intermediate 5-((N-tert-butoxycarbonyl-2-isopentyl-1,4-diazacycloheptan-1-yl)sulfonyl)-1-methoxyisoquinoline

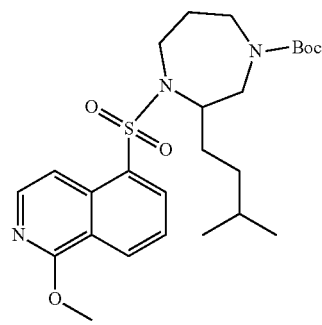 [SMILES: COc1nccc2c(S(=O)(=O)N3CCCN(C(=O)OC(C)(C)C)CC3CCC(C)C)cccc12]

1.87 g of

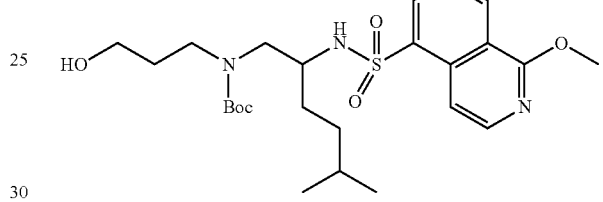

prepared in step (4) was dissolved in 30 mL of tetrahydrofuran, then 1.25 g of triphenylphosphine was added at 0° C., and then 0.96 g of DIAD was added dropwise. After the addition was completed, the resulting mixture was warmed to room temperature and stirred for 12 hours. The resulting reaction solution was extracted with dichloromethane-saturated brine (the volume ratio of dichloromethane to saturated brine was 6:10) three times, the resulting organic phases were combined and distilled under reduced pressure to obtain a concentrate. The concentrate was purified through a reverse phase column, the purified liquid was collected and distilled under reduced pressure to obtain 1.56 g of intermediate 5-((N-tert-butoxycarbonyl-2-isopentyl-1,4-diazacycloheptan-1-yl)sulfonyl)-1-methoxyisoquine, with a yield of 87%; MS: [M+1]$^+$=492.6.

(6) Preparation of Target Compound 5-((2-isopentyl-1,4-diazacycloheptan-1-yl)sulfonyl)-1-methoxyisoquinoline 1.56 g of 5-((N-tert-butoxycarbonyl-2-isopentyl-1,4-diazacycloheptan-1-yl)sulfonyl)-1-methoxyisoquinoline was dissolved in 25 mL of 4M HCl(g) in dioxane solution, stirred at room temperature for 2 hours, and distilled under reduced pressure to remove the solvent and obtain a concentrate. The concentrate was purified through a reverse phase column with ammonium bicarbonate aqueous solution-methanol (the volume ratio of ammonium bicarbonate aqueous solution to methanol was 4:6, in which the concentration of ammonium bicarbonate aqueous solution was 10 mmol/L) as mobile phase, the purified liquid was collected and distilled under reduced pressure to obtain 1.18 g of the target compound 5-((2-isopentyl-1,4-diazacycloheptan-1-yl)sulfonyl)-1-methoxyisoquinoline, with a yield of 95%; MS: [M+1]$^+$=392.1; $^1$H NMR (400 MHz DMSO), 8.51 (d, 1H), 8.41 (d, 1H), 8.17 (d, 1H), 7.87 (d, 1H), 7.72 (t, 1H), 4.06 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 1.08-1.10 (m, 2H), 0.91-0.93 (m, 2H), 0.87-0.89 (m, 1H), 0.82 (d, 6H).

Example 15: Preparation of R Configuration Optical Isomers of the Target Compounds of Examples 1 to 14

The racemic target compounds prepared in Examples 1 to 14 were subjected to chiral resolution (exemplarily, resolution by chiral column) to obtain their R configuration optical isomers and S configuration optical isomers. Alternatively, chiral starting materials were used to prepare the R configuration optical isomers of the target compounds of Examples 1 to 14 according to the preparation methods (including amount relationships of materials, reaction conditions, etc.) of Examples 1 to 14.

The specific structural formulas, chemical names, and corresponding spectrum analysis of the R configuration optical isomers of the target compounds of Examples 1 to 14 were as follows:

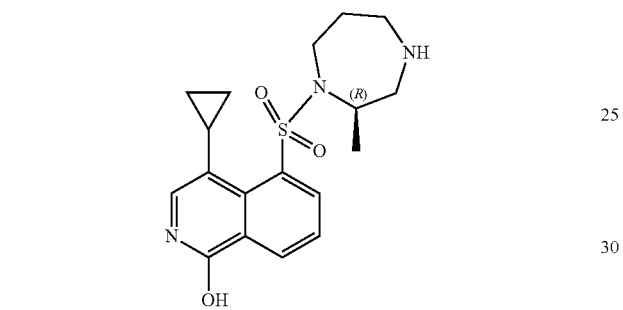

(R)-4-cyclopropyl-5-((2-methyl-1,4-diazacycloheptan-1-yl)sulfonyl)isoquinolin-1-ol, named as R-YK1600-1; its synthetic scheme was as follows:

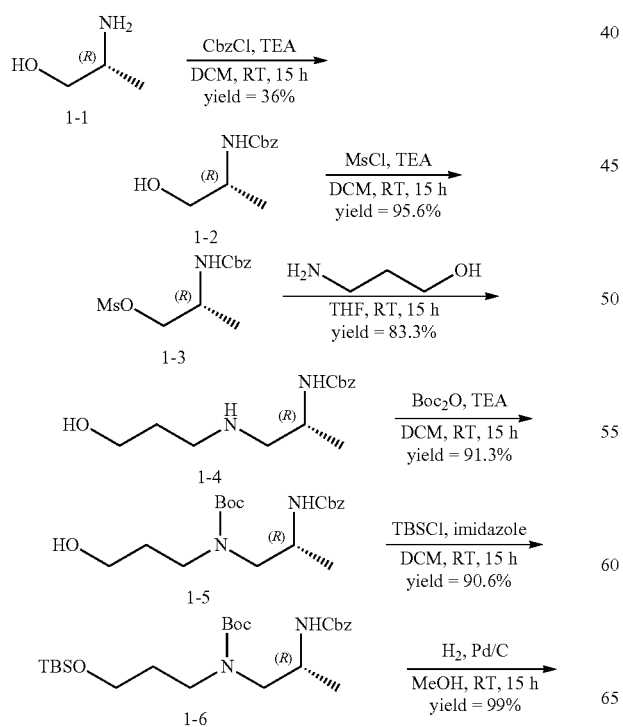

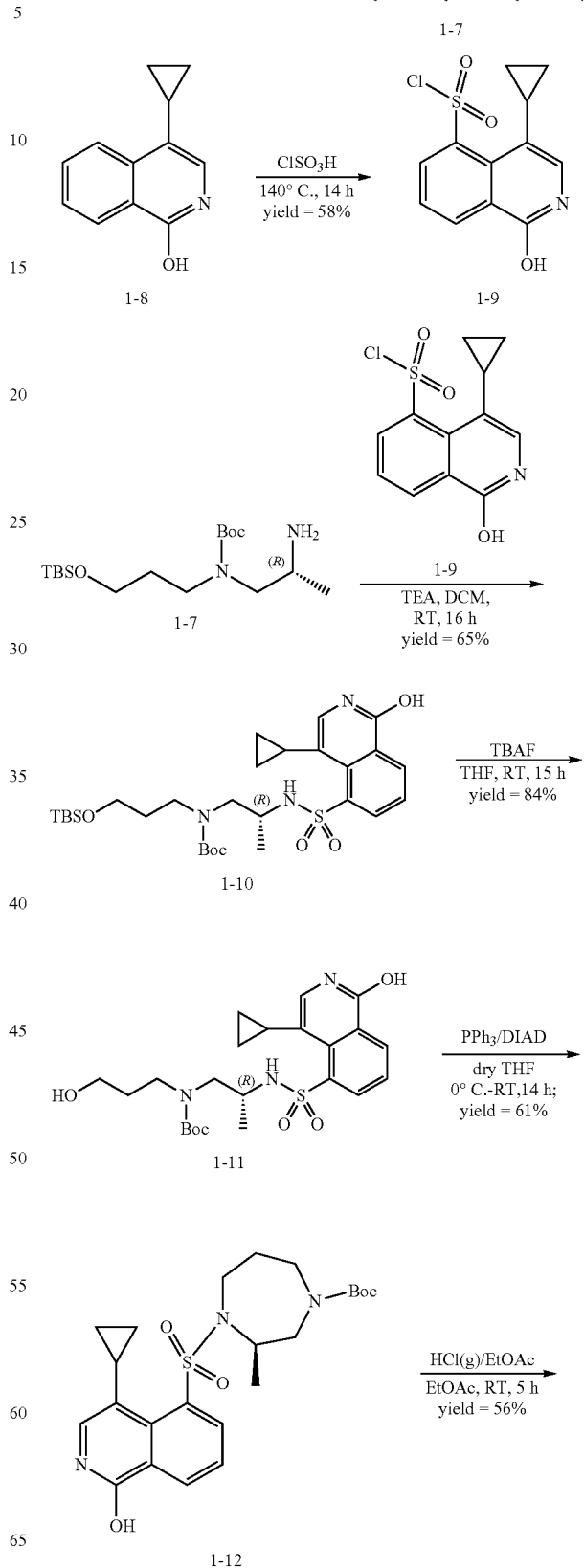

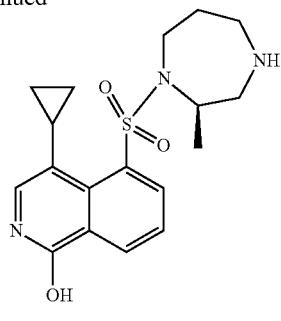

R-YK1600-1

R-YK1600-1 had MS: [M+1]$^+$=362.1; $^1$H NMR (400 MHz DMSO), 8.48 (d, 1H), 8.37 (d, 1H), 7.59 (t, 1H), 7.33 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 1.49-1.51 (m, 1H), 0.97-0.99 (m, 4H), 0.93 (d, 3H).

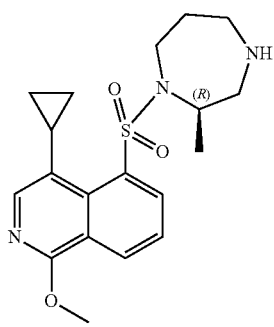

(R)-4-cyclopropyl-1-methoxy-5-((2-methyl-1,4-diazacycloheptan-1-yl)sulfonyl)isoquinoline, named as R-YK1600-2; its synthetic scheme was as follows:

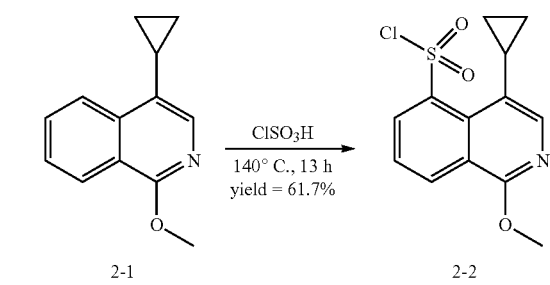

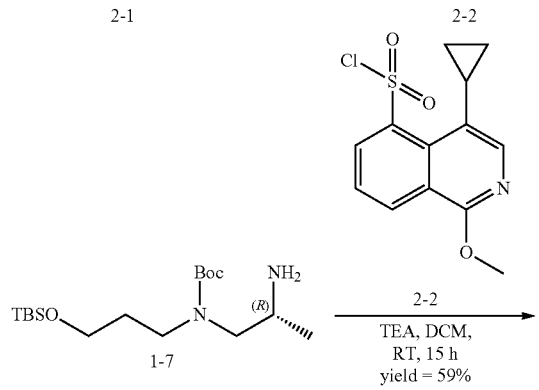

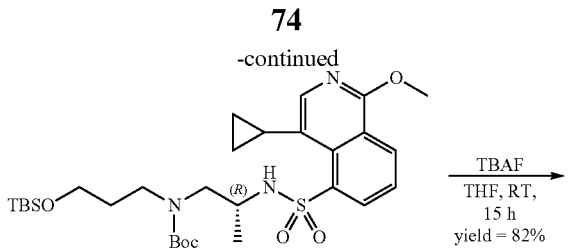

2-3

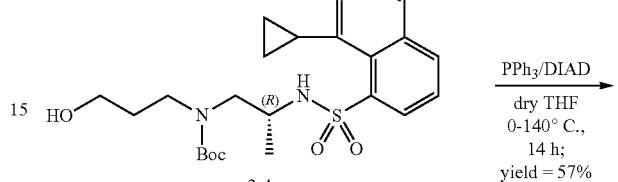

2-4

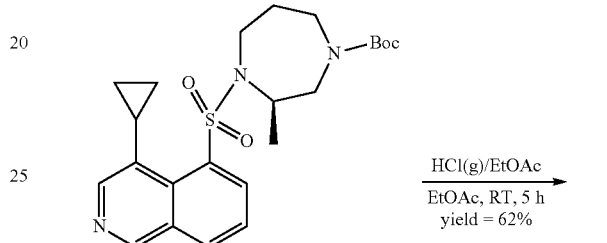

2-5

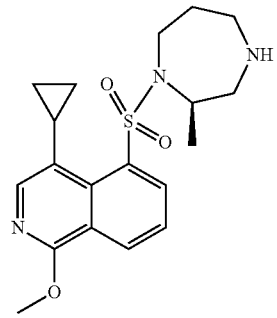

R-YK1600-2

R-YK1600-2 had MS: [M+1]$^+$=322.1; $^1$H NMR (400 MHz DMSO), 8.48 (d, 1H), 8.37 (d, 1H), 7.59 (t, 1H), 7.33 (d, 1H), 4.05 (s, 3H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 1.49-1.51 (m, 1H), 0.97-0.99 (m, 4H), 0.93 (d, 3H).

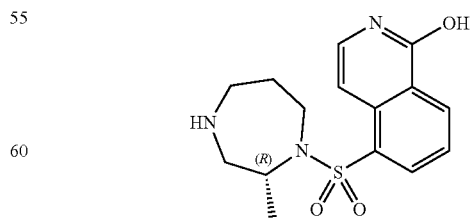

(R)-5-((2-methyl-1,4-diazacycloheptan-1-yl)sulfonyl)isoquinolin-1-ol, named as R-YK1601; its synthetic scheme was as follows:

75
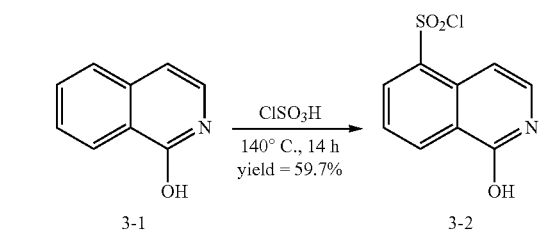
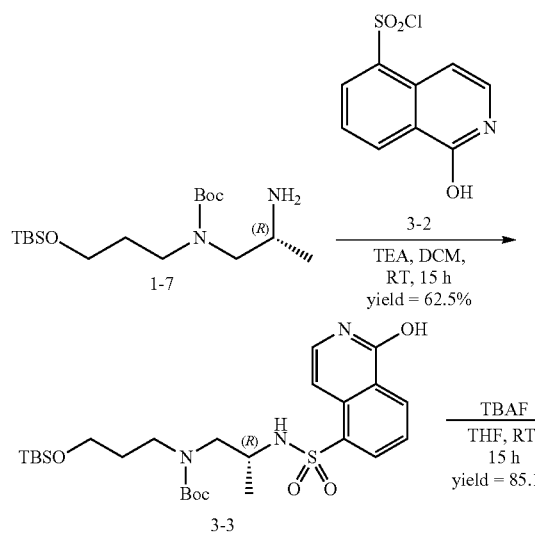
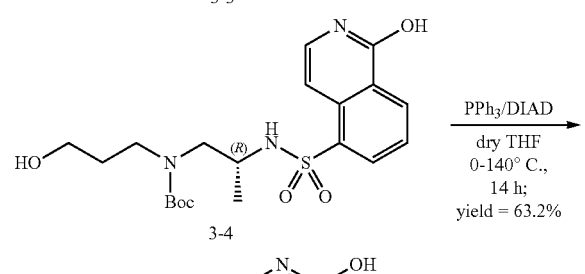
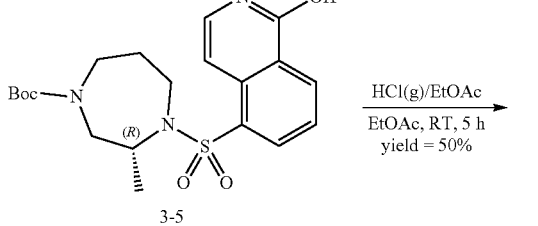
MS: [M+1]$^+$=322.1; $^1$H NMR (400 MHz DMSO), 8.48 (d, 1H), 8.37 (d, 1H), 7.59 (t, 1H), 7.33 (d, 1H), 7.11 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.93 (d, 3H).
76
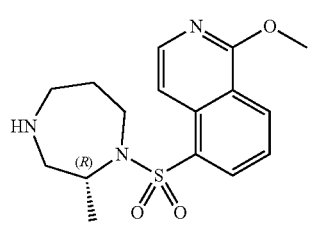
(R)-1-methoxy-5-((2-methyl-1,4-diazacycloheptan-1-yl)sulfonyl)isoquinoline, named as R-YK1602; its synthetic scheme was as follows:
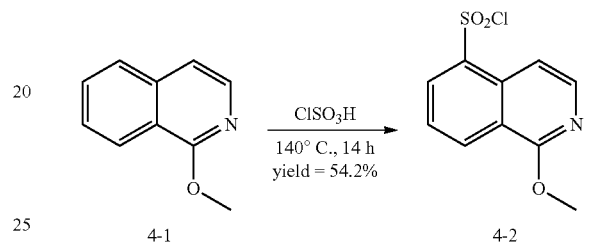
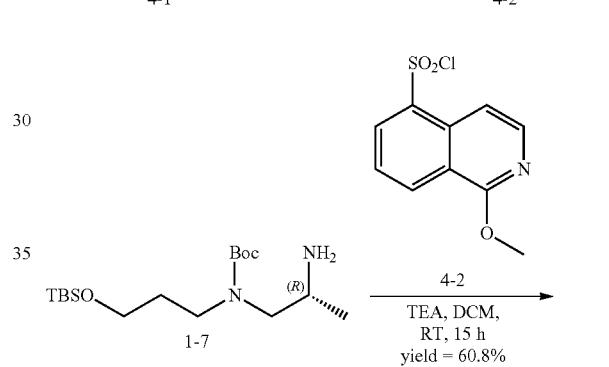
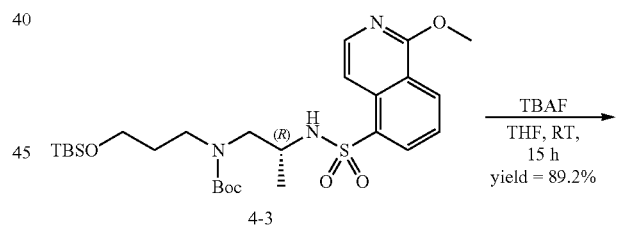
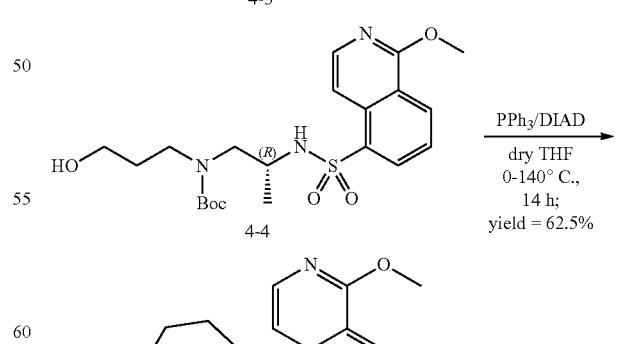

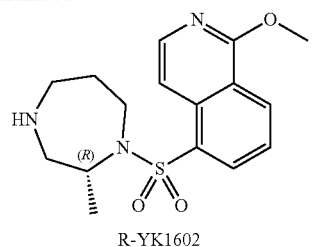
R-YK1602
R-YK1602 had MS: [M+1]⁺=336.2; ¹H NMR (400 MHz DMSO), 8.46-8.54 (m, 2H), 8.19 (d, 1H), 7.88 (d, 1H), 7.74 (t, 1H), 4.08 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 0.84 (t, 3H).
(R)-5-((2-methyl-1,4-diazacycloheptan-1-yl)sulfonyl)isoquinoline, named as R-YK1603; its synthetic scheme was as follows:
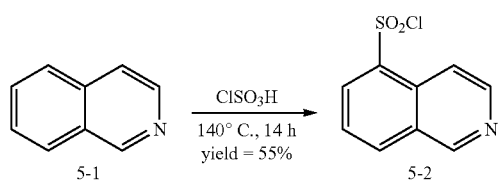
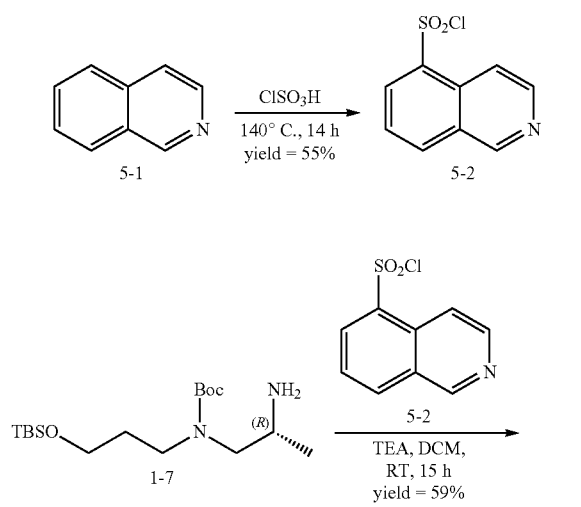
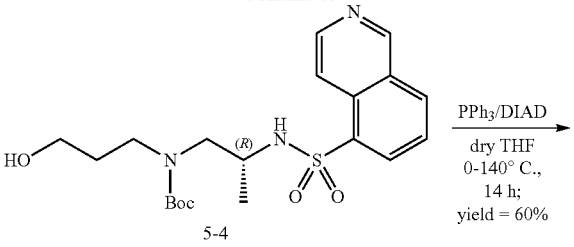
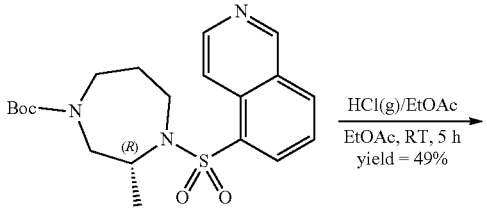
R-YK1603
R-YK1603 had MS: [M+1]⁺=306.1; ¹H NMR (400 MHz DMSO), 8.89 (s, 1H), 8.48 (d, 1H), 8.37 (d, 1H), 7.59 (t, 1H), 7.33 (d, 1H), 7.11 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.93 (d, 3H).
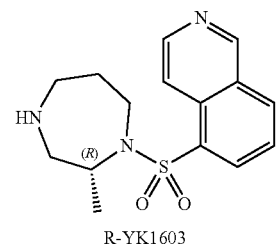
(R)-4-fluoro-5-((2-methyl-1,4-diazacycloheptan-1-yl)sulfonyl)isoquinolin-1-ol, named as R-YK1604; its synthetic scheme was as follows:
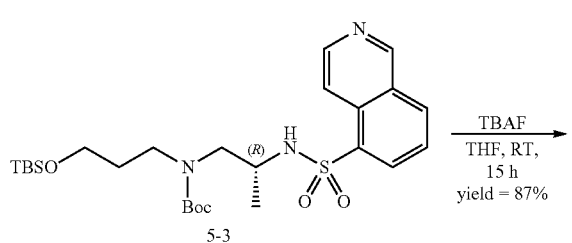
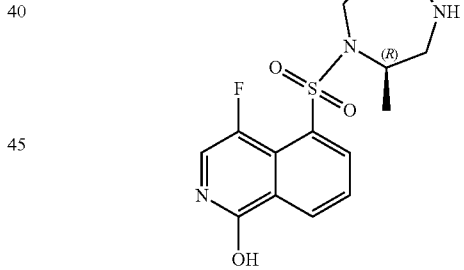

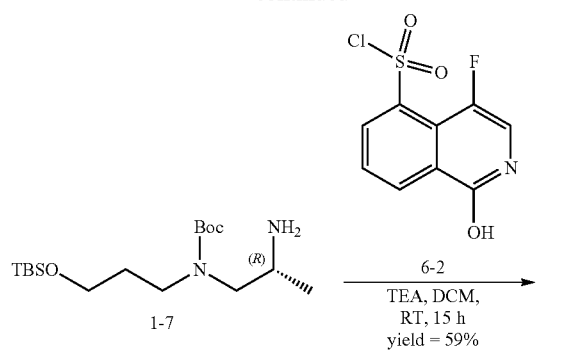
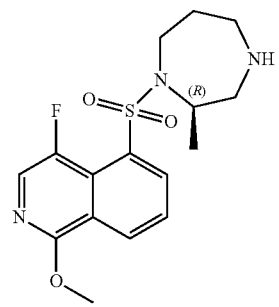
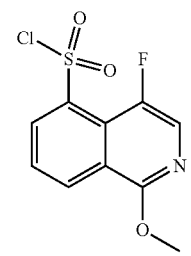
R-YK1604
R-YK1604 had MS: [M+1]$^+$=340.1; $^1$H NMR (400 MHz DMSO), 8.48 (d, 1H), 8.37 (d, 1H), 7.59 (t, 1H), 7.33 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.93 (d, 3H).
(R)-4-fluoro-1-methoxy-5-((2-methyl-1,4-diazacycloheptan-1-yl)sulfonyl)isoquinoline, named as R-YK1605; its synthetic scheme was as follows:
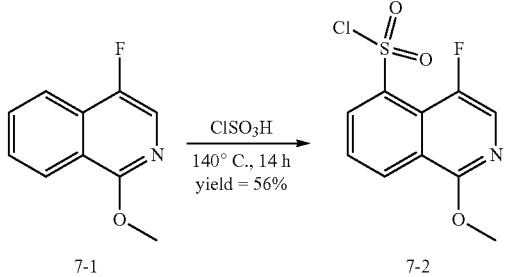
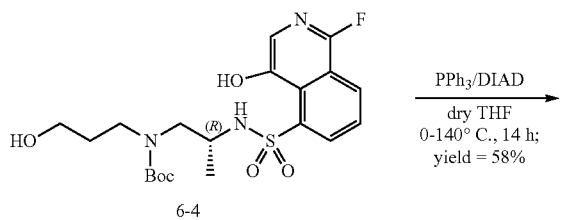
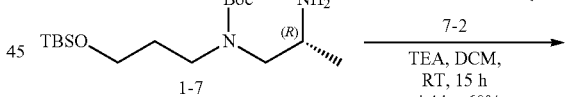
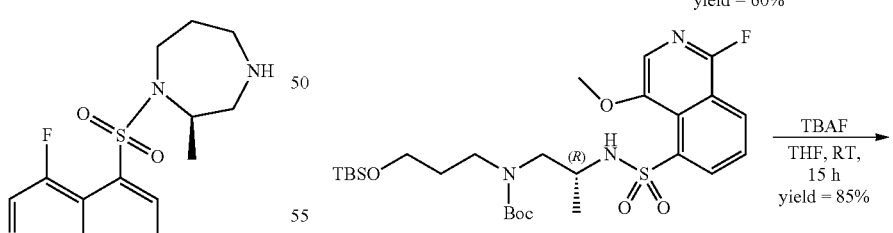
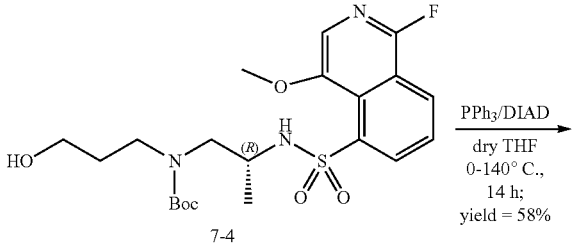

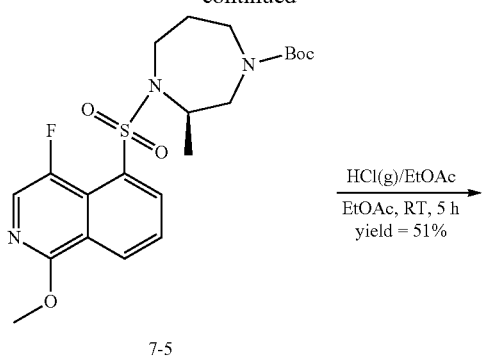
7-5
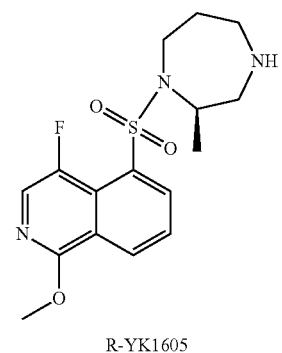
R-YK1605
R-YK1605 had MS: [M+1]$^+$=354.1; $^1$H NMR (400 MHz DMSO), 8.52 (d, 1H), 8.19 (d, 1H), 7.88 (d, 1H), 7.74 (t, 1H), 4.07 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 0.84 (t, 3H).
(R)-4-chloro-5-((2-methyl-1,4-diazacycloheptan-1-yl)sulfonyl)isoquinolin-1-ol, named as R-YK1606; its synthetic scheme was as follows:
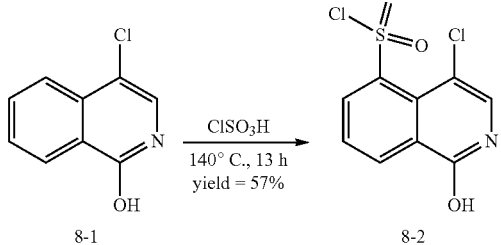
8-1  8-2
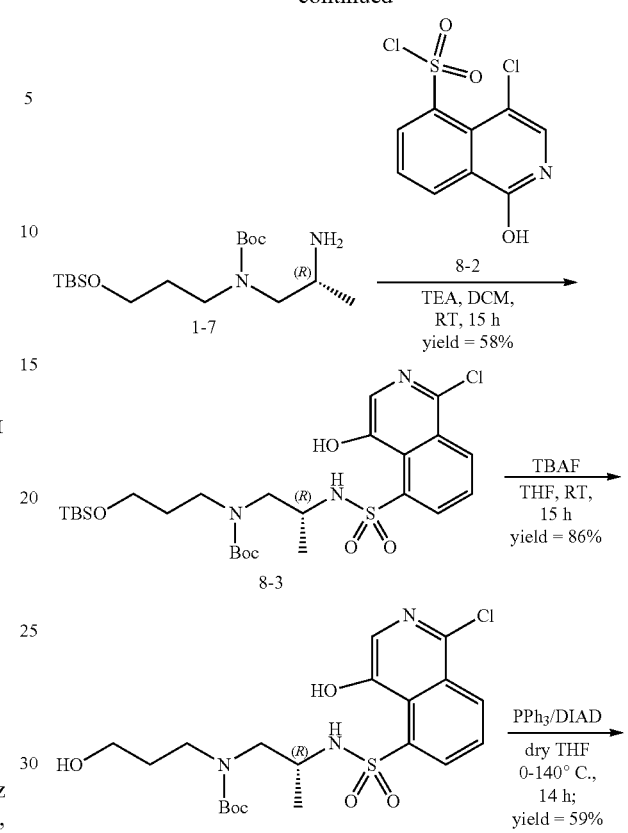
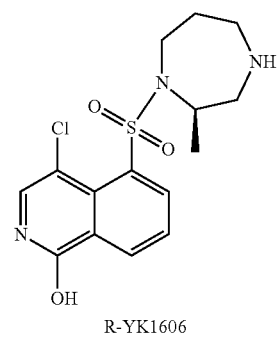
R-YK1606
R-YK1606 had MS: [M+1]$^+$=356.1; $^1$H NMR (400 MHz DMSO), 8.48 (d, 1H), 8.37 (d, 1H), 7.59 (t, 1H), 7.33 (d, 1H), 3.97-4.00 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.56 (t, 2H), 0.92 (d, 3H).

83
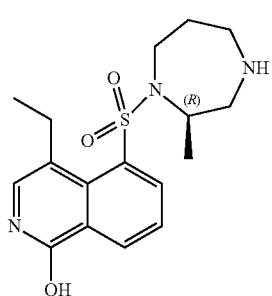
(R)-4-ethyl-5-((2-methyl-1,4-diazacycloheptan-1-yl)sulfonyl)isoquinolin-1-ol, named as R-YK1607; its synthetic scheme was as follows:
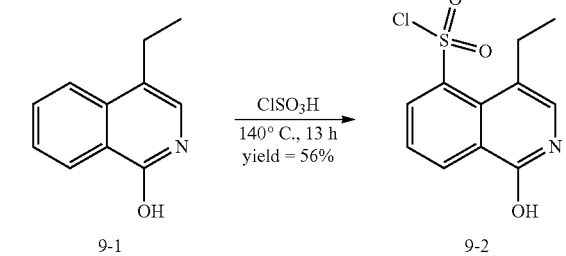
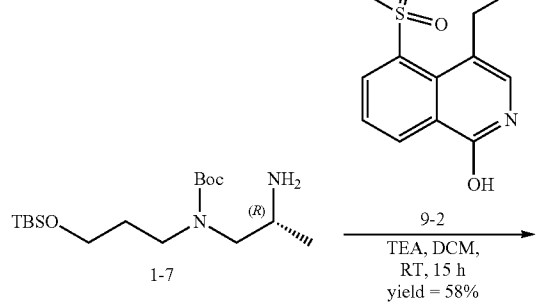
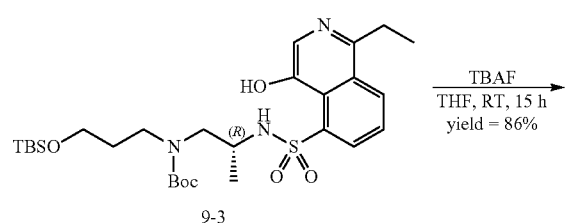
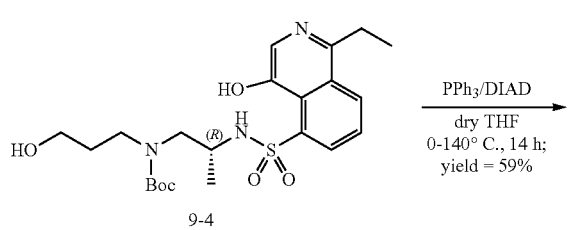
84
-continued
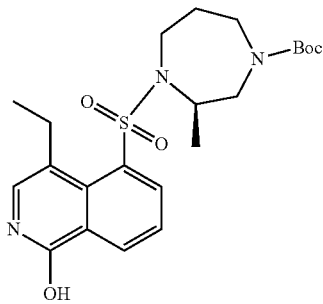
9-5
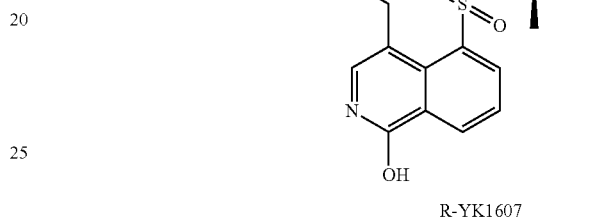
R-YK1607
R-YK1607 had MS: [M+1]$^+$=350.1; $^1$H NMR (400 MHz DMSO), 8.38 (s, 1H), 8.27 (d, 1H), 7.51 (t, 1H), 7.23 (d, 1H), 3.99-4.02 (m, 1H), 3.61-3.65 (m, 1H), 3.22-3.25 (m, 1H), 2.99-3.04 (m, 1H), 2.79-2.82 (m, 1H), 2.53-2.64 (m, 1H), 2.51-2.53 (m, 1H), 2.43 (q, 2H), 1.52 (t, 2H), 1.18 (t, 3H), 0.90 (d, 3H).
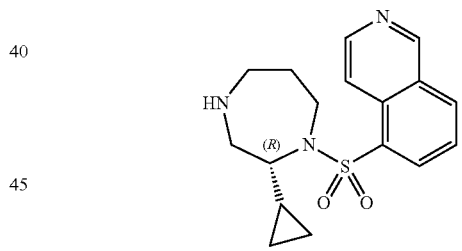
(R)-5-((2-cyclopropyl-1,4-diazacycloheptan-1-yl)sulfonyl)isoquinoline, named as R-YK1608; its synthetic scheme was as follows:
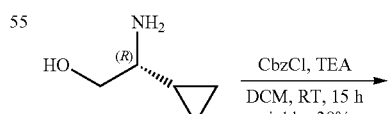
10-1
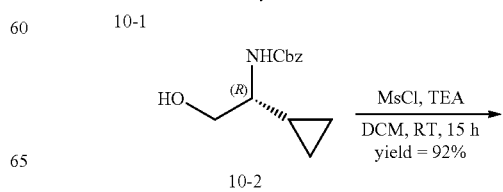
10-2

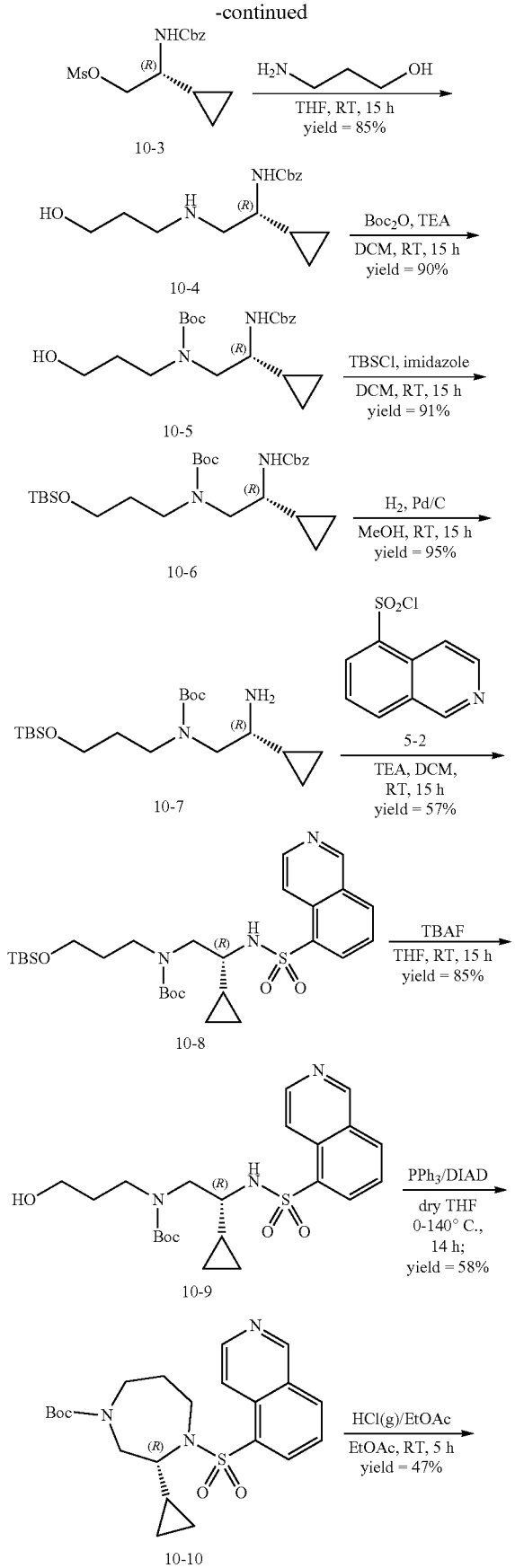
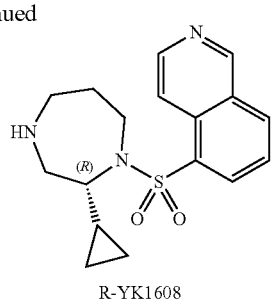
R-YK1608
R-YK1608 had MS: [M+1]$^+$=332.1; $^1$H NMR (400 MHz DMSO), 8.78 (s, 1H), 8.47 (d, 1H), 8.32 (d, 1H), 7.58 (t, 1H), 7.32 (d, 1H), 7.13 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.55 (t, 2H), 0.61-0.63 (m, 1H), 0.47-0.50 (m, 4H).
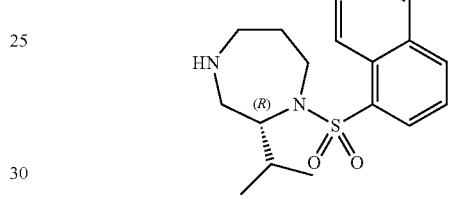
(R)-5-((2-isopropyl-1,4-diazacycloheptan-1-yl)sulfonyl)isoquinolin-1-ol, named as R-YK1609; its synthetic scheme was as follows:
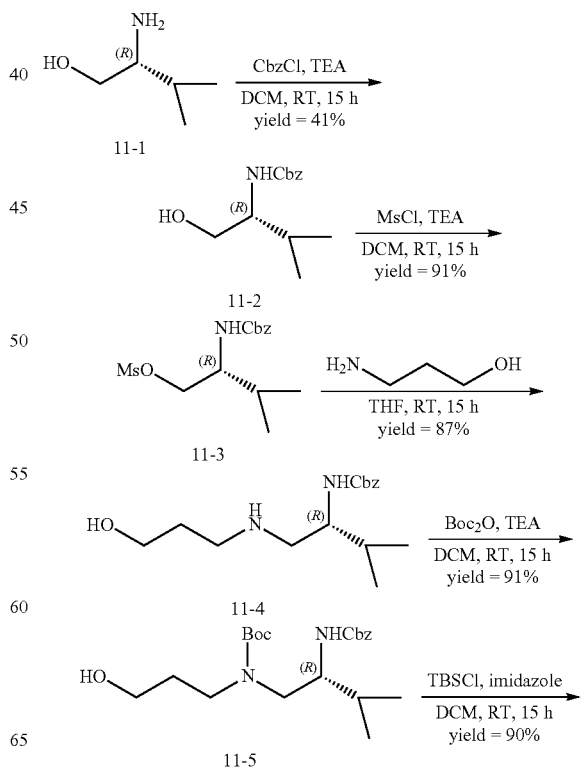

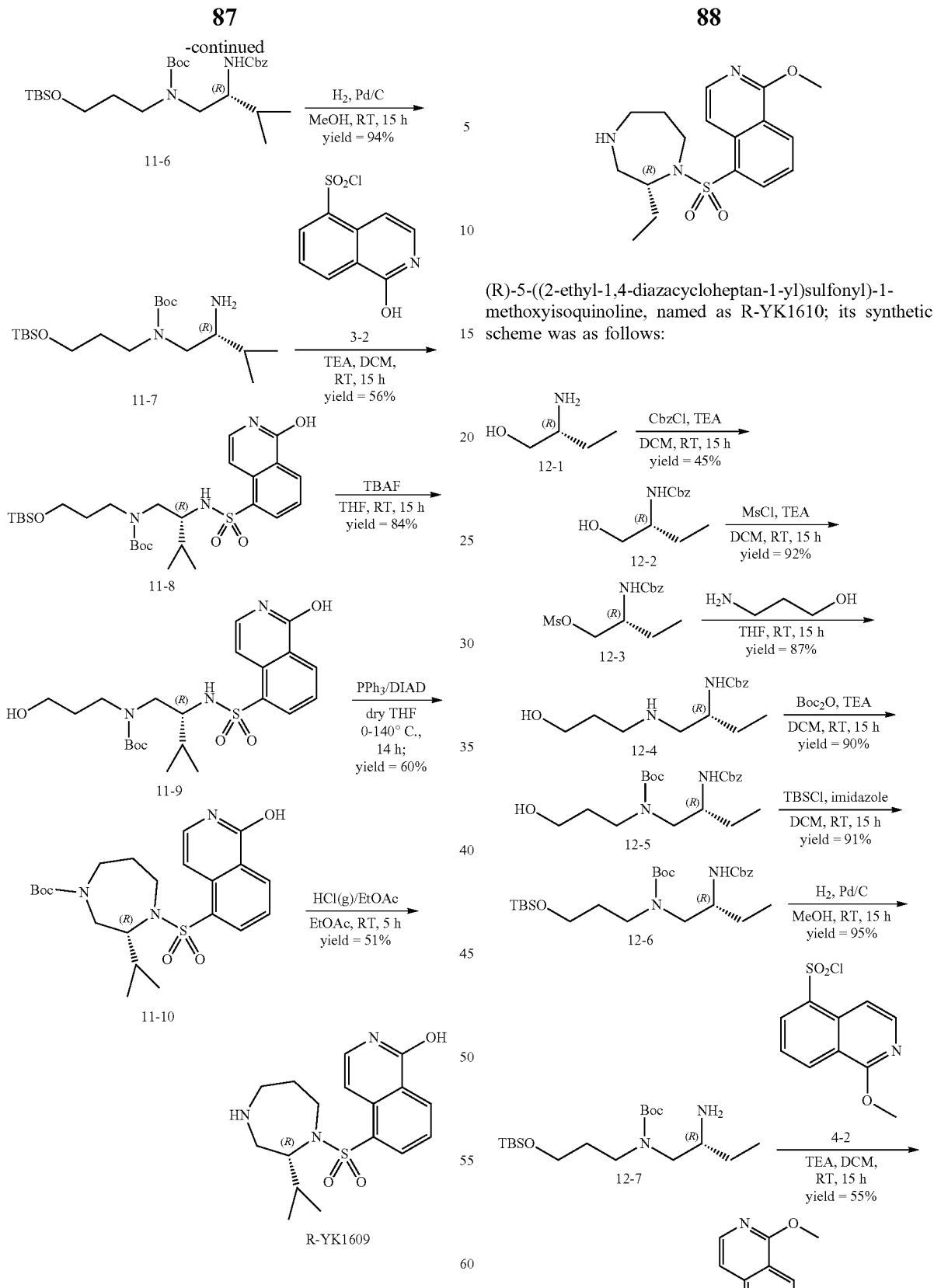
(R)-5-((2-ethyl-1,4-diazacycloheptan-1-yl)sulfonyl)-1-methoxyisoquinoline, named as R-YK1610; its synthetic scheme was as follows:
R-YK1609 had MS: [M+1]$^+$=350.1; H NMR (400 MHz DMSO), 8.45 (d, 1H), 8.32 (d, 1H), 7.54 (t, 1H), 7.29 (d, 1H), 7.09 (d, 1H), 3.98-4.01 (m, 1H), 3.61-3.65 (m, 1H), 3.22-3.25 (m, 1H), 2.99-3.04 (m, 1H), 2.79-2.82 (m, 1H), 2.54-2.66 (m, 1H), 2.53-2.54 (m, 1H), 1.52 (t, 2H), 0.90-0.91 (m, 1H), 0.85 (d, 9H).

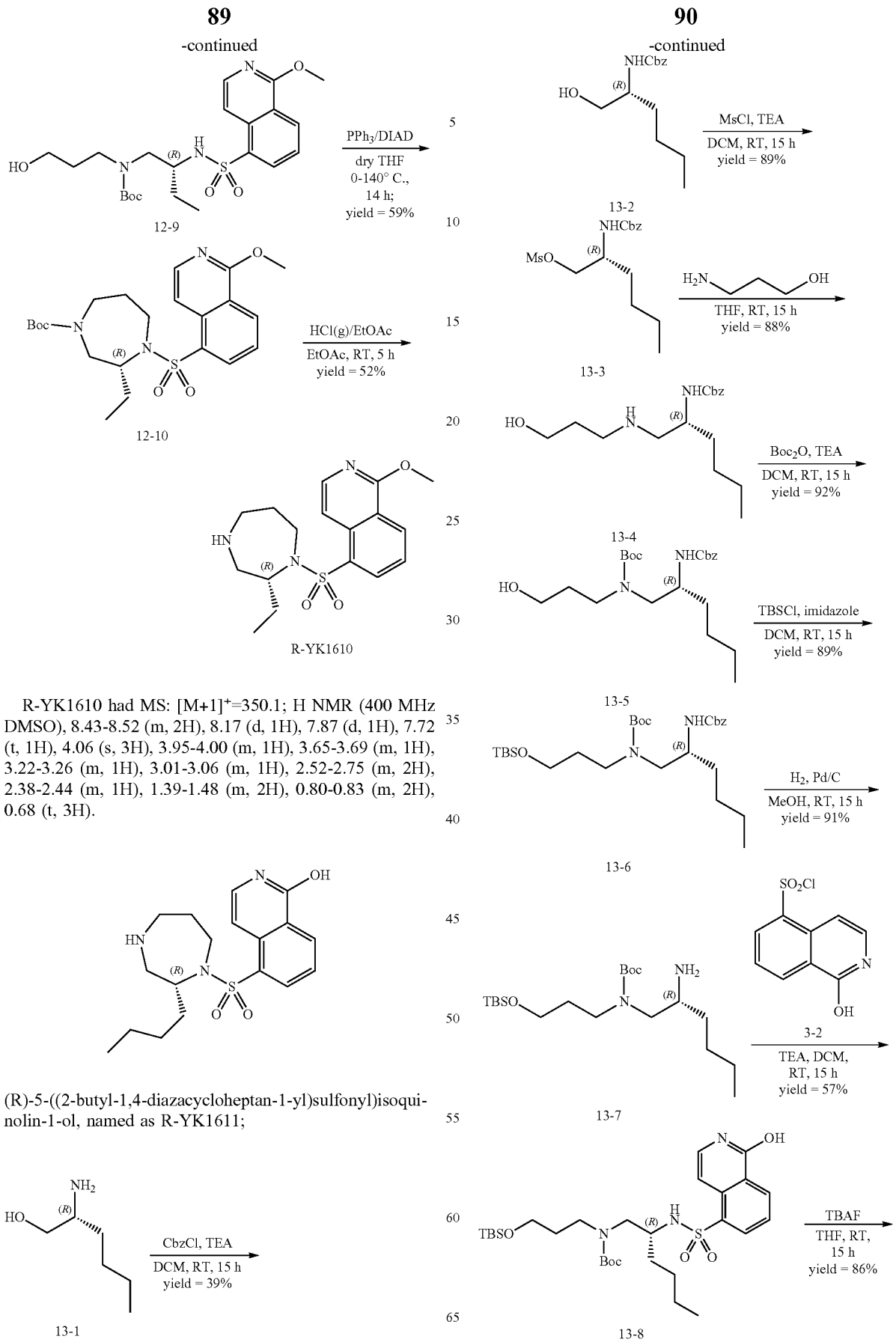
R-YK1610 had MS: [M+1]$^+$=350.1; H NMR (400 MHz DMSO), 8.43-8.52 (m, 2H), 8.17 (d, 1H), 7.87 (d, 1H), 7.72 (t, 1H), 4.06 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 0.80-0.83 (m, 2H), 0.68 (t, 3H).
(R)-5-((2-butyl-1,4-diazacycloheptan-1-yl)sulfonyl)isoquinolin-1-ol, named as R-YK1611;

-continued
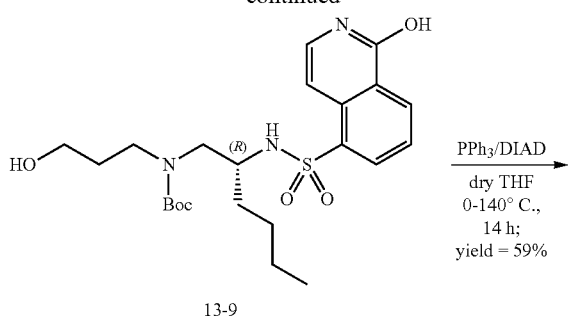
13-9
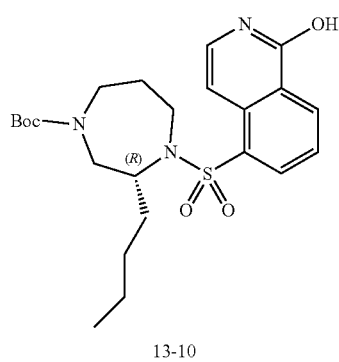
13-10
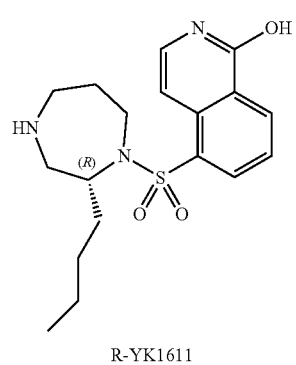
R-YK1611
R-YK1611 had MS: [M+1]$^+$=364.1; H NMR (400 MHz DMSO), 8.49 (d, 1H), 8.38 (d, 1H), 7.58 (t, 1H), 7.31 (d, 1H), 7.12 (d, 1H), 3.97-4.00 (m, 1H), 3.62-3.66 (m, 1H), 3.23-3.26 (m, 1H), 2.99-3.04 (m, 1H), 2.79-2.82 (m, 1H), 2.54-2.66 (m, 1H), 2.51-2.53 (m, 1H), 1.57 (t, 2H), 1.07-1.09 (m, 2H), 1.03-1.05 (m, 2H), 1.01-1.03 (m, 2H), 0.87 (t, 3H).
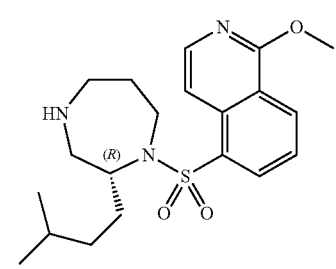
(R)-5-((2-isopentyl-1,4-diazacycloheptan-1-yl)sulfonyl)-1-methoxyisoquinoline, named as R-YK1612; its synthesis scheme was as follows:
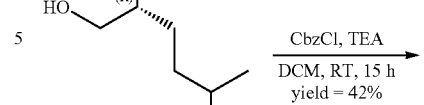
14-1
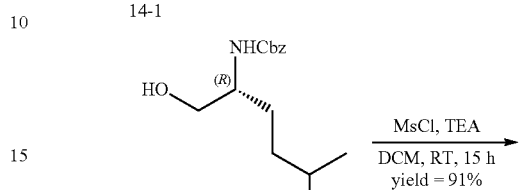
14-2
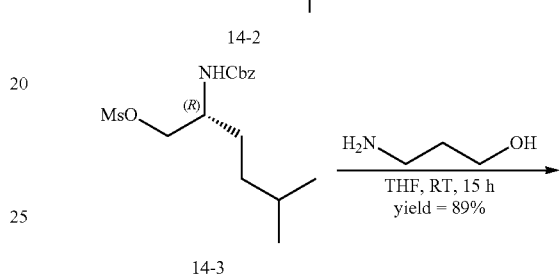
14-3
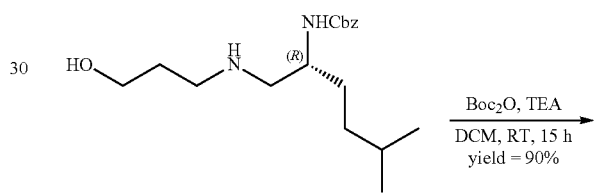
14-4
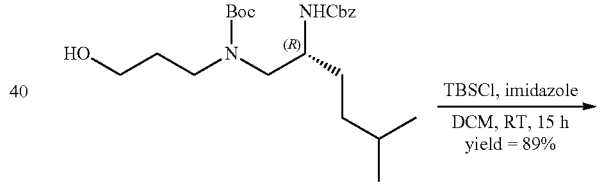
14-5
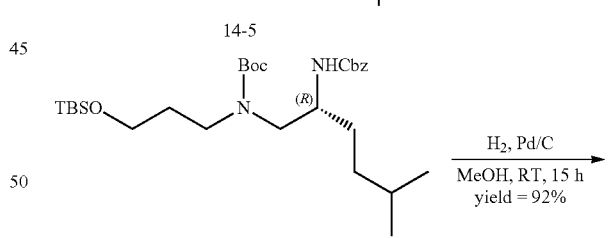
14-6
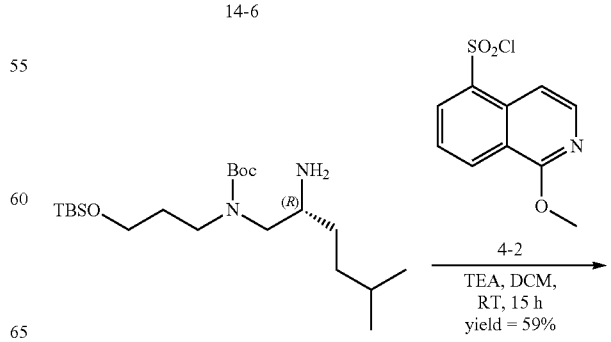
14-7

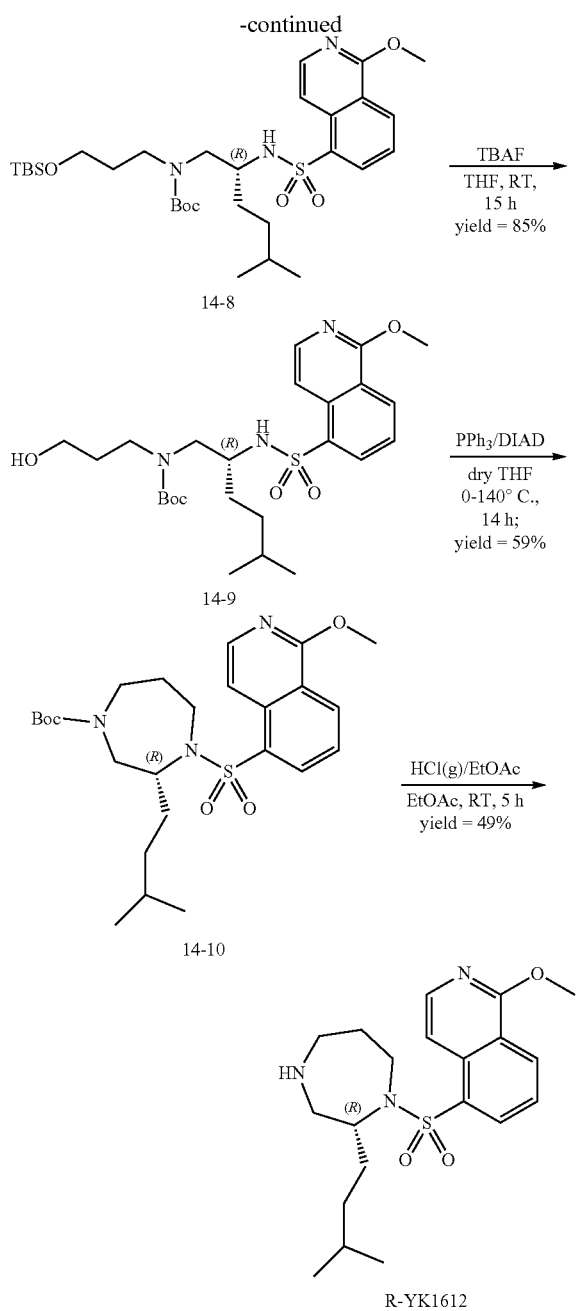

R-YK1612 had MS: [M+1]$^+$=392.1; $^1$H NMR (400 MHz DMSO), 8.51 (d, 1H), 8.41 (d, 1H), 8.17 (d, 1H), 7.87 (d, 1H), 7.72 (t, 1H), 4.06 (s, 3H), 3.95-4.00 (m, 1H), 3.65-3.69 (m, 1H), 3.22-3.26 (m, 1H), 3.01-3.06 (m, 1H), 2.52-2.75 (m, 2H), 2.38-2.44 (m, 1H), 1.39-1.48 (m, 2H), 1.08-1.10 (m, 2H), 0.91-0.93 (m, 2H), 0.87-0.89 (m, 1H), 0.82 (d, 6H).

In order to evaluate the efficacy and cytotoxicity of the compounds of the present application, the following test examples were performed.

Test Example 1: Effect of the Compounds of the Present Application on Subarachnoid Hemorrhage in Rats (1) Method for Building Model Rat subarachnoid hemorrhage (SAH) model was built by intravascular puncture. After being weighed, the rats were anesthetized with sodium pentobarbital (50 mg/kg) or chloral hydrate (300 mg/kg) by intraperitoneal injection, then fixed on their back and maintained the animal's body temperature at about 37° C. The rats' neck skin was shaved for surgery, a median incision was made on the neck, and muscle and fascia were separated along the inner edge of stemocleidomastoid muscle to expose the main and bifurcation of right common carotid artery, and expose the external and internal carotid arteries. The two branches of external carotid artery, i.e., occipital artery and superior thyroid artery, were isolated and ligated.

The bifurcation of internal carotid artery was gently clamped with ophthalmic forceps, the bifurcation of the internal carotid artery and the external carotid artery was pierced with a 6-gauge syringe needle, the ophthalmic forceps holding the bifurcation of internal carotid artery was slightly loosen, and No. 3 fishing thread was used to perform a puncture at the bleeding point, the ophthalmic forceps on the internal carotid artery was loosen, and the fishing thread was inserted into skull. When the tip of the thread for puncture was about 18 to 19 mm away from the bifurcation of the common carotid artery, resistance was felt, which indicated that the tip of the thread for puncture had reached the bifurcation of anterior cerebral artery and middle cerebral artery, the thread was further dipped about 2 mm with a little more force, at this time the thread had pierced the bifurcation of the anterior cerebral artery and the middle cerebral artery. After staying for 15 seconds, the thread for puncture was completely removed, and the skin was sutured after compression to stop the bleeding. 1.6 million units of penicillin potassium (400,000 units/ml, 0.2 ml/rat) was intramuscularly injected to avoid wound infection. For the sham operation group, the thread for puncture was removed when resistance was felt without piercing the bifurcation of the anterior cerebral artery and the middle cerebral artery, while the remaining operation steps were the same as the model group. After the operation, the rats were transferred to a thermal insulation blanket, then transferred to a squirrel cage when they were basically awake, and kept normally.

(2) Experimental Method

In this test experimental, 32 groups were set, i.e., Groups 1 to 32, in which Group 1 was a normal control group (healthy rats), Group 2 was a sham operation control group (not modeling by puncture), Group 3 was a model control group (modeling by puncture, administrated with normal saline), Group 4 was a positive control group (modeling by puncture, administrated with fasudil hydrochloride injection), and Groups 5 to 32 were test groups of the compounds of the present application (modeling by puncture, respectively administrated with the compounds of the present application); and there were 8 animals (purchased from SPF (Beijing) Biotechnology Co., Ltd., the certificate number was SYXK (Beijing) 2016-0002) in each group, half of them were female and half of them were male. The animals were subjected to fasting for 12 to 18 hours without prohibition of drinking water before modeling. After the models were built, the administration was performed once by tail vein injection, the second administration was performed 4 hours later, in total of 2 administrations with a volume of 2 ml/kg; Groups 1 to 3 were injected with normal saline, Group 4 was injected with fasudil hydrochloride injection (Eril, purchased from Asahi Kasei Pharmaceutical Co., Ltd.), Groups 5 to 32 were injected with the solutions of the compounds YK1600-1 to YK1612, R-YK1600-1 to R-YK1612 prepared in the present application at a concentration of 15 g/L (preparation method: 15 g of the compound of the present application was added into 1000 ml of water for injection, then added with 8 g of sodium chloride, respectively, after dissolution, 0.5 mol/L sodium hydroxide solution was used to adjust pH to 6.0). The rats were euthanized 24 h after the first administration, and the brains were taken. According to Sugawara's method (Reference: Sugawara T, Ayer R, Jadhav V, et al. A new grading system evaluating bleeding scale in filament perforation subarachnoid hemorrhage rat model. J Neurosci Methods. 2008, 167(2):327-34), the subarachnoid hemorrhage amounts were scored, and the scoring results were as follows:

TABLE 1

Effect of the compounds of the present application on subarachnoid hemorrhage in rats

| Serial No. | Drug for administration | Single dose (mg/kg) | Cerebral hemorrhage volume score ($\bar{x} \pm s$) |
|---|---|---|---|
| Group 1 | Normal saline | 0 | 0.00 ± 0.00 |
| Group 2 | Normal saline | 0 | 0.00 ± 0.00 |
| Group 3 | Normal saline | 0 | 15.13 ± 1.25 |
| Group 4 | Fasudil hydrochloride injection | 4 | 10.25 ± 3.24** |
| Group 5 | Compound YK1600-1 | 4 | 14.36 ± 2.53** |
| Group 6 | Compound YK1600-2 | 4 | 14.49 ± 2.62** |
| Group 7 | Compound YK1601 | 4 | 12.75 ± 2.01** |
| Group 8 | Compound YK1602 | 4 | 12.92 ± 2.03** |
| Group 9 | Compound YK1603 | 4 | 12.96 ± 1.99** |
| Group 10 | Compound YK1604 | 4 | 13.08 ± 1.97** |
| Group 11 | Compound YK1605 | 4 | 13.95 ± 2.02** |
| Group 12 | Compound YK1606 | 4 | 13.71 ± 2.03** |
| Group 13 | Compound YK1607 | 4 | 13.09 ± 2.09** |
| Group 14 | Compound YK1608 | 4 | 13.98 ± 2.01** |
| Group 15 | Compound YK1609 | 4 | 13.27 ± 1.96** |
| Group 16 | Compound YK1610 | 4 | 13.83 ± 2.01** |
| Group 17 | Compound YK1611 | 4 | 13.39 ± 2.03** |
| Group 18 | Compound YK1612 | 4 | 14.05 ± 1.96** |
| Group 19 | Compound R-YK1600-1 | 4 | 13.37 ± 2.56** |
| Group 20 | Compound R-YK1600-2 | 4 | 13.59 ± 2.67** |
| Group 21 | Compound R-YK1601 | 4 | 11.75 ± 2.05** |
| Group 22 | Compound R-YK1602 | 4 | 11.95 ± 2.04** |
| Group 23 | Compound R-YK1603 | 4 | 12.06 ± 1.98** |
| Group 24 | Compound R-YK1604 | 4 | 12.58 ± 1.96** |
| Group 25 | Compound R-YK1605 | 4 | 12.95 ± 2.04** |
| Group 26 | Compound R-YK1606 | 4 | 12.69 ± 2.01** |
| Group 27 | Compound R-YK1607 | 4 | 12.12 ± 2.06** |
| Group 28 | Compound R-YK1608 | 4 | 13.18 ± 1.97** |
| Group 29 | Compound R-YK1609 | 4 | 12.27 ± 2.02** |
| Group 30 | Compound R-YK1610 | 4 | 12.83 ± 2.05** |
| Group 31 | Compound R-YK1611 | 4 | 12.41 ± 2.03** |
| Group 32 | Compound R-YK1612 | 4 | 13.05 ± 1.96** |

Note:
Compared with the model group:
*$P < 0.05$;
**$P < 0.01$

It could be seen from Table 1 that compared with the model group, the compounds prepared in the present application showed a very significant therapeutic effect ($P<0.01$) after being administrated to the rat subarachnoid hemorrhage models, indicating that the compounds prepared in the present application had a good therapeutic effect on subarachnoid hemorrhage.

Test Example 2: Effect of the Compounds of the Present Application on the Expression of Endothelium-Derived Relaxing Factor Commercially available cytokine kits were used to detect the effects of the compounds of the present application on vascular endothelium-derived contracting factor endothelin, vascular endothelium-derived relaxing factor endothelial nitric oxide synthase, nitric oxide, and prostacyclin factor. The detection was performed according to the kit instructions. When testing the effect of the compound of the present application on cytokines, a normal control group, a fasudil hydrochloride group, and high-, medium- and low-dose groups of the compounds of the present application were set up for testing. The fasudil hydrochloride used in this test example was purchased from Beijing Sihuan Pharmaceutical Co., Ltd., with the SFDA approval number of H20173349. The EA.Hy926 cells used in this test example were purchased from Suzhou Beina Chuanglian Biotechnology Co., Ltd.

(1) Effect on the Expression of Endothelin (ET-1)

EA.Hy926 cells were taken and inoculated in a 96-well plate at $5\times10^4$ cells/mL, 100 µL per well, and cultured adherently for 24 hours, then the test compound prepared in DMEM medium was added, and an equal volume of DMEM medium was added in the normal control group, then the cells were cultured at 37° C. for 48 hours, and then the cell supernatant was taken and placed in an EP tube, and centrifuged at 3000 r/min, 4° C. for 15 min. The resulting cell supernatant was transferred to a new EP tube, diluted twice with culture medium, and detected according to the instruction of the human endothelin detection kit (purchased from Wuhan Boster Biological Engineering Co., Ltd., batch number 59113731009), and the detection results were shown in Table 2.

TABLE 2

Effect of test compounds on the expression of endothelin in endothelial cells (unit: pg/ml)

| Test compound | Detection result of test compound at high dose (10 µM) | Detection result of test compound at medium dose (2 µM) | Detection result of test compound at low dose (0.4 µM) |
|---|---|---|---|
| Normal control group | 214.19 ± 12.98 | / | / |
| Fasudil•HCl | 325.69 ± 9.78# | 252.58 ± 3.92* | 254.29 ± 3.35* |
| Compound R-YK1600-1 | 227.68 ± 3.34 | 229.34 ± 7.96* | 228.20 ± 2.28 |
| Compound R-YK1600-2 | 229.23 ± 0.75* | 225.98 ± 11.41 | 223.55 ± 0.12* |
| Compound R-YK1601 | 243.07 ± 17.37 | 266.61 ± 20.77* | 253.46 ± 19.86* |
| Compound R-YK1602 | 238.19 ± 19.65 | 285.24 ± 13.22# | 263.55 ± 0.12* |
| Compound R-YK1603 | 242.03 ± 1.24 | 252.72 ± 22.83* | 242.75 ± 52.53 |
| Compound R-YK1604 | 230.03 ± 1.24 | 242.72 ± 20.81* | 232.75 ± 42.51 |
| Compound R-YK1605 | 259.53 ± 0.75* | 228.98 ± 11.41 | 231.61 ± 9.70 |
| Compound R-YK1606 | 231.03 ± 1.24 | 242.62 ± 19.81* | 231.75 ± 32.51 |

TABLE 2-continued

Effect of test compounds on the expression of endothelin in endothelial cells (unit: pg/ml)

| Test compound | Detection result of test compound at high dose (10 μM) | Detection result of test compound at medium dose (2 μM) | Detection result of test compound at low dose (0.4 μM) |
|---|---|---|---|
| Compound R-YK1607 | 237.68 ± 3.34 | 259.34 ± 7.96* | 248.20 ± 2.28 |
| Compound R-YK1608 | 239.23 ± 0.75* | 229.98 ± 11.41 | 233.55 ± 0.12* |
| Compound R-YK1609 | 242.03 ± 1.24 | 232.72 ± 22.83* | 222.75 ± 52.53 |
| Compound R-YK1610 | 238.68 ± 3.34 | 260.34 ± 7.94* | 259.20 ± 2.21 |
| Compound R-YK1611 | 235.68 ± 3.34 | 249.34 ± 7.96* | 238.20 ± 2.28 |
| Compound R-YK1612 | 249.23 ± 0.75* | 229.98 ± 11.41 | 232.61 ± 9.70 |

Note:
*indicated $P < 0.05$ as compared with the normal control group,
indicated $P < 0.01$ as compared with the normal control group It could be seen from Table 2 that after the test compound interacted with endothelial cells for 48 hours, fasudil hydrochloride could significantly promote the expression and secretion of endothelin at high, medium and low doses, and the promotion effect was most significant at high concentration, and those at medium and low doses were similar. In addition, the compounds of the present application had a promoting effect on the expression of endothelin in endothelial cells at all three doses, indicating that the effect of the compounds of the present application on endothelial cells was consistent with that of fasudil hydrochloride.

(2) Effect on the Expression of Prostacyclin (PGI2)

EA.Hy926 cells were taken and inoculated in a 96-well plate at $5 \times 10^4$ cells/mL, 100 μL per well, and cultured adherently for 24 hours, then the test compound prepared in DMEM medium was added, and an equal volume of DMEM medium was added in the normal control group, then the cells were cultured at 37° C. for 24 hours, and then the cell supernatant was taken and placed in an EP tube, and centrifuged for 15 min at 3000 r/min and 15° C. The resulting supernatant was transferred to a new EP tube, and then the detection was performed according to the instruction of ELISA kit (purchased from Wuhan Elabscience Biotechnology Co., Ltd., Cat. No. E-EL-0022c), and the detection results were shown in Table 3.

It could be seen from Table 3 that after the test compound interacted with endothelial cells for 24 hours, fasudil hydrochloride promoted the expression of prostacyclin at low concentration, but inhibited the expression at medium and high concentrations, in which the inhibitory effect was the most obvious at high dose (P=0.052), while the compounds of the present application promoted the expression of prostacyclin factor no matter at high, medium or low dose.

(3) Detection of Endothelial Nitric Oxide Synthase (eNOS)

Detection conditions: EA.Hy926 cells were inoculated at $1 \times 10^5$ cells/nL in a 96-well plate, 100 μL per well, and cultured adherently for 24 hours, then the test compound prepared with DMEM medium was added, the normal control group was added with an equal volume of DMEM medium, then the cells were cultured for 24 hours at 37° C., and then the cell supernatant was taken and placed in an EP tube, and centrifuged at 3000 r/min and 4° C. for 15 minutes, the resulting supernatant was transferred to a new EP tube, diluted 3 times, and detected according to the instruction of eNOs detection kit (purchased from Wuhan Elabscience Biotechnology Co., Ltd., Cat. No. AK0017OCT12013), and the detection results were shown in Table 4.

TABLE 3

Effect of the test compounds on the expression of prostacyclin in endothelial cells (unit: pg/ml)

| Test compound | Detection result of test compound at high dose (10 μM) | Detection result of test compound at medium dose (2 μM) | Detection result of test compound at low dose (0.4 μM) |
|---|---|---|---|
| Normal control group | 237.75 ± 30.14 | / | / |
| Fasudil•HCl | 184.93 ± 1.09 | 208.85 ± 37.07 | 259.07 ± 40.07 |
| Compound R-YK1600-1 | 247.68 ± 3.34 | 242.34 ± 7.96 | 243.20 ± 2.28 |
| Compound R-YK1600-2 | 249.23 ± 0.75* | 245.98 ± 11.41 | 241.55 ± 0.12* |
| Compound R-YK1601 | 227.01 ± 16.23 | 253.52 ± 55.60 | 253.00 ± 5.55 |
| Compound R-YK1602 | 241.51 ± 16.58 | 263.34 ± 15.04 | 248.71 ± 19.98 |
| Compound R-YK1603 | 243.73 ± 15.66 | 272.58 ± 4.40 | 262.30 ± 0.77 |
| Compound R-YK1604 | 251.44 ± 42.48 | 279.35 ± 28.69 | 280.40 ± 9.89 |
| Compound R-YK1605 | 246.51 ± 1.44 | 274.72 ± 32.60 | 280.07 ± 7.00 |
| Compound R-YK1606 | 258.58 ± 7.57 | 278.32 ± 46.42 | 292.24 ± 2.59* |
| Compound R-YK1607 | 241.68 ± 3.34 | 257.34 ± 7.96 | 249.20 ± 2.28 |
| Compound R-YK1608 | 242.23 ± 1.75 | 251.98 ± 10.41 | 257.55 ± 4.12 |
| Compound R-YK1609 | 238.68 ± 3.34 | 260.34 ± 7.94* | 259.20 ± 2.21 |
| Compound R-YK1610 | 253.44 ± 12.48 | 267.35 ± 10.69 | 275.40 ± 9.89 |
| Compound R-YK1611 | 249.23 ± 0.75* | 229.98 ± 11.41 | 232.61 ± 9.70 |
| Compound R-YK1612 | 257.44 ± 4.48 | 269.35 ± 8.69 | 269.40 ± 8.89 |

Note:
*indicated $P < 0.05$ as compared with the normal control group

TABLE 4

Effect of the test substance on the expression of endothelial nitric oxide synthase in endothelial cells (unit: pg/ml)

| Test compound | Detection result of test compound at high dose (10 μM) | Detection result of test compound at medium dose (2 μM) | Detection result of test compound at low dose (0.4 μM) |
|---|---|---|---|
| Normal control group | 2377.57 ± 102.23 | / | / |
| Fasudil•HCl | 2636.14 ± 188.26 | 2648.66 ± 9.59 | 2810.61 ± 13.02 |
| Compound R-YK1600-1 | 2345.81 ± 213.65 | 2485.91 ± 287.57 | 2528.44 ± 267.48 |
| Compound R-YK1600-2 | 2245.86 ± 224.65 | 2384.92 ± 317.27 | 2428.32 ± 287.58 |
| Compound R-YK1601 | 2598.44 ± 365.33 | 2339.70 ± 249.84 | 2526.66 ± 220.56 |
| Compound R-YK1602 | 2262.45 ± 134.54 | 2314.00 ± 393.66 | 2607.85 ± 384.81 |
| Compound R-YK1603 | 2245.94 ± 213.65 | 2385.91 ± 387.57 | 2928.44 ± 257.48 |
| Compound R-YK1604 | 2229.68 ± 63.98 | 2397.93 ± 180.08 | 2932.05 ± 435.87 |
| Compound R-YK1605 | 2105.70 ± 87.14 | 2261.58 ± 253.77 | 2752.53 ± 779.12 |
| Compound R-YK1606 | 2286.01 ± 95.04 | 2400.67 ± 226.73 | 2974.79 ± 361.75 |
| Compound R-YK1607 | 2298.44 ± 265.33 | 2239.70 ± 249.84 | 2426.66 ± 220.56 |
| Compound R-YK1608 | 2269.45 ± 134.54 | 2344.00 ± 293.66 | 2697.85 ± 284.81 |
| Compound R-YK1609 | 2235.87 ± 213.65 | 2375.91 ± 287.28 | 2728.44 ± 257.58 |
| Compound R-YK1610 | 2329.68 ± 263.98 | 2397.93 ± 280.08 | 2632.05 ± 235.87 |
| Compound R-YK1611 | 2195.70 ± 187.16 | 2291.59 ± 253.56 | 2652.53 ± 279.27 |
| Compound R-YK1612 | 2286.671 ± 195.06 | 2456.67 ± 226.85 | 2776.58 ± 261.27 |

It could be seen from Table 4 that after the test substance interacted with endothelial cells for 24 hours, the compounds of the present application showed a promotion effect on the expression of nitric oxide synthase at low dose, and no obvious promotion or inhibition effect on the expression of nitric oxide synthase at medium dose, while at high dose, except R-YK1601 showed a slight promotion effect on the expression of nitric oxide synthase, other compounds had basically no effect on the expression of nitric oxide synthase.

(4) Effect on the Synthesis and Secretion of Nitric Oxide (NO)

EA.Hy926 cells were inoculated in a 24-well plate at $5 \times 10^5$ cells/mL, 400 μL per well, and cultured adherently for 18 hours, then the supernatant was discarded, the test compound prepared in DMEM medium was added, and an equal volume of DMEM medium was added in the normal control group, then the cells was cultured for 24 h in incubator, and then the cell supernatant was collected and detected according to the instructions of NO detection kit (purchased from Beyotime Institute of Biotechnology, Cat. No. 062617171017), and the detection results were shown in Table 5.

TABLE 5

Effect of test substance on nitric oxide secretion in endothelial cells (unit: μm)

| Test compound | Detection result of test compound at high dose (10 μM) | Detection result of test compound at medium dose (2 μM) | Detection result of test compound at low dose (0.4 μM) |
|---|---|---|---|
| Normal control group | 0.509 ± 0.070 | / | / |
| Fasudil•HCl | 1.450 ± 0.000 | 1.356 ± 0.045 | 1.131 ± 0.045 |
| Compound R-YK1600-1 | 1.148 ± 0.251 | 1.099 ± 0.201 | 1.012 ± 0.053 |
| Compound R-YK1600-2 | 1.139 ± 0.263 | 1.037 ± 0.062 | 0.982 ± 0.096 |
| Compound R-YK1601 | 1.131 ± 0.134 | 0.896 ± 0.147# | 0.806 ± 0.057 |
| Compound R-YK1602 | 1.005 ± 0.006* | 0.914 ± 0.032 | 0.878 ± 0.006 |
| Compound R-YK1603 | 0.910 ± 0.025** | 0.743 ± 0.070## | 1.207 ± 0.000 |
| Compound R-YK1604 | 0.829 ± 0.064** | 0.851 ± 0.032## | 1.009 ± 0.064 |
| Compound R-YK1605 | 1.122 ± 0.006 | 1.023 ± 0.006 | 0.950 ± 0.134 |
| Compound R-YK1606 | 1.158 ± 0.223 | 1.009 ± 0.102 | 1.131 ± 0.019 |
| Compound R-YK1607 | 1.010 ± 0.006* | 0.924 ± 0.032 | 0.898 ± 0.006 |
| Compound R-YK1608 | 1.105 ± 0.007* | 0.984 ± 0.042 | 0.918 ± 0.008 |
| Compound R-YK1609 | 1.115 ± 0.006* | 1.014 ± 0.051 | 0.978 ± 0.028 |
| Compound R-YK1610 | 1.121 ± 0.006* | 1.068 ± 0.032 | 0.997 ± 0.057 |
| Compound R-YK1611 | 1.125 ± 0.016* | 1.109 ± 0.087 | 1.095 ± 0.095 |
| Compound R-YK1612 | 1.114 ± 0.006 | 1.021 ± 0.006 | 0.960 ± 0.134 |

Note:
*indicated $P < 0.05$ vs Fasudil•HCl 10 μM group,
**indicated $P < 0.01$ vs Fasudil•HCl 10 μM group;
indicated $P < 0.05$ vs Fasudil•HCl 2 μM group,
indicated $P < 0.01$ vs Fasudil•HCl 2 μM group.

It could be seen from Table 5 that after the test compound interacted with endothelial cells for 24 hours, the compounds of the present application all had a promoting effect on the synthesis and secretion of nitric oxide at high, medium and low doses.

Test Example 3: Toxicity Test of the Compounds of the Present Application on Endothelial Cells In this test example, 31 groups, i.e., Groups 1 to 31, were set, in which Group 1 was a blank control group, Group 2 was a normal control group, Group 3 was a positive control group, and Groups 4 to 31 were test groups of the compounds of the present application. The specific test operation comprised: 100 μL of endothelial cells EA.hy926 (purchased from Suzhou Beina Chuanglian Biotechnology Co., Ltd.) with a density of 5×10⁴ was added to each well of a 96-well plate, and transferred to an incubator at 37° C. with 5% CO2 and saturated humidity conditions and cultured for 24 hours, 100 μL of 2× the test compound solution prepared and diluted with DMEM medium containing 10% fetal bovine serum was added, in which the test compound added in the positive control group was Fasudil hydrochloride (purchased from Beijing Sihuan Pharmaceutical Co., Ltd., SFDA approval number H20173349) solution with different concentrations, an equal volume of DMEM medium was added in the blank control group, an equal volume of PBS buffer was added in the normal control group, and a duplicate well was set for each concentration point. After adding the test compound, the culture was continued in the incubator for 24 hours, then 20 μL of CCK-8 detection solution (purchased from Beijing Solarbio Science & Technology Co., Ltd., Cat. No. CA1210) was added to each well, interacted at 37° C. for 2.5 hours, shaken and mixed well, and then the absorbance value at 450 nm was detected.

OD values were detected, and the cell viability values of test groups of different concentrations were calculated according to the cell viability calculation formula as follows:

Cell viability=$(A_{test\ group}-A_{blank\ control})/(A_{normal\ control}-A_{blank\ control})*100\%$ wherein A represented absorbance value at 450 nm.

Figure 2:
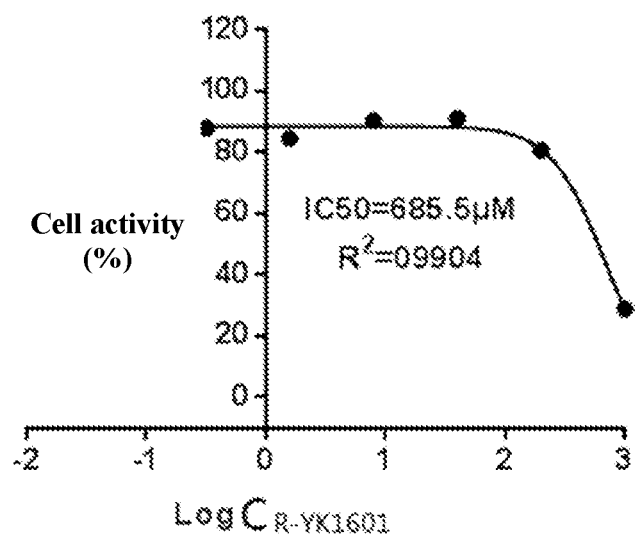
FIG. 2 shows the inhibitor concentration-viability curve of (R)-5-((2-methyl-1,4-diazacycloheptan-1-yl)sulfonyl) isoquinolin-1-ol (R-YK1601)
Figure 3:
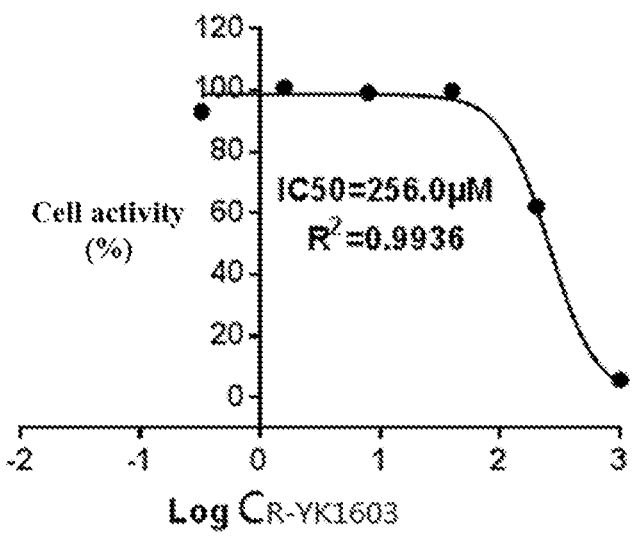
FIG. 3 shows the inhibitor concentration-viability curve of (R)-5-((2-methyl-1,4-diazacycloheptan-1-yl)sulfonyl) isoquinoline (R-YK1603)
Figure 4:
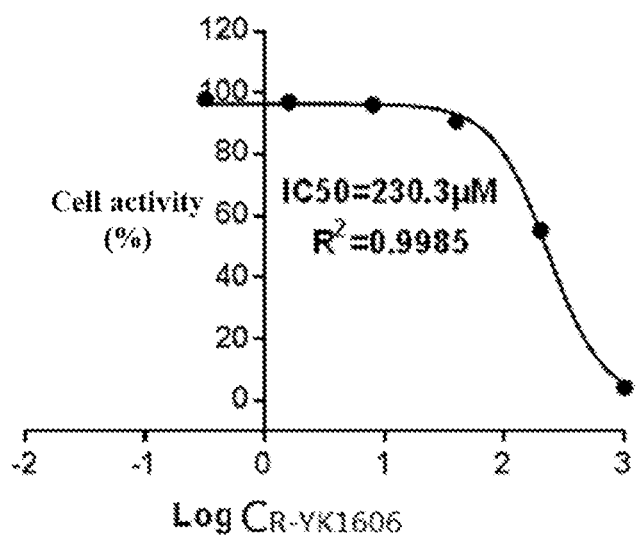
FIG. 4 shows the inhibitor concentration-viability curve of (R)-4-chloro-5-((2-methyl-1,4-diazacycloheptan-1-yl) sulfonyl)isoquinolin-1-ol (R-YK1606)
Figure 5:
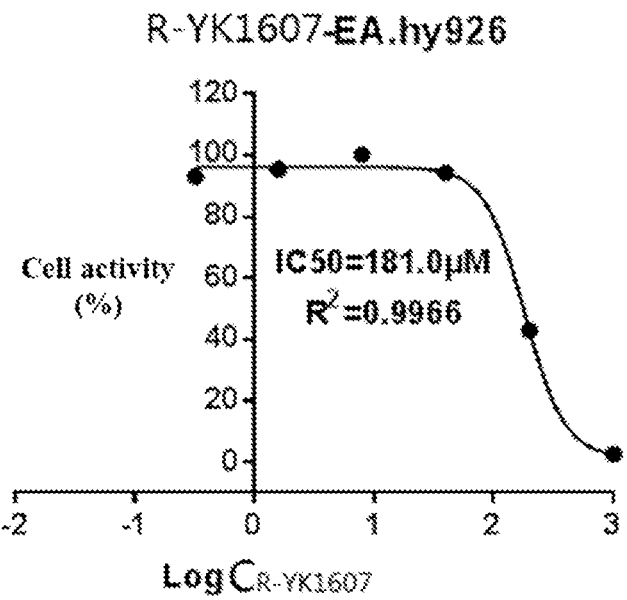
FIG. 5 shows the inhibitor concentration-viability curve of (R)-4-ethyl-5-((2-methyl-1,4-diazacycloheptan-1-yl) sulfonyl)isoquinolin-1-ol (R-YK1607)
Figure 6:
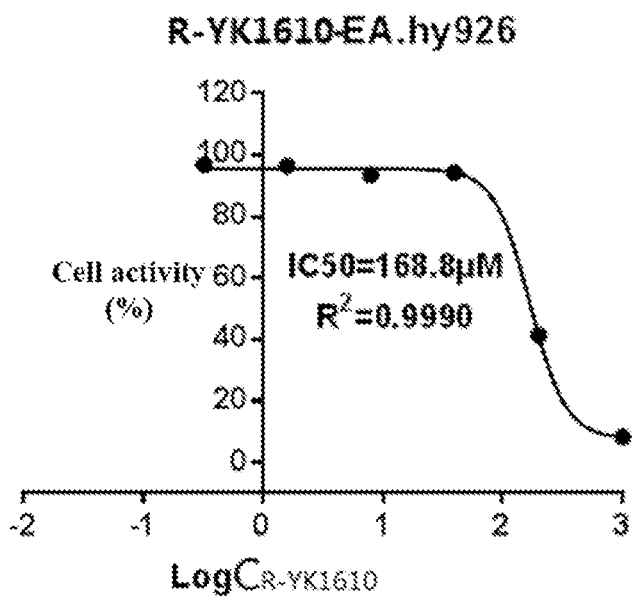
FIG. 6 shows the inhibitor concentration-viability curve of (R)-5-((2-ethyl-1,4-diazacycloheptan-1-yl)sulfonyl)-1-methoxyisoquinoline (R-YK1610).

Prism6.0 was used to obtain the inhibitor concentration-viability curve and to calculate the $IC_{50}$ of the test compound, the correlation coefficient $R^2>0.99$; the inhibitor concentration-viability curves of Fasudil hydrochloride, R-YK1601, R-YK1603, R-YK1606, R-YK1607, R-YK1610 were shown in FIGS. 1 to 6, in which the abscissa was the logarithm on base 10 of the concentration of the test compound, and the ordinate was the cell activity (i.e., cell viability).

TABLE 6

Cytotoxicity detection results of the compounds of the present application on EA.hy926 cells ($IC_{50}$)

| Serial No. | Test compound | Test compound concentration (μmol/L) | $IC_{50}$ of Test compound (μmol/L) |
| --- | --- | --- | --- |
| Group 1 | Blank control | 0 | 0 |
| Group 2 | Normal control | 0 | 0 |
| Group 3 | Fasudil hydrochloride | 1000~0.32 | 75.71 |
| Group 4 | Compound YK1600-1 | 1000~0.32 | 97.8 |
| Group 5 | Compound YK1600-2 | 1000~0.32 | 85.1 |
| Group 6 | Compound YK1601 | 1000~0.32 | 496.5 |
| Group 7 | Compound YK1602 | 1000~0.32 | 332.7 |
| Group 8 | Compound YK1603 | 1000~0.32 | 176.1 |
| Group 9 | Compound YK1604 | 1000~0.32 | 129.5 |
| Group 10 | Compound YK1605 | 1000~0.32 | 103.2 |
| Group 11 | Compound YK1606 | 1000~0.32 | 98.0 |
| Group 12 | Compound YK1607 | 1000~0.32 | 139.4 |
| Group 13 | Compound YK1608 | 1000~0.32 | 165.4 |
| Group 14 | Compound YK1609 | 1000~0.32 | 227.5 |
| Group 15 | Compound YK1610 | 1000~0.32 | 98.8 |
| Group 16 | Compound YK1611 | 1000~0.32 | 183.5 |
| Group 17 | Compound YK1612 | 1000~0.32 | 89.6 |
| Group 18 | Compound R-YK1600-1 | 1000~0.32 | 187.9 |
| Group 19 | Compound R-YK1600-2 | 1000~0.32 | 145.1 |
| Group 20 | Compound R-YK1601 | 1000~0.32 | 685.5 |
| Group 21 | Compound R-YK1602 | 1000~0.32 | 432.7 |
| Group 22 | Compound R-YK1603 | 1000~0.32 | 256.0 |
| Group 23 | Compound R-YK1604 | 1000~0.32 | 209.5 |
| Group 24 | Compound R-YK1605 | 1000~0.32 | 183.6 |
| Group 25 | Compound R-YK1606 | 1000~0.32 | 181.0 |
| Group 26 | Compound R-YK1607 | 1000~0.32 | 230.3 |
| Group 27 | Compound R-YK1608 | 1000~0.32 | 165.4 |
| Group 28 | Compound R-YK1609 | 1000~0.32 | 327.0 |
| Group 29 | Compound R-YK1610 | 1000~0.32 | 168.8 |
| Group 30 | Compound R-YK1611 | 1000~0.32 | 283.5 |
| Group 31 | Compound R-YK1612 | 1000~0.32 | 175.6 |

Note:
The test compound was diluted in a 5-fold dilution gradient from concentration of 1000 μmol/L to 0.32 μmol/L.

It could be seen from Table 6 that the $IC_{50}$ values of the compounds of the present application on EA.hy926 cells were all above 80 μM, and all greater than the $IC_{50}$ of the marketed drug Fasudil hydrochloride on EA.hy926 cells. In other words, the compounds of the present application all had less cytotoxicity than Fasudil, and higher safety than Fasudil.

Finally, it should be noted that the above examples are only used to illustrate the technical solutions of the present application rather than to limit it; although the present application has been described in detail with reference to the preferred examples, those of ordinary skill in the art should understand that: the specific implementation of the present application can be modified or some technical features thereof can be equivalently replaced; without departing from the spirit of the technical solution of the present application, all of them shall fall into the scope of the technical solution sought to be protected by the present application.

What is claimed is:

1. A compound represented by Formula I, a stereoisomer thereof or a pharmaceutically acceptable salt thereof,

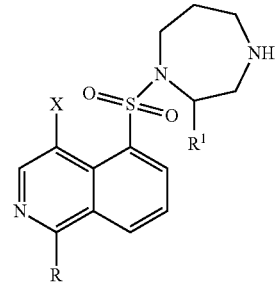

Formula I wherein, X is hydrogen, ethyl, n-propyl, isopropyl, n-butyl, isobutyl, sec-butyl, tert-butyl, cyclopropyl, cyclobutyl, cyclopentyl or cyclohexyl;

R is hydroxyl, $CH_3\ (CH_2)_mO$—, $CH_3\ (CH_2)_nCOO$— r HCO—; m and n are each independently 0, 1, 2, 3; and $R^1$ is $C_1$ to $C_5$ chain alkyl or $C_3$ to $C_6$ cycloalkyl.

2. The compound, a stereoisomer thereof or a pharmaceutically acceptable salt thereof according to claim 1, wherein $R^1$ is $C_1$ to $C_5$ chain alkyl.

3. The compound, a stereoisomer thereof or a pharmaceutically acceptable salt thereof according to claim 1, wherein $R^1$ is methyl, ethyl, n-propyl, isopropyl, n-butyl, isobutyl, sec-butyl, tert-butyl, n-pentyl, isopentyl, sec-pentyl, tert-pentyl, neopentyl, cyclopropyl, cyclobutyl, cyclopentyl, or cyclohexyl.

4. The compound, a stereoisomer thereof or a pharmaceutically acceptable salt thereof according to claim 1, wherein R is hydroxyl, methoxy, ethoxy, propoxy, or butoxy.

5. A compound, a stereoisomer thereof or a pharmaceutically acceptable salt thereof, wherein the compound is selected from the group consisting of:
    4-cyclopropyl-5-((2-methyl-1,4-diazacycloheptan-1-yl)sulfonyl)isoquinolin-1-ol;
    4-cyclopropyl-1-methoxy-5-((2-methyl-1,4-diazacycloheptan-1-yl)sulfonyl)isoquinoline;
    4-ethyl-5-((2-methyl-1,4-diazacycloheptan-1-yl)sulfonyl)isoquinolin-1-ol;
    5-((2-cyclopropyl-1,4-diazacycloheptan-1-yl)sulfonyl)isoquinoline;
    5-((2-methyl-1,4-diazacycloheptan-1-yl)sulfonyl)isoquinolin-1-ol;
    1-methoxy-5-((2-methyl-1,4-diazacycloheptan-1-yl)sulfonyl)isoquinoline;
    4-fluoro-1-methoxy-5-((2-methyl-1,4-diazacycloheptan-1-yl)sulfonyl)isoquinoline;
    4-chloro-5-((2-methyl-1,4-diazacycloheptan-1-yl)sulfonyl)isoquinolin-1-ol;
    5-((2-isopropyl-1,4-diazacycloheptan-1-yl)sulfonyl)isoquinolin-1-ol;
    5-((2-ethyl-1,4-diazacycloheptan-1-yl)sulfonyl)-1-methoxyisoquinoline;
    5-((2-n-butyl-1,4-diazacycloheptan-1-yl)sulfonyl)isoquinolin-1-ol; and
    5-((2-isopentyl-1,4-diazacycloheptan-1-yl)sulfonyl)-1-methoxyisoquinoline.

6. The compound, a stereoisomer thereof or a pharmaceutically acceptable salt thereof according to claim 5, wherein the compound is selected from the group consisting of:
    (R)-4-cyclopropyl-5-((2-methyl-1,4-diazacycloheptan-1-yl)sulfonyl)isoquinolin-1-ol;
    (R)-4-cyclopropyl-1-methoxy-5-((2-methyl-1,4-diazacycloheptan-1-yl)sulfonyl)isoquinoline;
    (R)-4-ethyl-5-((2-methyl-1,4-diazacycloheptan-1-yl)sulfonyl)isoquinolin-1-ol;
    (R)-5-((2-cyclopropyl-1,4-diazacycloheptan-1-yl)sulfonyl)isoquinoline;
    (R)-5-((2-methyl-1,4-diazacycloheptan-1-yl)sulfonyl)isoquinolin-1-ol;
    (R)-1-methoxy-5-((2-methyl-1,4-diazacycloheptan-1-yl)sulfonyl)isoquinoline;
    (R)-4-fluoro-1-methoxy-5-((2-methyl-1,4-diazacycloheptan-1-yl)sulfonyl)isoquinoline;
    (R)-4-chloro-5-((2-methyl-1,4-diazacycloheptan-1-yl)sulfonyl)isoquinolin-1-ol;
    (R)-5-((2-isopropyl-1,4-diazacycloheptan-1-yl)sulfonyl)isoquinolin-1-ol;
    (R)-5-((2-ethyl-1,4-diazacycloheptan-1-yl)sulfonyl)-1-methoxyisoquinoline;
    (R)-5-((2-n-butyl-1,4-diazacycloheptan-1-yl)sulfonyl)isoquinolin-1-ol; and
    (R)-5-((2-isopentyl-1,4-diazacycloheptan-1-yl)sulfonyl)-1-methoxyisoquinoline.

7. The compound, a stereoisomer thereof or a pharmaceutically acceptable salt thereof according to claim 1, wherein the pharmaceutically acceptable salt is a salt formed by the compound and an inorganic acid or an organic acid; wherein the salt formed by the compound and the inorganic acid is sulfate, hydrochloride, nitrate, phosphate, or hydrobromide, and the salt formed by the compound and the organic acid salt is selected from the group consisting of acetate, formate, methanesulfonate, trifluoroacetate, maleate, tartrate, succinate, fumarate, citrate, benzenesulfonate, benzoate, lactate, malate, and an amino acid salt.

8. The compound, a stereoisomer thereof or a pharmaceutically acceptable salt thereof according to claim 7, wherein
    the amino acid salt is selected from the group consisting of aspartate, glutamate, glycinate, alaninate, valinate, leucinate, isoleucinate, phenylalaninate, prolinate, tryptophanate, serinate, tyrosinate, cysteinate, methioninate, asparaginate, glutaminate, and threoninate.

9. A method for preparing the compound, a stereoisomer thereof or a pharmaceutically acceptable salt thereof according to claim 1, comprising:
    allowing a compound represented by Formula II to undergo a deprotection reaction to remove the protective group PG to prepare the compound represented by the Formula I,

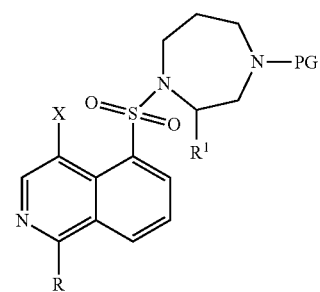

Formula II wherein the definitions of X, R and $R^1$ are as described in claim 1; and PG is tert-butoxycarbonyl or benzyloxycarbonyl.

10. The method according to claim 9, wherein the compound represented by Formula II is prepared by a cyclization reaction of a compound represented by Formula III,

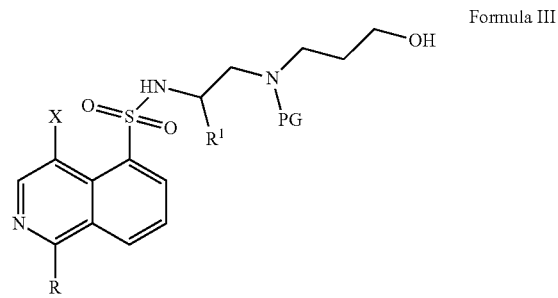

Formula III wherein, the definitions of X, R, $R^1$ and PG are as described in claim 9.

11. The method according to claim 10, wherein the compound represented by Formula III is prepared by removing the protective group $PG^1$ from a compound represented by Formula IV through a deprotection reaction;

Formula IV

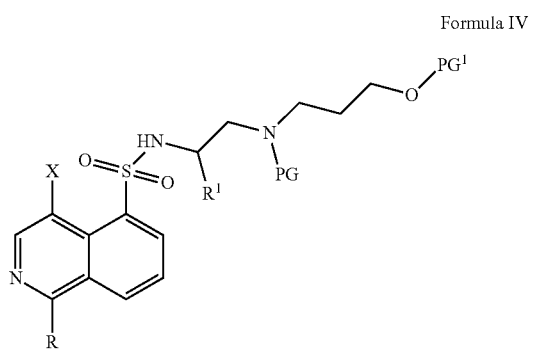

wherein, the definitions of X, R, R¹ and PG are as described in claim 10; and

PG¹ is tert-butyldimethylsilyl or trimethylsilyl.

12. The method according to claim 11, wherein the compound represented by Formula IV is prepared by reacting a compound represented by Formula V with a compound represented by Formula VI;

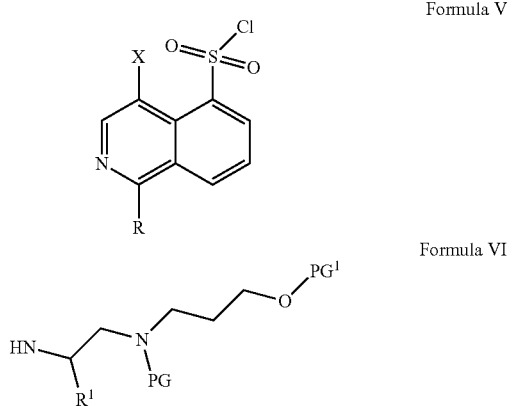

Formula V

Formula VI wherein, X, R, R¹, PG and PG¹ are defined as described in claim 11.

13. The method according to claim 12, wherein the compound represented by Formula V is prepared by reacting a compound represented by Formula VII with chlorosulfonic acid,

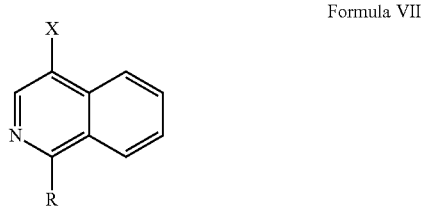

Formula VII wherein, the definitions of X and R are as described in claim 12.

14. A pharmaceutical composition, which comprises the compound, a stereoisomer thereof or a pharmaceutically acceptable salt thereof according to claim 1, and at least one pharmaceutically acceptable carrier or excipient.

15. A method for preventing and/or treating a subarachnoid hemorrhage, or a vasospasm or cerebral ischemia caused by subarachnoid hemorrhage, selectively expanding spasmodic blood vessel, improving cardiac/cerebral ischemia, improving cerebral perfusion, enhancing brain antihypoxic ability, inhibiting brain nerve cell damage, promoting neuron axon growth, or alleviating inflammatory response of affected brain cell tissue, comprising administering a prophylactically or therapeutically effective amount of the compound, a stereoisomer thereof or a pharmaceutically acceptable salt thereof according to claim 1 to a subject in need of such treatment.

16. A method for promoting the expression and secretion of a vasoconstriction factor in a cell, or promoting the expression of a vascular endothelium-derived relaxing factor in a cell, comprising contacting the compound, a stereoisomer thereof or a pharmaceutically acceptable salt thereof according to claim 1 with the cell.

17. The method according to claim 16, wherein the vasoconstriction factor comprises an endothelin factor; and the vascular endothelium-derived relaxing factor comprises a prostacyclin factor, a nitric oxide synthase factor, and a nitric oxide factor.

* * * * *